(12) United States Patent
Radu et al.

(10) Patent No.: US 9,688,673 B2
(45) Date of Patent: Jun. 27, 2017

(54) DEOXYCYTIDINE KINASE BINDING COMPOUNDS

(75) Inventors: Caius G. Radu, Los Angeles, CA (US); Hsiang-I Liao, Arcadia, CA (US); Nagichettiar Satyamurthy, Los Angeles, CA (US); Johannes Czernin, Pacific Palisades, CA (US); Jennifer M. Murphy, Los Angeles, CA (US); David A. Nathanson, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 293 days.

(21) Appl. No.: 14/002,964

(22) PCT Filed: Mar. 8, 2012

(86) PCT No.: PCT/US2012/028259
§ 371 (c)(1),
(2), (4) Date: Sep. 3, 2013

(87) PCT Pub. No.: WO2012/122368
PCT Pub. Date: Sep. 13, 2012

(65) Prior Publication Data
US 2013/0336883 A1    Dec. 19, 2013

Related U.S. Application Data

(60) Provisional application No. 61/450,319, filed on Mar. 8, 2011, provisional application No. 61/579,443, filed on Dec. 22, 2011.

(51) Int. Cl.
| | | |
|---|---|---|
| *A61K 51/00* | (2006.01) | |
| *A61M 36/14* | (2006.01) | |
| *C07D 417/12* | (2006.01) | |
| *C07D 417/14* | (2006.01) | |
| *A61K 31/426* | (2006.01) | |
| *A61K 31/44* | (2006.01) | |
| *A61K 31/506* | (2006.01) | |
| *A61K 31/513* | (2006.01) | |
| *G01N 33/50* | (2006.01) | |

(52) U.S. Cl.
CPC .......... *C07D 417/12* (2013.01); *A61K 31/426* (2013.01); *A61K 31/44* (2013.01); *A61K 31/506* (2013.01); *A61K 31/513* (2013.01); *C07D 417/14* (2013.01); *G01N 33/5088* (2013.01)

(58) Field of Classification Search
CPC .. C07D 417/12; C07D 417/14; A61K 31/426; A61K 31/44; A61K 31/506; A61K 31/513; G01N 33/5088
USPC ....................................................... 424/1.11
See application file for complete search history.

(56) References Cited

U.S. PATENT DOCUMENTS

| | | | |
|---|---|---|---|
| 8,101,740 B2 | 1/2012 | Radu et al. | |
| 2007/0100137 A1* | 5/2007 | Dellinger et al. | 536/25.3 |
| 2009/0163545 A1* | 6/2009 | Goldfarb | 514/312 |
| 2010/0022544 A1* | 1/2010 | Nell et al. | 514/236.8 |

FOREIGN PATENT DOCUMENTS

| | | |
|---|---|---|
| WO | 02/59098 | 8/2002 |
| WO | 03/072100 | 9/2003 |
| WO | 03/072102 | 9/2003 |
| WO | 2004/092131 | 10/2004 |
| WO | 2007/039171 | 4/2007 |
| WO | 2008/076778 | 6/2008 |
| WO | 2009/038795 | 3/2009 |

OTHER PUBLICATIONS

Tarver et al. Bioorg. Med. Chem. 2009, 19, 6780-6783.*
Jessop et al. Bioorg. Med. Chem. 2009, 19, 6784-6787.*
Zhang et al. Curr. Top. Med. Chem. 2007, 7, 1817-1829.*
Chauhan et al., "Heterocyclic o-xylylenes; thiazole, oxazole and imidazole analogues". Tetrahedron Letters, 1990, vol. 31, pp. 1487-1490.
Laing et al., "Noninvasive prediction of tumor responses to gemcitabine using positron emission tomography", Proceedings of the National Academy of Sciences of the United States of America, 2009, vol. 106, pp. 2847-2852.
CAS Registry No. 791022-41-8, STN Entry Date Nov. 30, 2004.
DD 235642 A1 (Humboldt-Universitat Zu Berlin(May 14, 1986 & Chemical Abstract Accession No. 1987:156452, CAS Registry No. 105751-83-5.
PCT International Search Report for PCT Application No. PCT/US2012/028259.
Radu et al., "Molecular imaging of lymphoid organs and immune activation by positron emission tomography with a new [18F]-labeled 2'-deoxycytidine analog", Nature medicine, 2008, 14(7): 783-788.
Shu et al., "Novel PET probes specific for deoxycytidine kinase", Journal of Nuclear Medicine, 2010, 51(7): 1092-1098.
Beyaert et al., "A crucial role for ATR in the regulation of deoxycytidine kinase activity," Biochem Pharmacol., 100:40-50 (2016).
Nathanson et al., "Co-targeting of convergent nucleotide biosynthetic pathways for leukemia eradication," Journal of Experimental Medicine, 211(3):473-486 (2014).
Nomme et al., "Structural characterization of new deoxycytidine kinase inhibitors rationalizes the affinitydetermining moieties of the molecules," Acta Crystallographica Section D Biological Crystallography, D70:68-78 (2014).

* cited by examiner

Primary Examiner — Michael G Hartley
Assistant Examiner — Sean R Donohue
(74) Attorney, Agent, or Firm — Mintz Levin Cohn Ferris Glovsky and Popeo, P.C.

(57) ABSTRACT

The invention provides compounds that bind to deoxycytidine kinase (dCK) and compositions including pharmaceutically acceptable compositions containing the compounds. The compounds are useful in treating diseases and disorders where dCK activity is implicated such as cancer and immune disorders. The compounds also find use in clinical methodologies including positron emission tomography (PET) imaging.

20 Claims, 27 Drawing Sheets

Figure 1

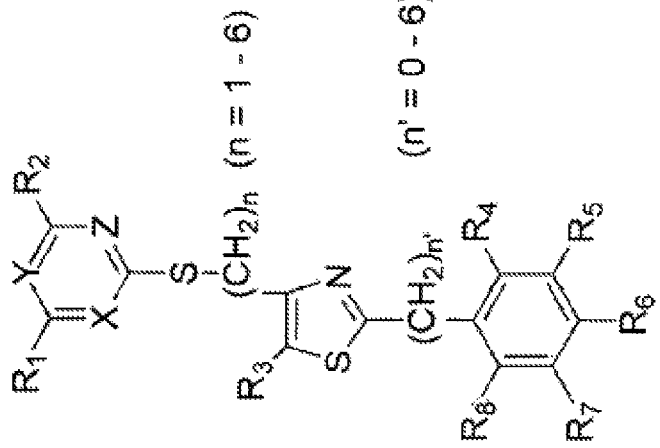

X, Y, Z = CH or N $R_1, R_2$ = $NH_2$, $NH_3W$, $NH_3Me$, $NH_3Et$, OH, $OCH_3$ or $OC_2H_5$ $R_3$ = H, $CH_3$, $C_2H_5$, $C_3H_7$ or $OCH_3$ $R_4, R_5, R_6, R_7, R_8$ = H, F, Cl, Br, I, $OR_9$ ($R_9$ = $CH_3$, $C_2H_5$, $C_3H_7$, $C_4H_9$, $C_5H_{11}$, $C_6H_{13}$, $CH_2F$, $C_2H_4F$, $C_3H_6F$, $C_4H_8F$, $C_5H_{10}F$, $C_6H_{12}F$, $C_2H_4Br$, $C_2H_4I$, $CF_3$, $C_2F_5$, $C_3F_7$, $C_4F_9$, $C_5F_{11}$, $C_6F_{13}$), $OR_{10}$ ($R_{10}$ = $CH_2OTs$, $C_2H_4OTs$, $C_3H_6OTs$, $C_4H_8OTs$, $C_5H_{10}OTs$, $C_6H_{12}OTs$ while Ts = tosyl), $OR_{11}$ ($R_{11}$ = $CH_2OH$, $C_2H_4OH$, $C_3H_6OH$, $C_4H_8OH$, $C_5H_{10}OH$, $C_6H_{12}OH$), $OR_{12}$ ($R_{12}$ = $CH_2OTHP$, $C_2H_4OTHP$, $C_3H_6OTHP$, $C_4H_8OTHP$, $C_5H_{10}OTHP$, $C_6H_{12}OTHP$ while THP = 2-tetrahydropyranyl group ), $OR_{13}$ ($R_{13}$ = $CH_2 X^*$, $C_2H_4 X^*$, $C_3H_6 X^*$, $C_4H_8 X^*$, $C_5H_{10} X^*$, $C_6H_{12} X^*$), W = F, Cl, Br, I, $NO_3$, $SO_4$, $HSO_4$, $H_2PO_4$, $HPO_4$, $PO_4$, etc $X^*$ can be F-18, Br-75, Br-76, I-124

Notes:
• all compounds based on this scaffold are amenable to one-step F-18 radiolabeling
• bond angles are distorted for clarity.

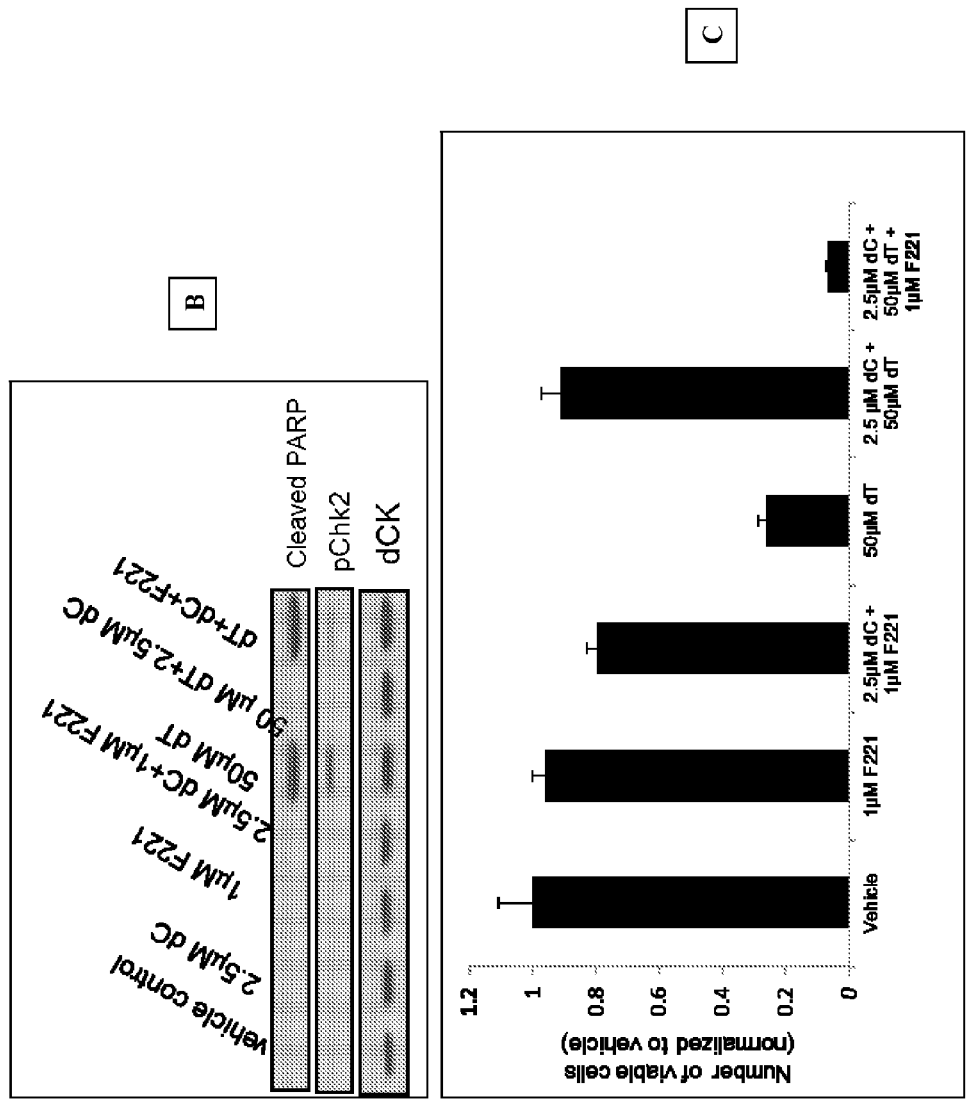
Figure 7 (B & C)

Figure 13
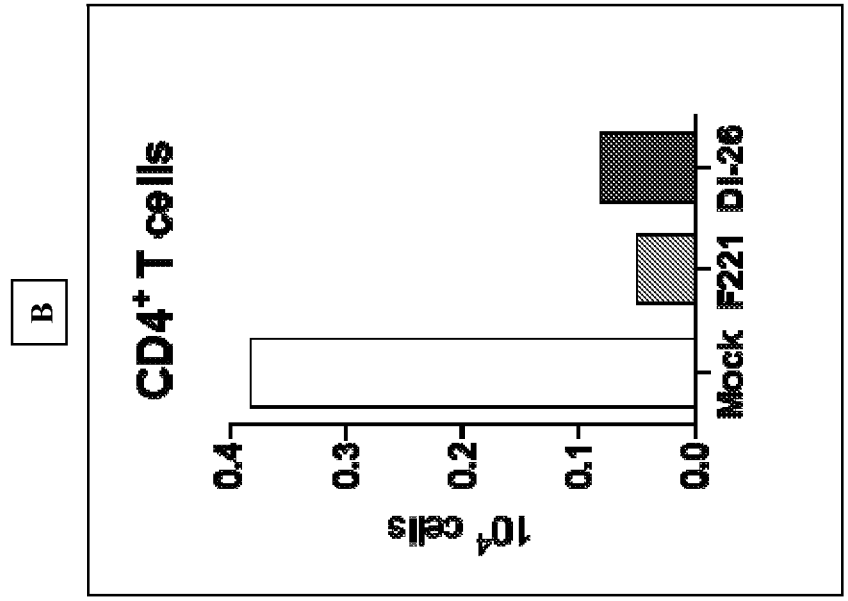
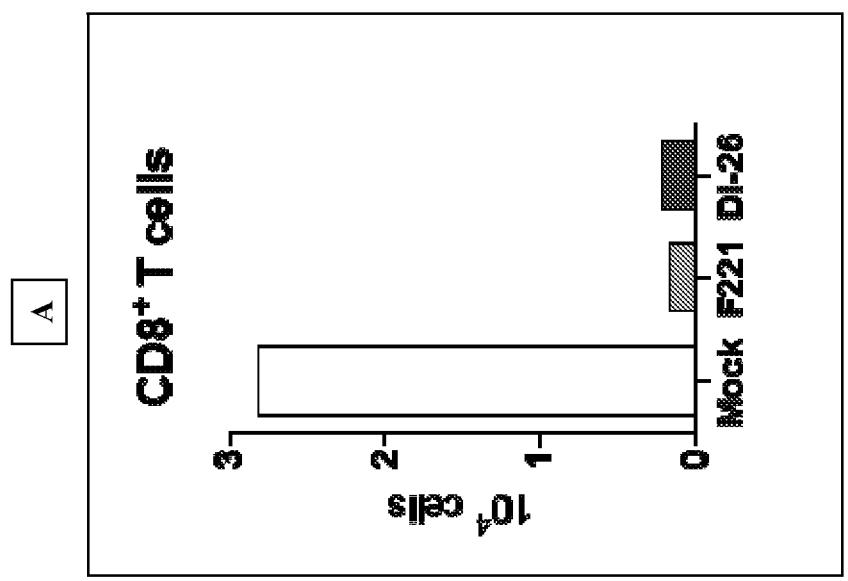

Figure 16A

General reaction scheme for formulating dCK inhibitors as salts

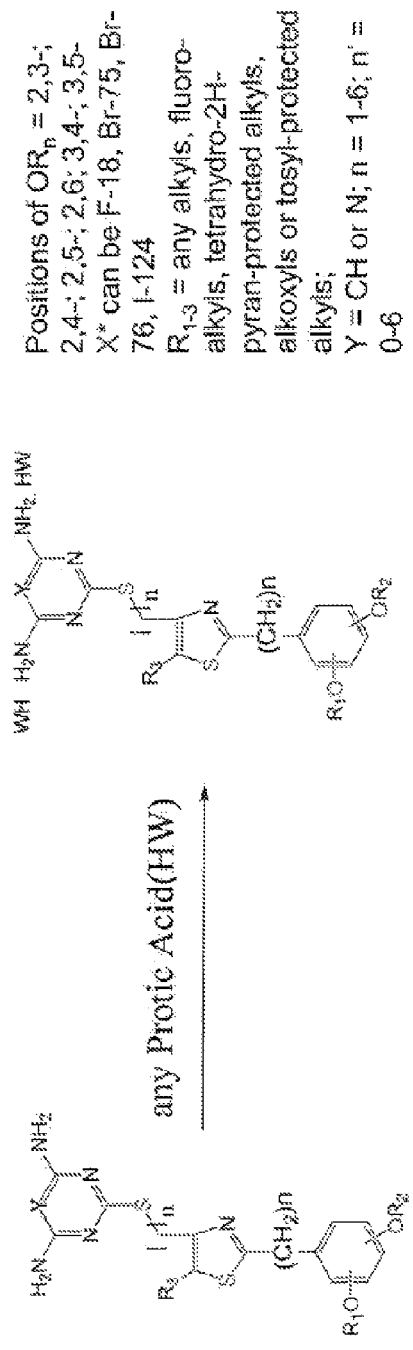

Positions of $OR_n$ = 2,3-; 2,4-; 2,5-; 2,6; 3,4-; 3,5-
$X^*$ can be F-18, Br-75, Br-76, I-124
$R_{1-3}$ = any alkyls, fluoro-alkyls, tetrahydro-2H-pyran-protected alkyls, alkoxyls or tosyl-protected alkyls;
Y = CH or N; n = 1-6; n' = 0-6

Procedure:
1) DI-FX was dissolved in a common organic solvent, e.g. but not limited to acetone, tetrahydrofuran, methanol, ethanol, alcohol, dimethylformamide, dimethyl sulfoxide, triethylamine, pyridine, etc.
2) Protic acid (not limited to the following): hydrofluoric acid, hydrochloric acid, hydrobromic acid, hydroiodic acid, hypochloric acid, chloric acid, perchloric acid, periodic acid, sulfuric acid, fluorosulfuric acid, nitric acid, phosphoric acid, fluoroantimonic acid, fluoroboric acid, hexafluorophosphoric acid, chromic acid, boric acid, methanesulfonic acid, ethanesulfonic acid, benzenesulfonic acid, p-toluenesulfonic acid, trifluoromethanesulfonic acid, polystyrene sulfonic acid, acetic acid, citric acid, formic acid, lucomic acid, lactic acid, oxalic acid, tartaric acid, phthalic acid, ascorbic acid, meldrum's acid, etc. was added to precipitate the DI-FX.2HW salt.
3) The salt was filtered, washed with minimum amount of the organic solvent and dried under vacuum.
4) The product was redissolved in water before use.

Figure 16B

General reaction scheme for formulating dCK inhibitors as salts

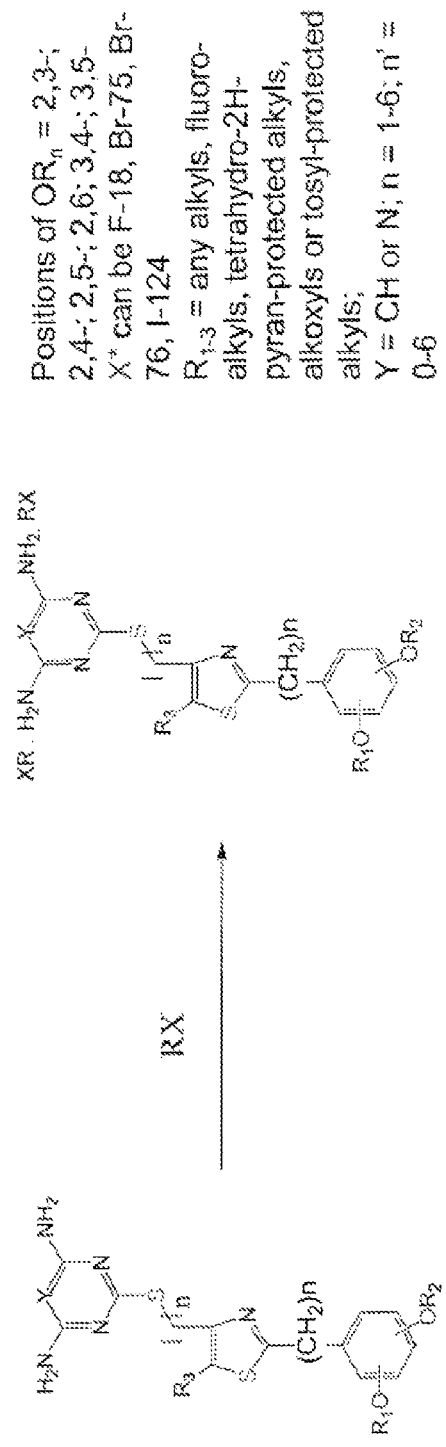

Positions of $OR_n$ = 2,3-; 2,4-; 2,5-; 2,6; 3,4-; 3,5-
$X^+$ can be F-18, Br-75, Br-76, I-124
$R_{1-3}$ = any alkyls, fluoro-alkyls, tetrahydro-2H-pyran-protected alkyls, alkoxyls or tosyl-protected alkyls;
Y = CH or N; n = 1-6; n' = 0-6

Procedure:
1) DI-FX was dissolved in common organic solvent, e.g. but not limited to the following acetone, tetrahydrofuran, methanol, ethanol, alcohol, dimethylformamide, dimethyl sulfoxide, triethylamine, pyridine, etc.
2) Not limit to methyl iodide, ethyl iodide, was added to precipitate the DI-FX.2RX salt.
3) The salt was filtered, washed with minimum amount of the organic solvent and dried under vacuum.
4) The product was redissolved in water whenever for its application.

DEOXYCYTIDINE KINASE BINDING COMPOUNDS

CROSS-REFERENCE TO RELATED APPLICATIONS

This application claims priority to U.S. Provisional Patent Application No. 61/450,319 filed Mar. 8, 2011, and U.S. Provisional Patent Application No. 61/579,443 filed Dec. 22, 2011, the disclosures of which are incorporated herein by reference in their entireties.

STATEMENT AS TO RIGHTS TO INVENTIONS MADE UNDER FEDERALLY SPONSORED RESEARCH AND DEVELOPMENT

This invention was made with Government support under Grant No. CA086306, CA151819, EB013685, awarded by the National Institutes of Health. The Government has certain rights in this invention.

FIELD OF THE INVENTION

The instant disclosure relates to compounds that bind to and inhibit deoxycytidine kinase (dCK) activity and uses thereof in therapeutic methods of treating diseases and disorders involving dCK activity. The disclosure also relates to uses of the compounds in PET imaging and diagnostic methods related to dCK binding.

BACKGROUND OF THE INVENTION

Deoxycytidine kinase (dCK) is an enzyme which plays a crucial role in role in cellular divisional and which functions in the phosphorylation of several deoxyribonucleosides and their nucleoside analogs. Deoxycytidine kinase is observed to be predominantly expressed in hematopoietic tissues and is upregulated in certain solid tumors. Interestingly, dCK deficiency is also associated with certain forms of resistance to antiviral and anticancer chemotherapeutic agents. dCK is a clinically important polypeptide target because of, for example, its role in cellular divisional, as well as its association with drug resistance and/or drug sensitivity. Compounds and compositions that bind to and inhibit dCK activities in vivo are desirable for the treatment of diseases and disorders where dCK activity is implicated.

By monitoring aspects of immune function throughout the body of a patient, medical practitioners can significantly impact the diagnosis and treatment of pathological conditions including immunological disorders. Positron Emission Tomography (PET) is one example of a molecular imaging modality with numerous applications in cancer and other diseases. Positron Emission Tomography, for example, enables the measurements of molecular and cellular mechanisms throughout the body in preclinical and clinical settings. Such measurements have widespread diagnostic utility and their use for evaluation of treatment responses and to assist drug development is expanding rapidly. Studies have demonstrated the feasibility of using PET to visualize immune responses and, for example, shown that anti-tumor T cell immunity can be monitored using PET reporter gene imaging. Similar approaches may enable evaluation of T cell trafficking thus expanding their use in patients undergoing cancer immunotherapy. PET studies of immune function have been limited by a lack of specialized probes. In this context, development of probes that allow for direct measurements of immune function will significantly widen the utility of PET imaging. Compounds that bind polypeptides involved in nucleoside metabolism such as deoxycytidine kinase may find use in therapeutic methods that involve the inhibition of nucleoside metabolism as well as in imaging methods that aid the evaluation and development of therapeutic agents that inhibit polypeptides involved in nucleoside metabolism such as dCK.

BRIEF SUMMARY OF THE INVENTION

In one aspect, provided is a compound of the formula (I):

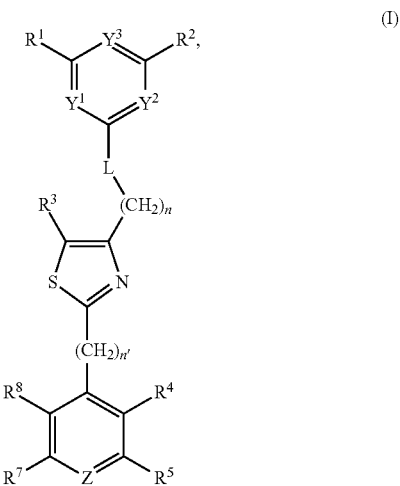

or a salt thereof, wherein:
$R^1$ and $R^2$ are independently H, OH, $OR^{14}$, $NH_2$, $NHC(O)R^{15}$ or $NHC(O)OR^{17}$;
each $Y^1$, $Y^2$ and $Y^3$ is independently N or CH;
L is O, S, SO, $SO_2$, Se, NH or $NR^{16}$;
each m, n, p, q and r is independently 1, 2, 3, 4, 5 or 6;
n' is 0, 1, 2, 3, 4, 5 or 6;
$R^3$ is $C_1$-$C_6$ alkyl, $C_3$-$C_8$ cycloalkyl, aryl, heteroaryl or $OCH_3$;
$R^4$ and $R^8$ are independently H, F, Cl, Br, I, $CF_3$ or $OR^9$;
$R^5$ and $R^7$ are independently H, F, Cl, Br, I, $CF_3$, fluoropyridyl or $OR^{10}$;
Z is N or $CR^6$;
$R^6$ is H, F, Cl, Br, I, $CF_3$ or $OR^{11}$;
$R^9$ and $R^{11}$ are independently $C_1$-$C_6$ alkyl, $C_1$-$C_6$ perfluoroalkyl, $(CH_2)_mX$, $(CH_2)_pOR^{12}$, or $(CH_2)_rX^*$;
$R^{10}$ is $C_1$-$C_6$ alkyl, $C_1$-$C_6$ perfluoroalkyl, $(CH_2)_mX$, $(CH_2)_p OR^{12}$, $(CH_2)_q R^{13}$ or $(CH_2)_r X^*$;
$R^{12}$ is H, tosyl or 2-tetrahydropyranyl;
$R^{13}$ is $OCH_3$, $NH_2$, $NHCOCH_3$, $CO_2H$, $CO_2CH_3$, SH or $COCH_3$;
$R^{14}$ is $C_1$-$C_4$ alkyl;
$R^{15}$ is $C_1$-$C_6$ alkyl or $CF_3$;
$R^{16}$ is $C_1$-$C_4$ alkyl or phenyl;
$R^{17}$ is $C_1$-$C_6$ alkyl;
X is F, Cl, Br or I; and
$X^*$ is $^{18}F$, $^{75}Br$, $^{76}Br$ or $^{124}I$.

In some embodiments, the compound is of the formula (I), or a salt thereof, wherein: $R^1$ and $R^2$ are $NH_2$; each $Y^1$, $Y^2$ and $Y^3$ is independently N or CH; L is O, S, SO, $SO_2$, Se, NH or $NR^{16}$; each m, n, p and q is independently 1, 2, 3, 4, 5 or 6; n' is 0; $R^3$ is methyl, ethyl, propyl, butyl, cyclohexyl, phenyl, thiophenyl or furanyl; Z is N or $CR^6$; each of $R^4$, $R^6$, $R^7$ and $R^8$ is independently H, F, $CF_3$ or $OCH_3$; provided that no more than one of $R^4$, $R^6$, $R^7$ and $R^8$ is F, $CF_3$ or $OCH_3$; $R^5$ is $OR^{10}$; $R^{10}$ is $(CH_2)_mX$, $(CH_2)_pOH$ or $(CH_2)_qR^{13}$; $R^{13}$ is $OCH_3$, $NH_2$, $NHCOCH_3$, $CO_2H$, $CO_2CH_3$, SH or $COCH_3$; $R^{16}$ is methyl, ethyl, propyl, butyl or phenyl; and X is F, Cl, Br or I.

In another aspect, provided are methods for inhibiting a deoxycytidine kinase (dCK) activity comprising contacting a compound detailed herein with the deoxycytidine kinase, either in vitro or in vivo. Also provided is a method for treating cancer (e.g., leukemia, ovarian cancer, lung cancer, pancreatic cancer, hepatocellular carcinoma, or a cancer independent of tissue of origin that are characterized by genomic instability and/or activation of the DNA damage response) in an individual comprising administering to the individual an effective amount of a compound detailed herein in conjunction with thymidine. Also provided is a method for treating an immune disorder, such as an autoimmune disorder or transplant rejection, in an individual in need thereof comprising administering to the individual an effective amount of a compound detailed herein, or a pharmaceutically acceptable salt thereof.

Also provided are pharmaceutical compositions comprising a compound detailed herein and a pharmaceutically acceptable carrier or excipient. Kits comprising a compound detailed herein and optionally instructions for use are also provided. Compounds as detailed herein or a pharmaceutically acceptable salt thereof are also provided for the manufacture of a medicament for the treatment of cancer or an immune disorder.

Further, the invention disclosed herein has a number of embodiments including compositions of matter, methods of using these compositions in diagnostic imaging techniques as well as methods of using these compositions to inhibit the nucleoside metabolism of cells. In certain embodiments for example, the invention provides a class of labeled PET probes to observe and/or measure dCK activity in vivo. Such embodiments of the invention can be used in diagnostic imaging techniques of certain cell populations including T lymphocytes.

In certain embodiments of the invention, dCK inhibitor compounds disclosed herein may be useful in therapeutic methods designed to inhibit the nucleoside metabolism of cells (e.g. as occurs with a number of therapeutic compounds used in the treatment of certain cancers). Similarly, these compounds may further provide treatment options for immune disorders (e.g. autoimmunity and prevention of transplant rejection). Consequently, the invention provides methods of diagnosis and/or treatment of conditions that implicate cells with high deoxyribonucleoside salvage pathway activity, e.g., lymphocytes, bone marrow cells, and intestinal enterocytes. Embodiments of the invention further provide methods for evaluating the usage efficacy of particular classes of anticancer agents in the treatment of cancer such as those that are taken up into cells via nucleoside transporters and deoxycytidine kinase (dCK)-mediated phosphorylation.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1 provides a schematic of some embodiments of the compound of the invention.

FIG. 13 shows the effect of Compounds F2.2.1 and DI-26 on the proliferation of T lymphocytes ($CD4^+$ and $CD8^+$ T cells).

FIGS. 16A and 16B provides exemplary methods for preparing salts and formulating compounds such as the dCK inhibitors described herein.

DETAILED DESCRIPTION OF THE INVENTION

Definitions

Figure 2:
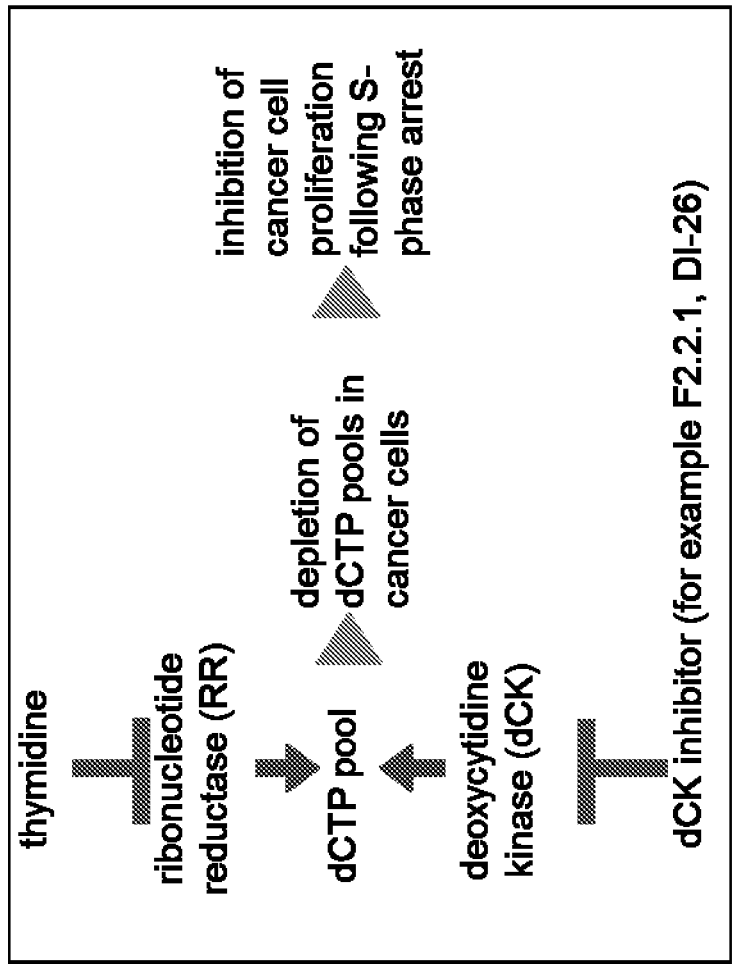
FIG. 2 is a schematic illustrating a theory that the deoxycytidine triphosphate (dCTP) pools are depleted by thymidine combined with deoxycytidine kinase (dCK) inhibitors.

The term "alkyl" refers to and includes linear or branched univalent hydrocarbon structures and combination thereof, which may be fully saturated, mono- or polyunsaturated, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Examples of saturated $C_1$-$C_4$ alkyl include methyl ($CH_3$), ethyl ($C_2H_5$), propyl ($C_3H_7$) and butyl ($C_4H_9$). Examples of saturated $C_1$-$C_6$ alkyl include methyl ($CH_3$), ethyl ($C_2H_5$), propyl ($C_3H_7$), butyl ($C_4H_9$), pentyl ($C_5H_{11}$) and hexyl ($C_6H_{13}$).

An alkyl group may be substituted (i.e., one or more hydrogen atoms are replaced with univalent or divalent radicals) with one more substituents, such as radicals described herein, for example, fluoro, chloro, bromo, iodo, hydroxyl, alkoxy, thio, amino, acylamino, alkoxycarbonylamido, carboxyl, acyl, alkoxycarbonyl, sulfonyl, cycloalkyl, aryl, heterocyclyl and heteroaryl, and other functional groups known in the art. A "perfluoroalkyl" refers to an alkyl group where every hydrogen atom is replaced with a fluorine atom. Examples of saturated $C_1$-$C_6$ perfluoroalkyl include trifluoromethyl ($CF_3$), pentafluoroethyl ($C_2F_5$), heptafluoropropyl ($C_3F_7$), nonafluorobutyl ($C_4F_9$), undecafluoropentyl ($C_5F_{11}$) and tridecafluorohexyl ($C_6F_{13}$).

The term "cycloalkyl" refers to and includes cyclic univalent hydrocarbon structures, which may be fully saturated, mono- or polyunsaturated, having the number of carbon atoms designated (i.e., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

The term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

The term "aryl" refers to and includes polyunsaturated aromatic hydrocarbon substituents. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

Cycloalkyl, aryl, heterocyclyl and heteroaryl groups may also be substituted with one or more substituents, such as radicals detailed herein, for example, fluoro, chloro, bromo, iodo, hydroxyl, alkoxy, thio, amino, acylamino, alkoxycarbonylamido, carboxyl, acyl, alkoxycarbonyl, sulfonyl, alkyl, cycloalkyl, aryl, heterocyclyl and heteroaryl, and other functional groups known in the art.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, such as those known in the art, for example, described in *Remington's Pharmaceutical Sciences* 16th edition, Osol, A. Ed. (1980).

As used herein, "treatment" or "treating" is an approach for obtaining beneficial or desired results including and preferably clinical results. For example, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

Unless clearly indicated otherwise, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. The invention may find use in both human medicine and in the veterinary context.

As used herein and in the appended claims, the singular forms "a," "an," and "the" include plural reference unless the context clearly indicates otherwise.

It is understood that aspect and variations of the invention described herein include "consisting" and/or "consisting essentially of" aspects and variations.

Compounds

In one aspect, provided is a compound of the formula (I):

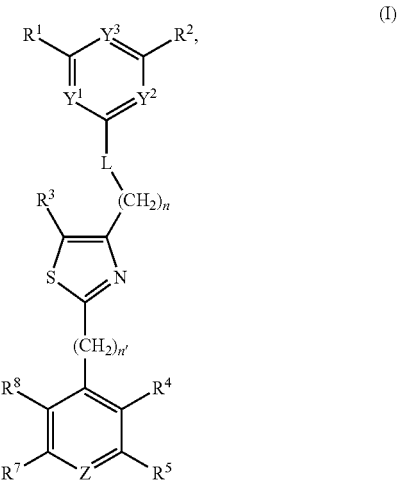

or a salt thereof, wherein:
$R^1$ and $R^2$ are independently H, OH, $OR^{14}$, $NH_2$, $NHC(O)R^{15}$ or $NHC(O)OR^{17}$;
each $Y^1$, $Y^2$ and $Y^3$ is independently N or CH;
L is O, S, SO, $SO_2$, Se, NH or $NR^{16}$;
each m, n, p, q and r is independently 1, 2, 3, 4, 5 or 6;
n' is 0, 1, 2, 3, 4, 5 or 6;
$R^3$ is $C_1$-$C_6$ alkyl, $C_3$-$C_8$ cycloalkyl, aryl, heteroaryl or $OCH_3$;
$R^4$ and $R^8$ are independently H, F, Cl, Br, I, $CF_3$ or $OR^9$;
$R^5$ and $R^7$ are independently H, F, Cl, Br, I, $CF_3$, fluoropyridyl or $OR^{10}$;
Z is N or $CR^6$;
$R^6$ is H, F, Cl, Br, I, $CF_3$ or $OR^{11}$;
$R^9$ and $R^{11}$ are independently $C_1$-$C_6$ alkyl, $C_1$-$C_6$ perfluoroalkyl, $(CH_2)_mX$, $(CH_2)_pOR^{12}$, or $(CH_2)_rX^*$,
$R^{10}$ is $C_1$-$C_6$ alkyl, $C_1$-$C_6$ perfluoroalkyl, $(CH_2)_mX$, $(CH_2)_p$ $OR^{12}$, $(CH_2)_qR^{13}$ or $(CH_2)_rX^*$;
$R^{12}$ is H, tosyl or 2-tetrahydropyranyl;
$R^{13}$ is $OCH_3$, $NH_2$, $NHCOCH_3$, $CO_2H$, $CO_2CH_3$, SH or $COCH_3$;
$R^{14}$ is $C_1$-$C_4$ alkyl;
$R^{15}$ is $C_1$-$C_6$ alkyl or $CF_3$;
$R^{16}$ is $C_1$-$C_4$ alkyl or phenyl;
$R^{17}$ is $C_1$-$C_6$ alkyl;
X is F, Cl, Br or I; and
$X^*$ is $^{18}F$, $^{75}Br$, $^{76}Br$ or $^{124}I$.

In a compound of the formula (I) or a salt thereof, $R^1$ and $R^2$ may be the same of different. In some embodiments, $R^1$ and $R^2$ are independently H, $NH_2$, $NHC(O)R^{15}$ or $NHC(O)$ $OR^{17}$. In one variation, each $R^1$ and $R^2$ is $NH_2$. In another variation, each $R^1$ and $R^2$ is an acylamino group of the formula $NHC(O)R^{15}$, where $R^{15}$ is $CF_3$ or $C_1$-$C_6$ alkyl (e.g., $CH_3$). In one variation, each $R^1$ and $R^2$ is an alkoxycarbonylamino group of the formula $NHC(O)OR^{17}$, where $R^{17}$ is $C_1$-$C_6$ alkyl (e.g., t-butyl). In one variation, one of $R^1$ and $R^2$ is H and the other is $NH_2$. In some embodiments, at least one of $R^1$ and $R^2$ is OH or $OR^{14}$, where $R^{14}$ is $C_1$-$C_4$ alkyl (e.g., $CH_3$ or $C_2H_5$). It is understood and clearly conveyed herein that each and every variation of $R^1$ and $R^2$ described herein may be combined with each and every variation of other variables (e.g., $Y^1$, $Y^2$, $Y^3$, L, Z, n, n', $R^3$, $R^4$, $R^5$, $R^7$ and $R^8$)

described herein, where applicable, as if each and every combination were listed separately.

In some embodiments, at least one of $Y^1$, $Y^2$ and $Y^3$ is N. In some embodiments, $Y^1$ is N. In some embodiments, $Y^2$ is N. In some embodiments, $Y^3$ is N. In one variation, one of $Y^1$, $Y^2$ and $Y^3$ is N and the other two are CH. In a particular variation, $Y^1$ and $Y^2$ are CH and $Y^3$ is N. In one variation, at least two of $Y^1$, $Y^2$ and $Y^3$ are N. In another variation, one of $Y^1$, $Y^2$ and $Y^3$ is CH and the other two are N. In a particular variation, $Y^1$ and $Y^2$ are N and $Y^3$ is CH. In a particular variation, $Y^1$ and $Y^3$ are N and $Y^2$ is CH. In one variation, each $Y^1$, $Y^2$ and $Y^3$ is CH. It is understood and clearly conveyed herein that each and every variation of $Y^1$, $Y^2$ and $Y^3$ described herein may be combined with each and every variation of other variables (e.g., L, Z, n, n', $R^1$, $R^2$, $R^3$, $R^4$, $R^5$, $R^7$ and $R^8$) described herein, where applicable, as if each and every combination were listed separately.

In some embodiments, L is O, S, SO, $SO_2$ or Se. In one embodiment, L is O. In some embodiments, L is S, SO or $SO_2$. In one embodiment, L is S. In some embodiments, L is NH or $NR^{16}$. In some embodiments, L is NH. In some embodiments, L is $NR^{16}$ where $R^{16}$ is $C_1$-$C_4$ alkyl (e.g., $CH_3$) or phenyl. In some of these embodiments, n is an integer from 1 to 6. In one variation, n is 1. In another variation, n is 2, 3, 4, 5, or 6. In some of these embodiments, L is S and n is 1. It is understood and clearly conveyed herein that each and every variation of L and n described herein may be combined with each and every variation of other variables (e.g., $Y^1$, $Y^2$, $Y^3$, Z, n', $R^1$, $R^2$, $R^3$, $R^4$, $R^5$, $R^7$ and $R^8$) described herein, where applicable, as if each and every combination were listed separately.

In some embodiments, $R^3$ is $C_1$-$C_6$ alkyl. In some embodiments, $R^3$ is $C_1$-$C_4$ alkyl (e.g., methyl, ethyl, propyl or butyl). In some embodiments, $R^3$ is $C_3$-$C_8$ cycloalkyl (e.g., cyclohexyl). In some embodiments, $R^3$ is aryl (e.g., phenyl). In some embodiments, $R^3$ is heteroaryl. In one variation, $R^3$ is thiophenyl (e.g., 2-thiophenyl or 3-thiophenyl). In another variation, $R^3$ is furanyl (e.g., 2-furanyl or 3-furanyl). In some embodiments, $R^3$ is $OCH_3$. In some of these embodiments, n' is an integer from 0 to 6. In one variation, n' is 0. In another variation, n' is 1. In another variation, n' is 2, 3, 4, 5, or 6. In some of these embodiments, $R^3$ is methyl, ethyl, propyl or butyl and n' is 0. It is understood and clearly conveyed herein that each and every variation of $R^3$ and n' described herein may be combined with each and every variation of other variables (e.g., $Y^1$, $Y^2$, $Y^3$, L, Z, n, $R^1$, $R^2$, $R^4$, $R^5$, $R^7$ and $R^8$) described herein, where applicable, as if each and every combination were listed separately. For example, in one variation, the compound is of the formula (I), or a salt thereof, wherein each $R^1$ and $R^2$ is $NH_2$, $Y^1$ and $Y^2$ are N, $Y^3$ is CH, L is S, n is 1, n' is 0, $R^3$ is methyl, ethyl, propyl or butyl, $R^5$ is $OR^{10}$ where $R^{10}$ is $(CH_2)_2F$ or $(CH_2)_2OH$, and Z is $CR^6$ where $R^6$ is OMe (i.e., $OCH_3$).

In the compound of the formula (I), or a salt thereof, the moiety comprising the $R^4$, $R^5$, Z, $R^7$ and $R^8$ groups is a substituted phenyl or pyridyl group. In some embodiments, at least one of $R^4$ and $R^8$ is H. In one variation, both $R^4$ and $R^8$ are H. In some embodiments, one of $R^4$ and $R^8$ is F, Cl, Br, I, $CF_3$ or $OR^9$. In one variation, one of $R^4$ and $R^8$ is F. In one particular variation, $R^4$ is F. In another particular variation, $R^8$ is H. In some embodiments, at least one of $R^5$ and $R^7$ is H. In one variation, both $R^5$ and $R^7$ are H. In some embodiments, one of $R^5$ and $R^7$ is F, Cl, Br, I, $CF_3$, a substituted pyridyl such as fluoropyridyl or $OR^{10}$. In some embodiments, $R^5$ is F, Cl, Br, I, $CF_3$, fluoropyridyl or $OR^{10}$. In some embodiments, $R^5$ is F. In some embodiments, $R^5$ is Cl. In some embodiments, $R^5$ is Br. In some embodiments, $R^5$ is I. In some embodiments, $R^5$ is $CF_3$. In some embodiments, $R^5$ is fluoropyridyl (e.g., 4-fluoro-3-pyridyl). In some embodiments, $R^5$ is $OR^{10}$, where $R^{10}$ is $C_1$-$C_6$ alkyl, $C_1$-$C_6$ perfluoroalkyl, $(CH_2)_mX$, $(CH_2)_pOR^{12}$, $(CH_2)_qR^{13}$ or $(CH_2)_rX^*$. In one variation, $R^{10}$ is $(CH_2)_qR^{13}$ where q is 1, 2, 3, 4, 5 or 6 and $R^{13}$ is $OCH_3$, $NH_2$, $NHCOCH_3$, $CO_2H$, $CO_2CH_3$, SH or $COCH_3$. In one particular variation, q is 2. In one variation, $R^{13}$ is $OCH_3$. In another variation, $R^{13}$ is $NH_2$ or $NHCOCH_3$. In another variation, $R^{13}$ is $CO_2H$ or $CO_2CH_3$. In another variation, $R^{13}$ is SH. In another variation, $R^{13}$ is $COCH_3$. In one variation, $R^{10}$ is $C_1$-$C_6$ alkyl, $C_1$-$C_6$ perfluoroalkyl, $(CH_2)_mX$, $(CH_2)_pOR^{12}$ or $(CH_2)_rX^*$. In one variation, $R^{10}$ is $C_1$-$C_6$ alkyl (e.g., $CH_3$, $C_2H_5$, $C_3H_7$, $C_4H_9$, $C_5H_{11}$ and $C_6H_{13}$) or $C_1$-$C_6$ perfluoroalkyl (e.g., $CF_3$, $C_2F_5$, $C_3F_7$, $C_4F_9$, $C_5F_{11}$ and $C_6F_{13}$). In one variation, $R^{10}$ is $(CH_2)_mX$ where m is 1, 2, 3, 4, 5 or 6 and X is F, Cl, Br or I. In one particular variation, m is 2. In another particular variation, wherein X is F. In one variation, X is Cl, Br or I. In a specific variation, m is 2 and X is F (i.e., $R^{10}$ is $CH_2CH_2F$, or $R^5$ is $OCH_2CH_2F$). In one variation, $R^{10}$ is $(CH_2)_pOR^{12}$ where p is 1, 2, 3, 4, 5 or 6 and $R^{12}$ is H, tosyl or 2-tetrahydropyranyl. In one particular variation, p is 2. In another particular variation, $R^{12}$ is H. In another particular variation, $R^{12}$ is tosyl (toluenesulfonyl, e.g., p-toluenesulfonyl). In another particular variation, $R^{12}$ is 2-tetrahydropyranyl. In a specific variation, p is 2 and X is OH (i.e., $R^{10}$ is $CH_2CH_2OH$, or $R^5$ is $OCH_2CH_2OH$). In one variation, $R^{10}$ is $(CH_2)_rX^*$ where r is 1, 2, 3, 4, 5 or 6 and $X^*$ is a radioactive isotope such as $^{18}F$, $^{75}Br$, $^{76}Br$ or $^{124}I$. In one particular variation, m is 2. In another particular variation, $X^*$ is $^{18}F$. In another variation, $X^*$ is $^{75}Br$, $^{76}Br$ or $^{124}I$. In some embodiments, $R^7$ is H. In some embodiments, Z is $CR^6$ where $R^6$ is H, F, Cl, Br, I, $CF_3$ or $OR^{11}$. In one variation, $R^6$ is H. In another variation, $R^6$ is F. In another variation, $R^6$ is Cl, Br or I. In another variation, $R^6$ is $CF_3$. In one variation, $R^6$ is $OR^{11}$ where $R^{11}$ is $C_1$-$C_6$ alkyl, $C_1$-$C_6$ perfluoroalkyl, $(CH_2)_mX$, $(CH_2)_pOR^{12}$, or $(CH_2)_rX^*$. In one variation, $R^{11}$ is $C_1$-$C_6$ alkyl (e.g., $CH_3$, $C_2H_5$, $C_3H_7$, $C_4H_9$, $C_5H_{11}$ and $C_6H_{13}$) or $C_1$-$C_6$ perfluoroalkyl (e.g., $CF_3$, $C_2F_5$, $C_3F_7$, $C_4F_9$, $C_5F_{11}$ and $C_6F_{13}$). In a specific variation, $R^{11}$ is $CH_3$ (i.e., $R^6$ is $OCH_3$ or OMe). In another variation, $R^{11}$ is $(CH_2)_pOR^{12}$ where $R^{12}$ is H, tosyl or 2-tetrahydropyranyl. In another specific variation, $R^{11}$ is $(CH_2)_2OH$ (i.e., $R^6$ is $OCH_2CH_2OH$). In another variation, $R^{11}$ is $(CH_2)_mX$ where m is 1, 2, 3, 4, 5 or 6 and X is F, Cl, Br or I. In another specific variation, $R^{11}$ is $(CH_2)_2F$ (i.e., $R^6$ is $OCH_2CH_2F$). In another variation, $R^{11}$ is $(CH_2)_rX^*$ where r is 1, 2, 3, 4, 5 or 6 and $X^*$ is a radioactive isotope such as $^{18}F$, $^{75}Br$, $^{76}Br$ or $^{124}I$. In another specific variation, $R^{11}$ is $(CH_2)_2$$^{19}F$ (i.e., $R^6$ is $OCH_2CH_2$$^{19}F$). In some embodiments, Z is N. In some embodiments, $R^4$, $R^7$ and $R^8$ are H, $R^5$ is $OCH_2CH_2F$ or $OCH_2CH_2OH$, and Z is $CR^6$ where $R^6$ is OMe. It is understood and clearly conveyed herein that each and every variation of $R^4$, $R^5$, Z, $R^7$ and $R^8$ described herein may be combined with each and every variation of other variables (e.g., $Y^1$, $Y^2$, $Y^3$, L, Z, n, n', $R^1$, $R^2$, and $R^3$) described herein, where applicable, as if each and every combination were listed separately. For example, in one variation, the compound is of the formula (I), or a salt thereof, wherein each $R^1$ and $R^2$ is $NH_2$, $Y^1$ and $Y^2$ are N, $Y^3$ is CH, L is S, n is 1, n' is 0, $R^3$ is methyl, ethyl or propyl, $R^4$, $R^7$ and $R^8$ are H, $R^5$ is $OCH_2CH_2F$ or $OCH_2CH_2OH$, and Z is $CR^6$ where $R^6$ is OMe.

In some embodiments, provided is a compound of the formula (A):

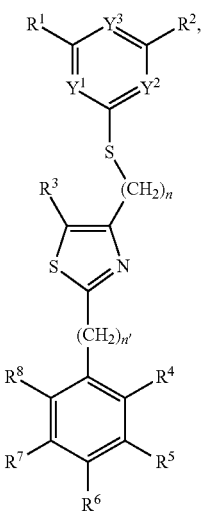

or a salt thereof, wherein:

$R^1$ and $R^2$ are independently $NH_2$, $OH$, $OCH_3$ or $OC_2H_5$;

each $Y^1$, $Y^2$ and $Y^3$ is independently N or CH;

n is 1, 2, 3, 4, 5 or 6;

n' is 0, 1, 2, 3, 4, 5 or 6;

$R^3$ is $CH_3$, $C_2H_5$, $C_3H_7$ or $OCH_3$;

each $R^4$, $R^5$, $R^6$, $R^7$ and $R^8$ is independently H, F, Cl, Br, I or $OR^9$;

each $R^9$ is independently $CH_3$, $C_2H_5$, $C_3H_7$, $C_4H_9$, $C_5H_{11}$, $C_6H_{13}$, $CH_2F$, $C_2H_4F$, $C_3H_6F$, $C_4H_8F$, $C_5H_{10}F$, $C_6H_{12}F$, $C_2H_4Br$, $C_2H_4I$, $CF_3$, $C_2F_5$, $C_3F_7$, $C_4F_9$, $C_5F_{11}$, $C_6F_{13}$; $CH_2OTs$, $C_2H_4OTs$, $C_3H_6OTs$, $C_4H_8OTs$, $C_5H_{10}OTs$, $C_6H_{12}OTs$, wherein Ts is tosyl; $CH_2OH$, $C_2H_4OH$, $C_3H_6OH$, $C_4H_8OH$, $C_5H_{10}OH$, $C_6H_{12}OH$; $CH_2OTHP$, $C_2H_4OTHP$, $C_3H_6OTHP$, $C_4H_8OTHP$, $C_5H_{10}OTHP$ or $C_6H_{12}OTHP$, wherein THP is 2-tetrahydropyranyl group; and $CH_2X^*$, $C_2H_4X^*$, $C_3H_6X^*$, $C_4H_8X^*$, $C_5H_{10}X^*$, $C_6H_{12}X^*$, wherein $X^*$ is selected from: $^{18}F$, $^{75}Br$, $^{76}Br$ or $^{124}I$.

In some embodiments, a salt of a compound of the formula (I) or (A) is a salt formed with an organic acid such as acetic acid, trifluoroacetic acid, p-toluenesulfonic acid, methanesulfonic acid, citric acid, and the like; or an inorganic acid such as hydrofluoric acid, hydrochloric acid, hydrobromic acid, hydroiodic acid, nitric acid, sulfuric acid, phosphoric acid, and the like. In one variation, the salt of a compound of the formula (I) or (A) is formed with an acid of the formula H—W, wherein W is selected from the group consisting of F, Cl, Br, I, $NO_3$, $HSO_4$ and $H_2PO_4$.

In some embodiments, the compound is

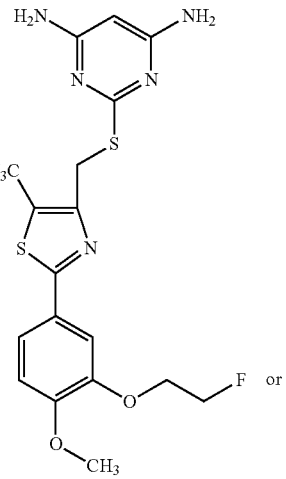

DI-F2.2.1

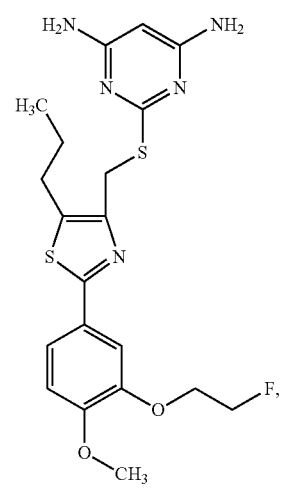

DI-F2.3.1 or a salt thereof.

In some embodiments, provided is a compound of the formula (I), or a salt thereof, wherein:

$R^1$ and $R^2$ are $NH_2$;

each $Y^1$, $Y^2$ and $Y^3$ is independently N or CH;

L is O, S, SO, $SO_2$, Se, NH or $NR^{16}$;

each m, n, p and q is independently 1, 2, 3, 4, 5 or 6;

n' is 0;

$R^3$ is methyl, ethyl, propyl, butyl, cyclohexyl, phenyl, thiophenyl or furanyl;

Z is N or $CR^6$;

each of $R^4$, $R^6$, $R^7$ and $R^8$ is independently H, F, $CF_3$ or $OCH_3$; provided that no more than one of $R^4$, $R^6$, $R^7$ and $R^8$ is F, $CF_3$ or $OCH_3$;

$R^5$ is $OR^{10}$;

$R^{10}$ is $(CH_2)_mX$, $(CH_2)_pOH$ or $(CH_2)_qR^{13}$;

$R^{13}$ is $OCH_3$, $NH_2$, $NHCOCH_3$, $CO_2H$, $CO_2CH_3$, SH or $COCH_3$;

$R^{16}$ is methyl, ethyl, propyl, butyl or phenyl; and

X is F, Cl, Br or I.

In some embodiments, provided is a compound selected from the group consisting of:
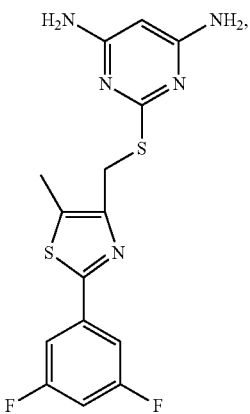 DI-01
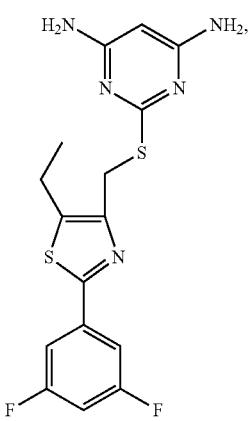 DI-02
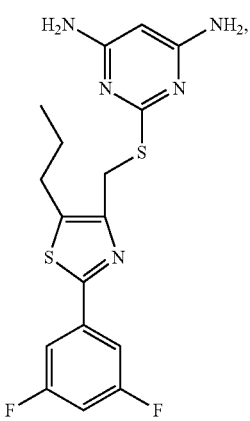 DI-03
-continued
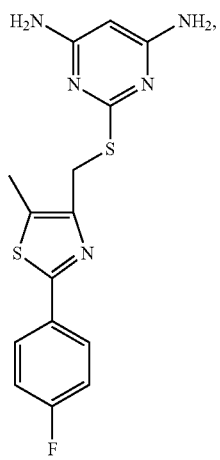 DI-04
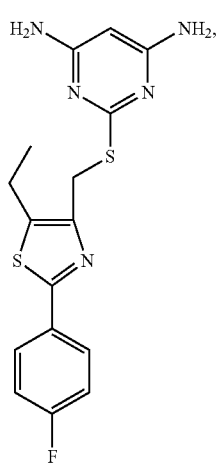 DI-05
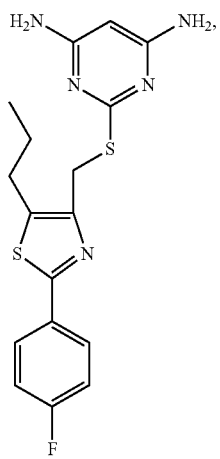 DI-06

-continued
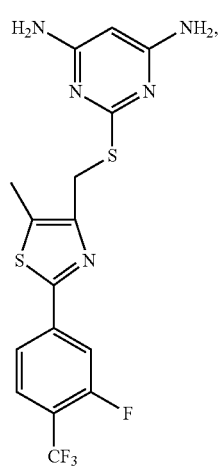
DI-07
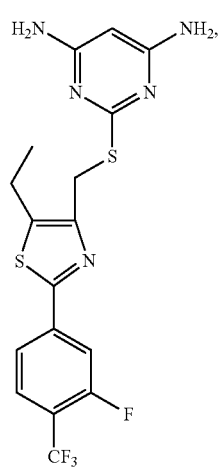
DI-08
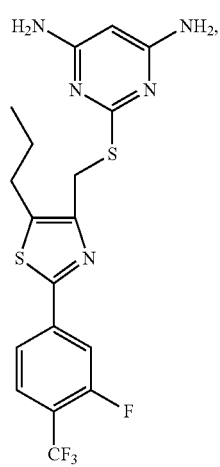
DI-09
-continued
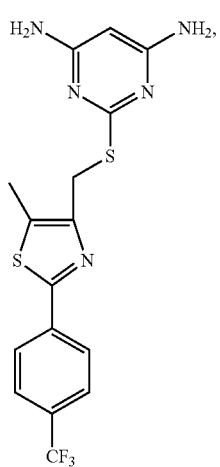
DI-10
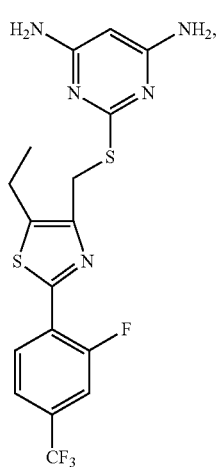
DI-11
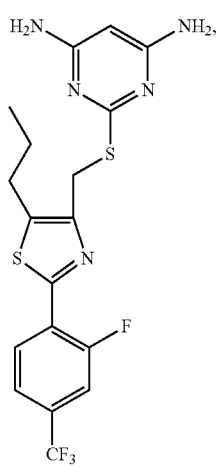
DI-12

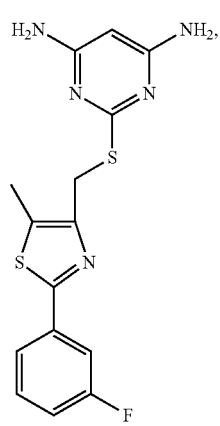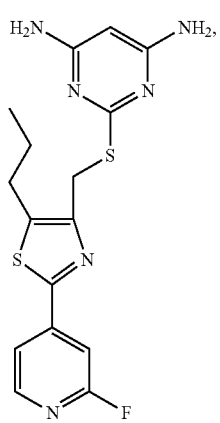

-continued
DI-20
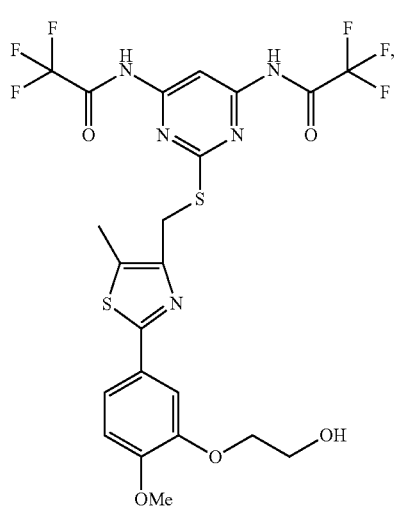
DI-23
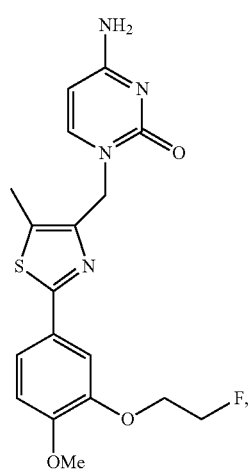
DI-22
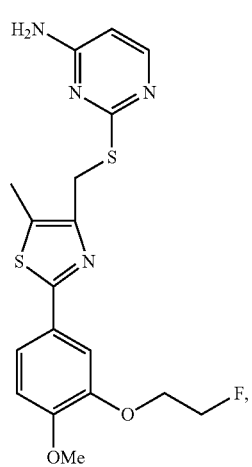
-continued
DI-24
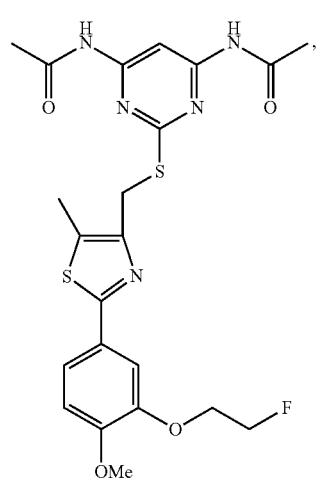
DI-25
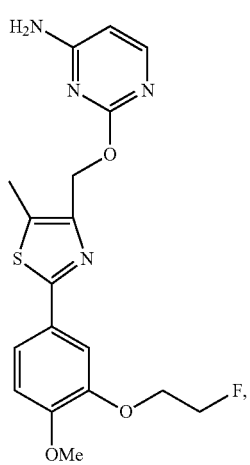
DI-26
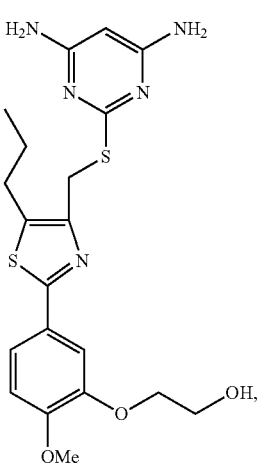

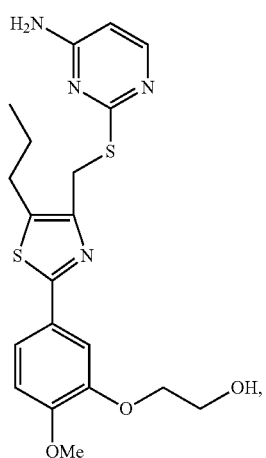
DI-27
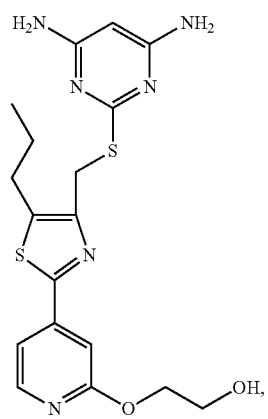
DI-30
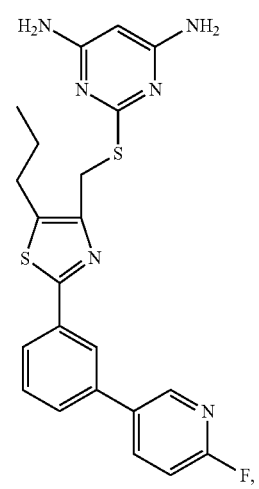
DI-28
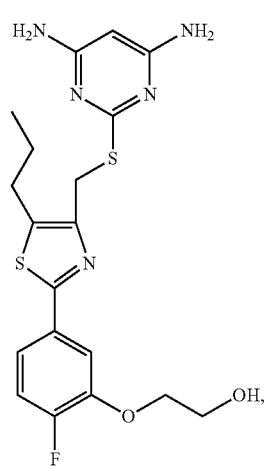
DI-31
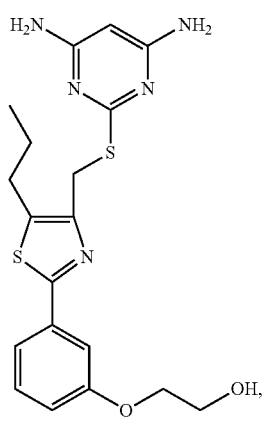
DI-29
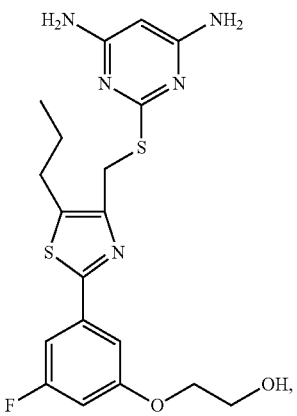
DI-32

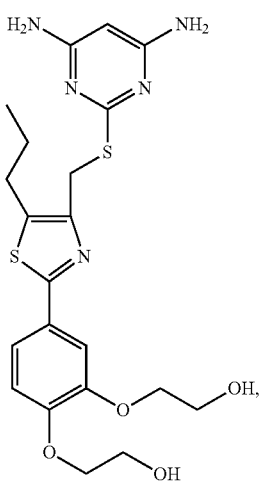

DI-33

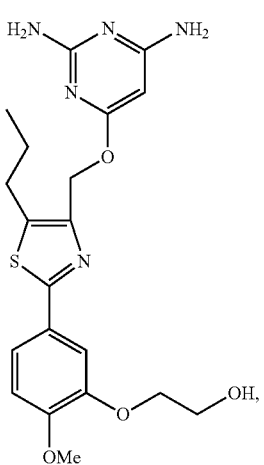

DI-34

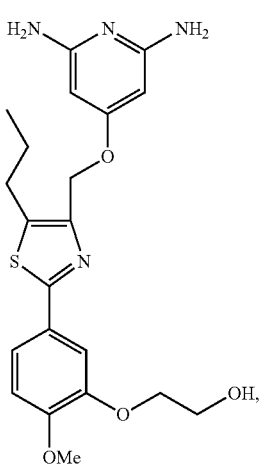

DI-35

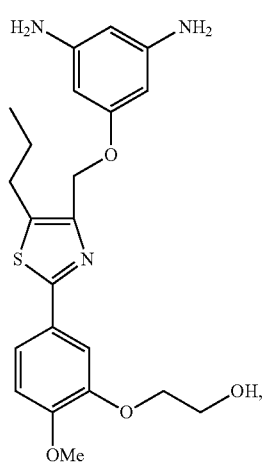

DI-36

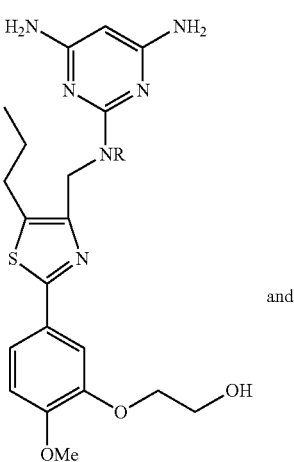

DI-37

R = H, Me, Et, Pr, Bu, Ph

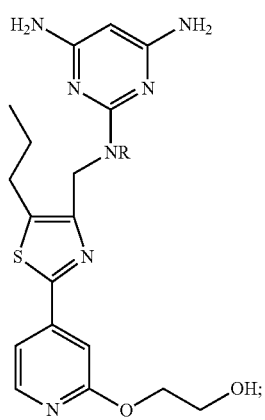

DI-38

R = H, Me, Et, Pr, Bu, Ph or salt thereof.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Supplemental Compounds

Additional compounds described herein include compounds DI-0105, DI-0110 and DI-0120, which may be synthesized using synthetic methods described herein or other methods known in the art.

DI-0105
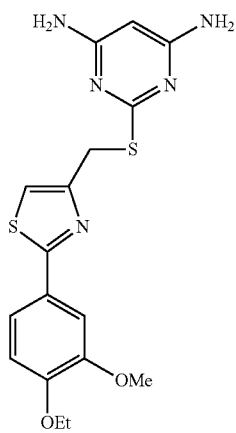

DI-0110
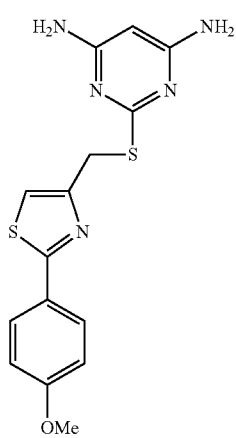

-continued

DI-0120
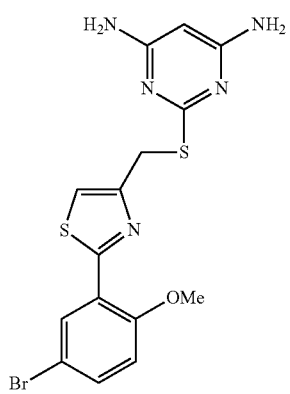

Other compounds are also described herein:

DI-0103
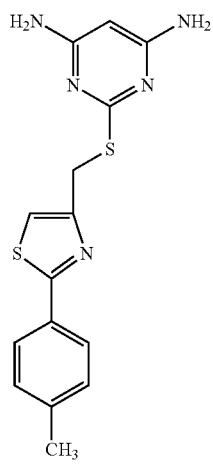

DI-0104
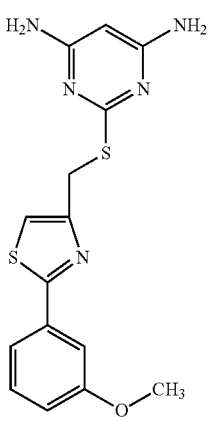

-continued
DI-0106
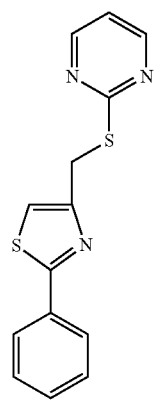
DI-0107
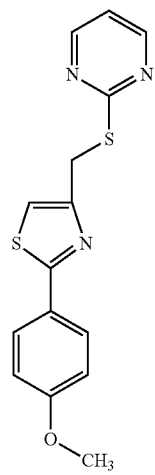
DI-C1.1.2
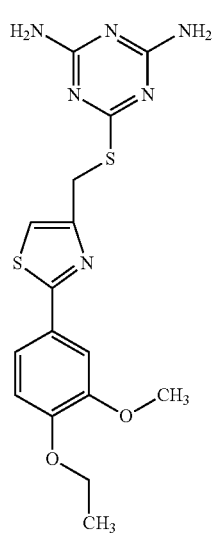
-continued
DI-C6.1.1
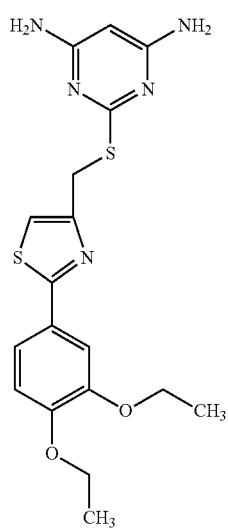
DI-F1.1.1
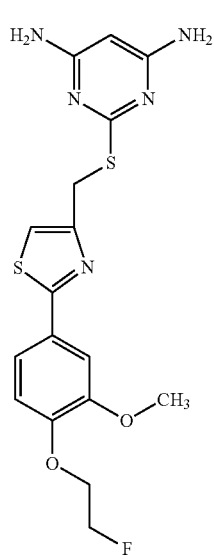
DI-F1.1.2
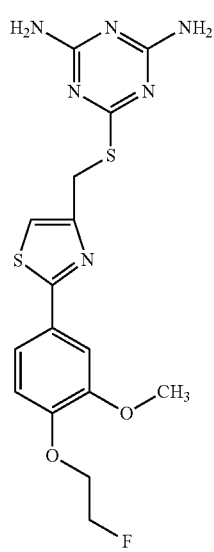

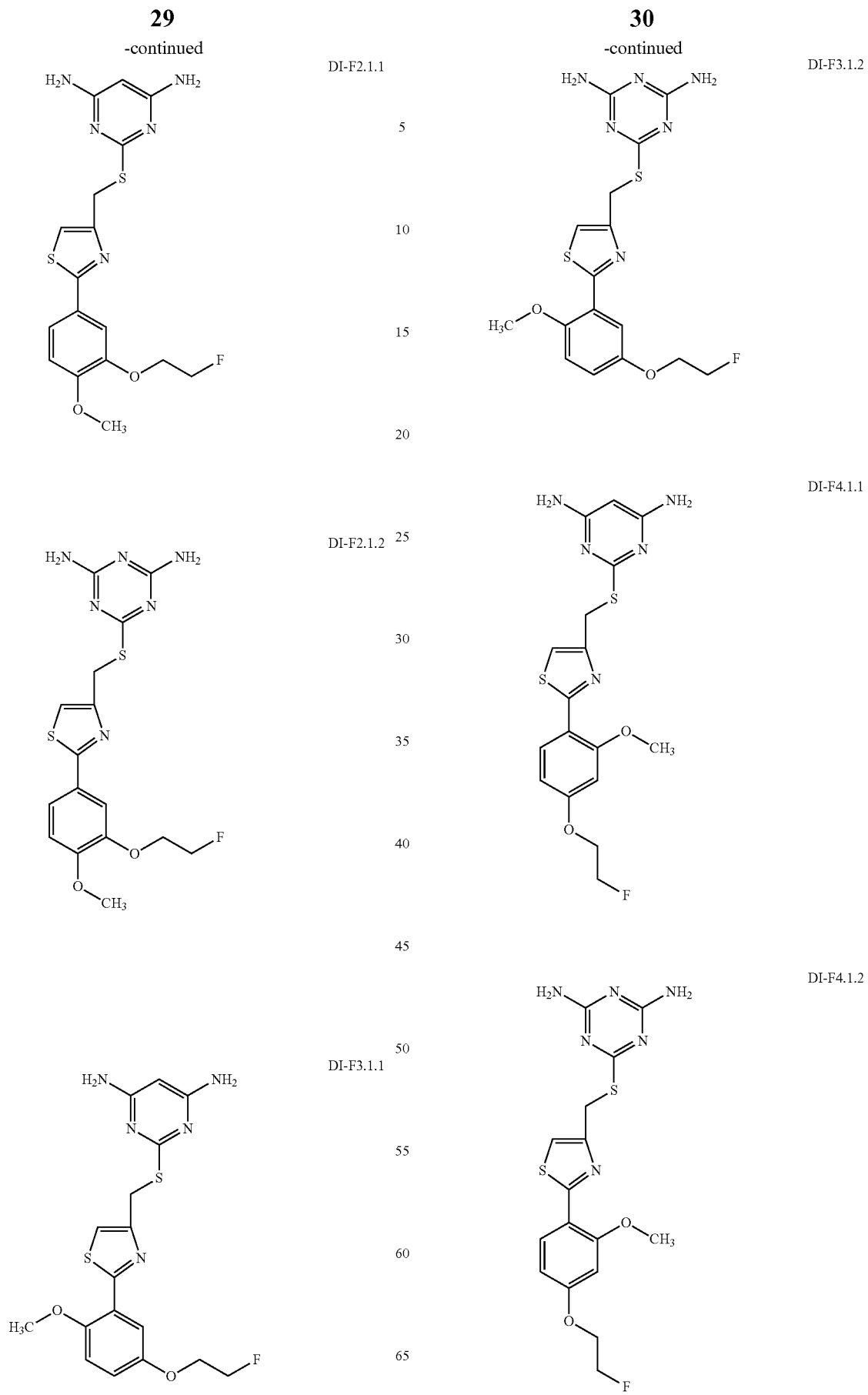

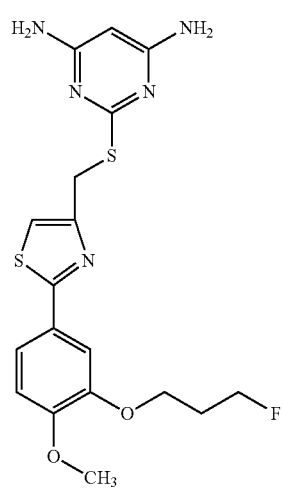
DI-F5.1.1
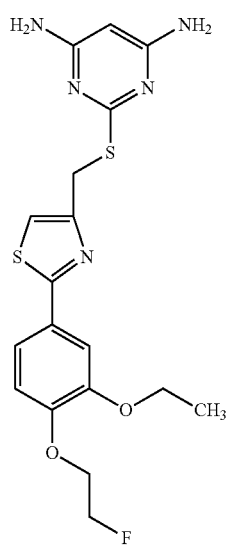
DI-F7.1.1
DI-F5.1.2
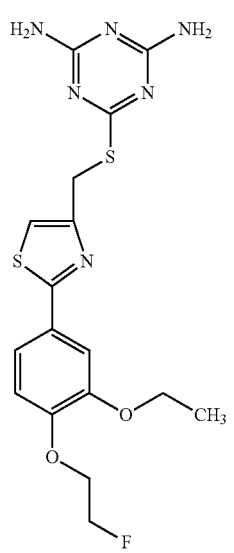
DI-F7.1.2
DI-F6.1.1
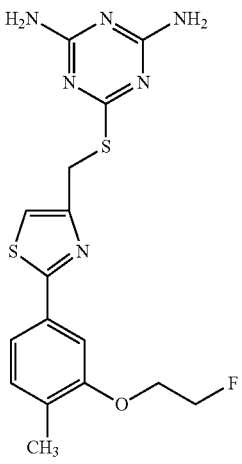
DI-F11.1.2

DI-F11.1.1

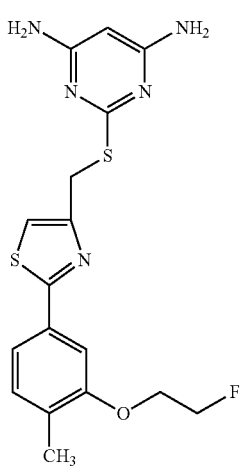

DI-F2.1a.1

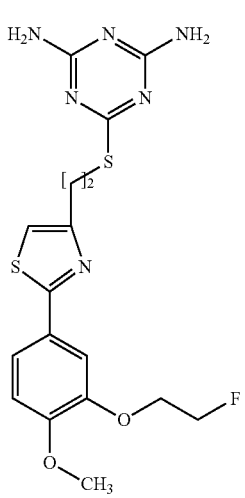

DI-F2a.1.1

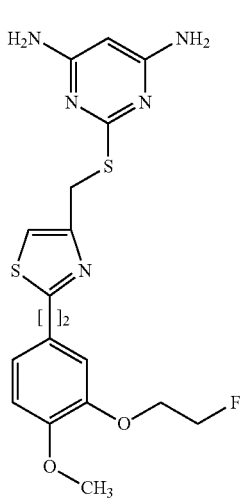

DI-F2.3.1

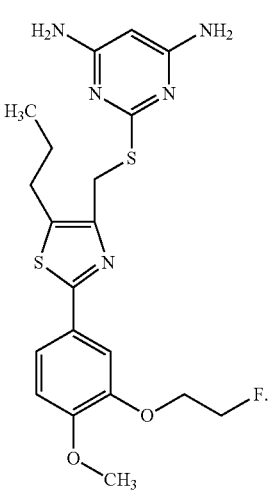

Methods of Treatment

Compounds provided herein bind to a deoxycytidine kinase polypeptide and inhibit its activity. Thus in another aspect, provided are methods for inhibiting dCK activity and treating diseases and disorders where dCK activity is implicated.

Potency of dCK inhibitory activities of the compounds can be tested by measuring cellular substrate uptake and phosphorylation, for examples, uptake of [$^3$H]-deoxycytidine (dCyd or dC) into CEM (human) or L1210 (mouse) cells. The compounds may be further screened for low off-target toxicity (e.g., inhibition of growth and proliferation of dCK negative cells) and selectivity over other nucleoside kinases (e.g., thymidine kinase).

In some embodiments, provided is a method for inhibiting a deoxycytidine kinase (dCK) activity comprising contacting a compound detailed herein (e.g., a compound of the formula (I) or (A), or any variations thereof, such as compound DI-F2.2.1 or DI-26) with the dexoycytidine kinase, either in vitro (e.g., in an enzymatic or an cell based assay setting) or in vivo (e.g., in animal models or an individual subject in need of treatment).

In some embodiments, provided is a method for treating cancer in an individual comprising administering to the individual an effective amount of a compound detailed herein (e.g., a compound of the formula (I) or (A), or any variations thereof, such as compound DI-F2.2.1 or DI-26), or a pharmaceutically acceptable salt thereof, and thymidine. The compound is administered in conjunction with thymidine. In some embodiments, the compound is administered before, during or after administration of thymidine. Examples of cancer treated include, but is not limited to leukemia, lymphoma, breast cancer, ovarian cancer, lung cancer, pancreatic cancer, hepatocellular carcinoma, melanoma, sarcoma, head and neck cancer, glioma, glioblastoma, and a cancer independent of tissue of origin that are characterized by genomic instability and/or activation of the DNA damage response. Inhibition of dCK by a compound detailed herein (e.g., a compound of the formula (I) or (A), or any variations thereof, such as compound DI-F2.2.1 or DI-26), or a pharmaceutically acceptable salt thereof, synergizes with thymidine to induce cell cycle arrest in tumors.

Without wishing to be bound by theory, the invention uses pharmacological approaches to induce nucleotide insufficiency in highly proliferative tumors in order to block their proliferation by arresting them in the S-phase of cell cycle.

For example, deoxycytidine triphosphate (dCTP) pools are depleted by thymidine combined with deoxycytidine kinase (dCK) inhibitors (see FIG. 2). The function of thymidine is to block the ability of ribonucleotide reductase (RR), the rate limiting enzyme in deoxyribonucleotide synthesis, to produce deoxycytidine triphosphate (dCTP), one of the 4 building blocks of DNA. The only other way of generating dCTP in cancer cells is by recycling preformed deoxycytidine from the extracellular environment; deoxycytidine kinase is essential for the recycling process; small molecule inhibitors such as F2.2.1, DI-26 and related compounds block dCK activity and, in combination with thymidine, starve cancer cells of dCTP, thus preventing their proliferation.

In some embodiments, provided is a method for treating an immune disorder in an individual in need thereof comprising administering to the individual an effective amount of a compound detailed herein (e.g., a compound of the formula (I) or (A), or any variations thereof, such as compound DI-F2.2.1 or DI-26), or a pharmaceutically acceptable salt thereof. The immune disorder may be an autoimmune disorder or transplant rejection. In some embodiments, the autoimmune disorder is a T cell mediated autoimmune disorder. In some embodiments, the autoimmune disorder is selected from the group consisting of multiple sclerosis, lupus (including systemic lupus erythematosus), inflammatory bowel disease, rheumatoid arthritis and type 1 diabetes.

Also provided are compositions, such as pharmaceutical compositions, comprising a compound detailed herein, or a salt thereof, and a pharmaceutically acceptable carrier. Pharmaceutical compositions according to the invention may take a form suitable for oral, buccal, parenteral, nasal, topical or rectal administration, or a form suitable for administration by injection, i.v. infusion or inhalation.

The compounds described herein (e.g., any compound of formula (I) or any variations thereof), as well as methods of using the same, unless otherwise stated, include all salt forms of the compounds. The compounds also include all non-salt forms of any salt of a compound described herein, as well as other salts of any salt of a compound described herein. In some embodiments, the salts of the compounds are pharmaceutically acceptable salts. The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts. Examples of inorganic salts of base compounds include, but are not limited to, hydrofluoride, hydrochloride, hydrobromide, hydroiodie, sulfate, hydrogen sulfate, phosphate, hydrogen phosphate, dihydrogen phosphate, carbonate, bicarbonate, and nitrate salts. Examples of organic salts of base compounds include, but are not limited to, tartrate, citrate, maleate, fumarate, and succinate.

PET Probe and Imaging

Some PET probes have been previously disclosed, for example, the [$^{18}$F]-FAC and [$^{18}$F]-FMAC PET probes, which binds dCK, were described in U.S. patent application Ser. No. 12/234,478 (issued as U.S. Pat. No. 8,101,740), the contents of which are incorporated herein by reference.

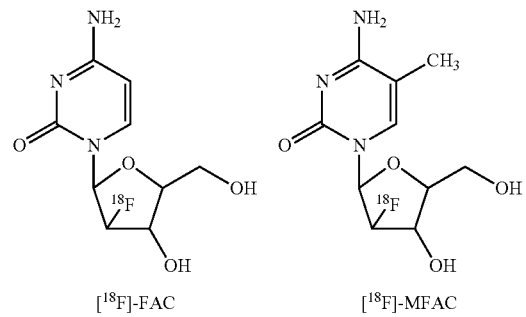

[$^{18}$F]-FAC      [$^{18}$F]-MFAC

Provided herein is a PET probe comprising a compound of the formula (A):

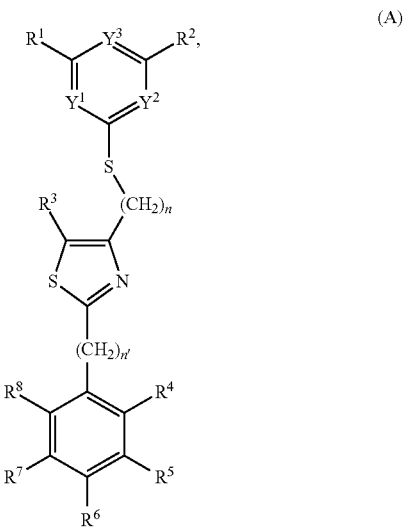

(A)

or a salt thereof, wherein:

$R^1$ and $R^2$ are independently $NH_2$, OH, $OCH_3$ or $OC_2H_5$;
each $Y^1$, $Y^2$ and $Y^3$ is independently N or CH;
n is 1, 2, 3, 4, 5 or 6;
n' is 0, 1, 2, 3, 4, 5 or 6;
$R^3$ is H, $CH_3$, $C_2H_5$, $C_3H_7$ or $OCH_3$;
each $R^4$, $R^5$, $R^6$, $R^7$ and $R^8$ is independently H, F, Cl, Br, I or $OR^9$;
each $R^9$ is independently $CH_3$, $C_2H_5$, $C_3H_7$, $C_4H_9$, $C_5H_{11}$, $C_6H_{13}$, $CH_2F$, $C_2H_4F$, $C_3H_6F$, $C_4H_8F$, $C_5H_{10}F$, $C_6H_{12}F$, $C_2H_4Br$, $C_2H_4I$, $CF_3$, $C_2F_5$, $C_3F_7$, $C_4F_9$, $C_5F_{11}$, $C_6F_{13}$; $CH_2OTs$, $C_2H_4OTs$, $C_3H_6OTs$, $C_4H_8OTs$, $C_5H_{10}OTs$, $C_6H_{12}OTs$, wherein Ts is tosyl; $CH_2OH$, $C_2H_4OH$, $C_3H_6OH$, $C_4H_8OH$, $C_5H_{10}OH$, $C_6H_{12}OH$; $CH_2OTHP$, $C_2H_4OTHP$, $C_3H_6OTHP$, $C_4H_8OTHP$, $C_5H_{10}OTHP$ or $C_6H_{12}OTHP$, wherein THP is 2-tetrahydropyranyl group; and $CH_2X^*$, $C_2H_4X^*$, $C_3H_6X^*$, $C_4H_8X^*$, $C_5H_{10}X^*$, $C_6H_{12}X^*$, wherein $X^*$ is selected from: $^{18}$F, $^{75}$Br, $^{76}$Br or $^{124}$I;

provided that at least one of $R^4$, $R^5$, $R^6$, $R^7$ and $R^8$ contains $X^*$.

The compounds provided herein are amenable to introduction of a radio isotope suitable of PET imaging, such as fluorine-18, in the last synthetic step. In some embodiments, the compound is DI-F2.2.1:

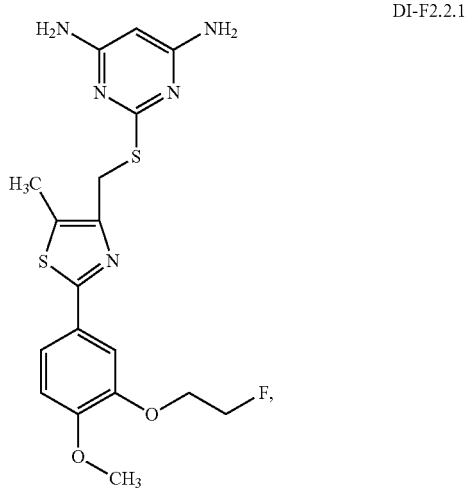 [SMILES: COc1ccc(-c2nc(CSc3nc(N)cc(N)n3)c(C)s2)cc1OCCF]

DI-F2.2.1 or a salt thereof, where the fluorine atom is enriched in $^{18}$F relative to its natural abundance.

Also provided is a method of imaging, comprising: contacting a PET probe detailed herein with a biological material; using PET imaging to determine a local concentration of the compound in the biological material; and correlating the local concentration of the compound with a local immune response or the presence of neoplastic tissue. In some embodiments, contacting the compound with a biological material comprises administering a quantity of the compound to an animal or human; and correlating the local concentration of the compound in the animal or human with a local immune response or neoplastic tissue in the animal or human. In some embodiments, the method further comprising using the local concentration of the compound to diagnose cancer and/or monitor cancer treatment. In some embodiments, the animal or human has a condition selected from the group consisting of cancer, an autoimmune disorder, a development disorder, viral infection, bacterial infection, parasitical infection, infection, a metabolic disease, and inflammation. In some embodiments, the animal or human has a condition selected from the group consisting of lymphadenopathy, melanoma, leukemia, and glioma. In some embodiments, the animal or human has a condition selected from the group consisting of rheumatoid arthritis, inflammatory bowel disease, Experimental Autoimmune Encephalomyelitis (EAE), multiple sclerosis, type 1 diabetes, and atherosclerosis. In some embodiments, the animal or human is undergoing a therapy selected from the group consisting of cancer immunotherapy, immunotherapy, interferon therapy, vaccination, radiation therapy, chemotherapy, and antibiotic therapy. In some embodiments, contacting the compound with a biological material comprises administering a quantity of the compound to an animal or human; and correlating the local concentration of the compound in the animal or human with abnormal activity in an organ or portion of the lymphatic system, for example, a lymph node or the spleen. In one variation, the method further comprises correlating the local concentration of the compound with a lymphoma lesion or a malignant lymphoid disease. In some embodiments, the local immune response is the accumulation of activated T lymphocytes. In one variation, the activated T lymphocytes take up more compound per cell than non-activated T lymphocytes.

Also provided is a method of predicting resistance to an oncolytic agent, comprising: contacting a PET probe detailed herein with a neoplasm; using PET imaging to determine a local concentration of the compound in the neoplasm; comparing the local concentration of the compound with a baseline level; correlating a local concentration of the compound substantially lower than the baseline level with low dCK expression of the neoplasm; correlating low dCK expression of the neoplasm with oncolytic nucleoside analog resistance, wherein the baseline level corresponds to a measured concentration of the compound in representative neoplastic cells that express dCK, concentration of the compound in representative neoplastic cells that do not express dCK, or a weighted average. In some embodiments, the neoplasm is of the T lymphocyte lineage. In some embodiments, the neoplasm is selected from the group consisting of leukemia, acute non-lymphocytic leukemia, acute lymphocytic leukemia, blast phase of chronic myelocytic leukemia, meningeal leukemia, pancreatic cancer, ovarian cancer, breast cancer, non-small cell lung cancer, B-cell chronic lymphocytic leukemia, hairy cell leukemia, relapsed acute lymphoblastic leukemia, and refractory acute lymphoblastic leukemia cells.

Further provided is a method for examining the use of a compound in a PET process, the method comprising the steps:

a) incorporating a "cold" fluorine 19 atom at a defined position in the compound of a PET probe detailed herein;

b) substituting the "cold" fluorine 19 atom with a "hot" fluorine 18 atom;

c) administering the compound of step (b) to a mammal; and d) detecting and/or quantifying the compound of step (b) throughout the body of the mammal with PET imaging.

In some embodiments, the method further comprises the steps of:

e) building a kinetic model of drug biodistribution in vivo with the PET data; and f) repeating steps (a) through (e) to further modify and improve the PK of compounds identified by PET imaging to have unfavorable biodistribution in mice and/or humans.

Also provided is a method for evaluating efficacy of a dCK inhibitor compound, comprising: administering a dCK inhibitor compound to an individual; providing an $^{18}$F-FAC PET probe to the individual; imaging to determine a local concentration of the $^{18}$F-FAC PET probe; and correlating the local concentration of the $^{18}$F-FAC PET probe with efficacy of the dCK inhibitor compound. In some embodiments, the individual is a mammal, such as an experimental mouse used in an animal model for testing dCK inhibition. The method provides an efficient way of screening for in vivo efficacy of compounds in animal models. The method may be applied to any dCK inhibitors such as the dCK inhibitor compounds detailed herein, or a pharmaceutically acceptable salt thereof.

General Synthetic Methods

Compounds of the formula (I) may be synthesize according to Schemes 1, 2 and 3, and/or using methods known in the art.

Scheme 1
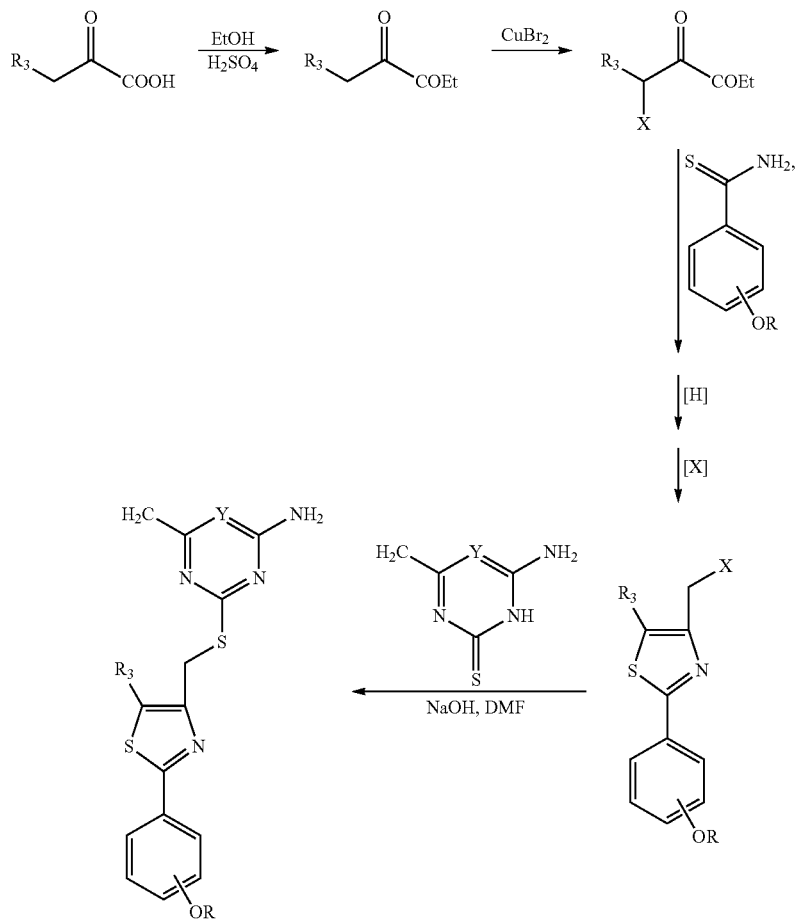
wherein the OR group may be attached to the 2-, 3-, or 4-position of the phenyl ring; R and $R_3$ may be alkyl, fluoro-alkyl, tetrahydro-2H-pyran-protected alkyl, alkoxy or tosyl-protected alkyl groups; and Y is N or CH.
Scheme 2
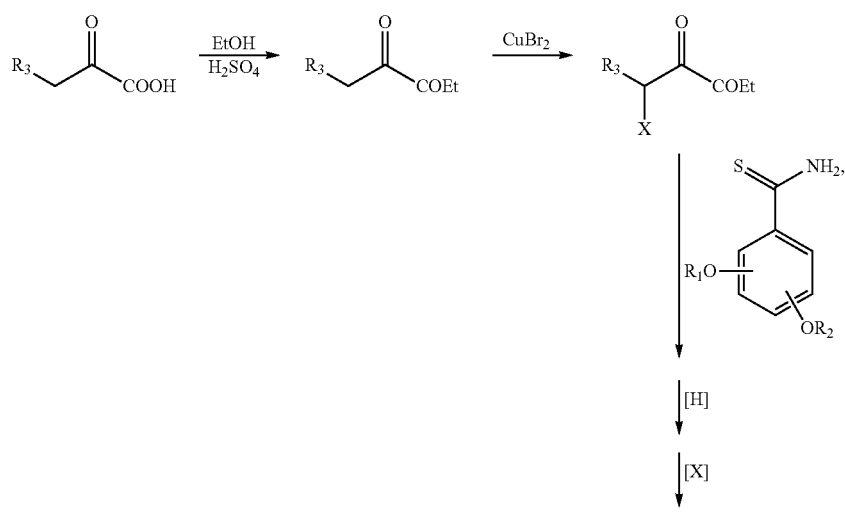

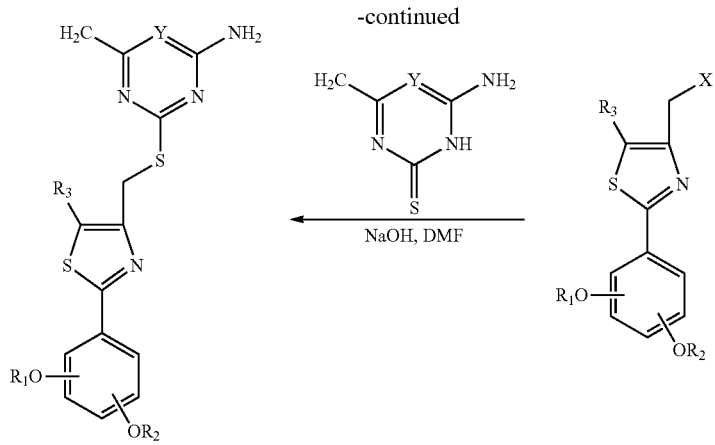
wherein the $OR_1$ and $OR_2$ groups may be attached to the 2,3-, 2,4-, 2,5-, 2,6-, 3,4- or 3,5-positions of the phenyl ring; the $R_1$, $R_2$ and $R_3$ groups may be independently alkyl, fluoro-alkyl, tetrahydro-2H-pyran-protected alkyl, alkoxy or tosyl-protected alkyl groups; and Y is N or CH.
Scheme 3
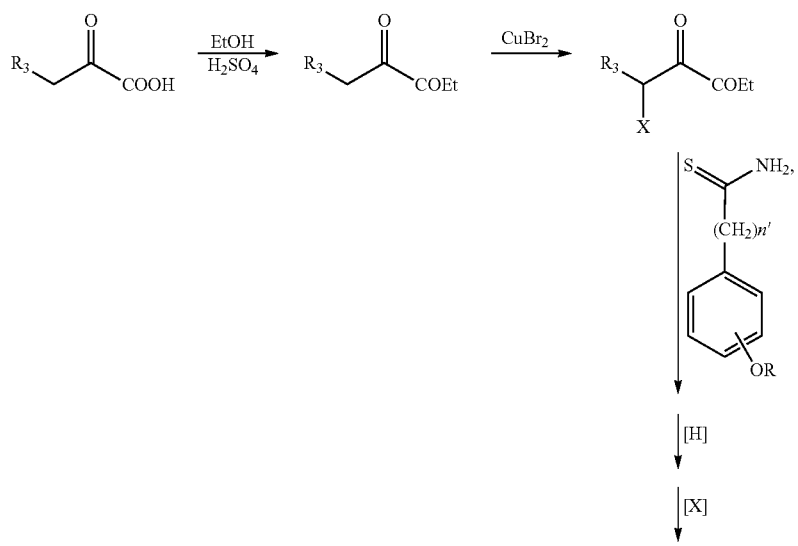
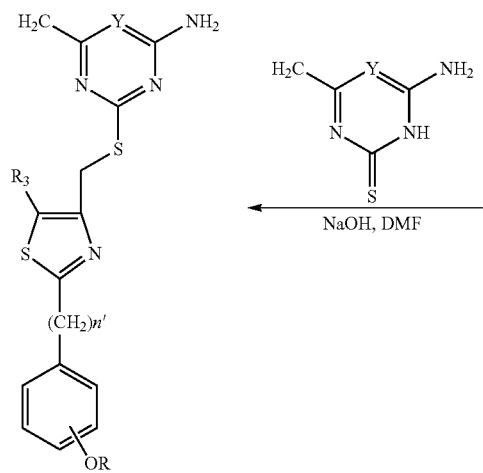

wherein the OR group may be attached to the 2-, 3-, or 4-position of the phenyl ring; R and $R_3$ may be alkyl, fluoro-alkyl, tetrahydro-2H-pyran-protected alkyl, alkoxy or tosyl-protected alkyl groups; and Y is N or CH.

Radioactive labeling of compounds for the PET probes may be carried out according to Schemes 4 and 5, and/or using methods known in the art.

Scheme 4

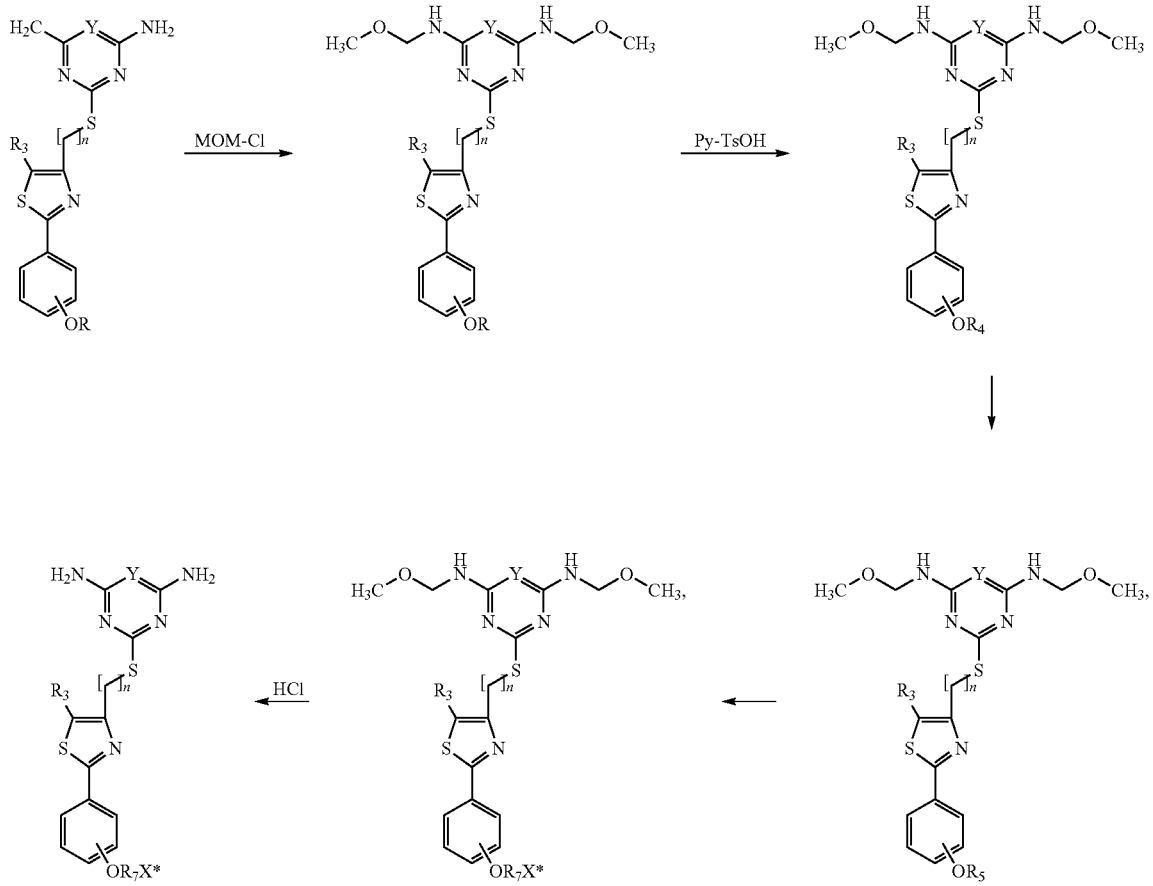

wherein the OR group may be attached to the 2, 3, or 4-position of the phenyl ring; X* may be $^{18}F$, $^{75}Br$, $^{76}Br$ or $^{124}I$; R and $R_{3-8}$ may be independently alkyl, fluoro-alkyl, tetrahydro-2H-pyran-protected alkyl, alkoxy or tosyl-protected alkyl groups; n=1-6; and Y is N or CH.

Scheme 5

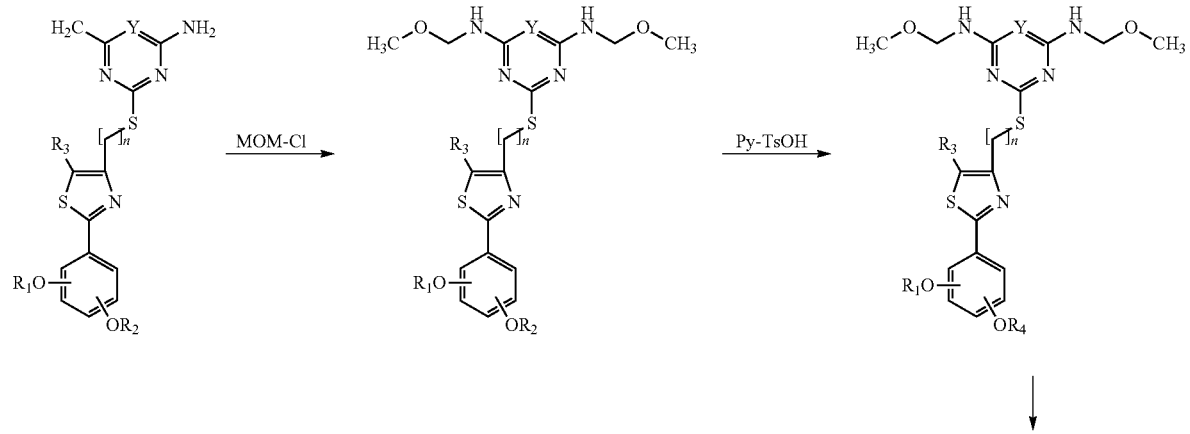

-continued

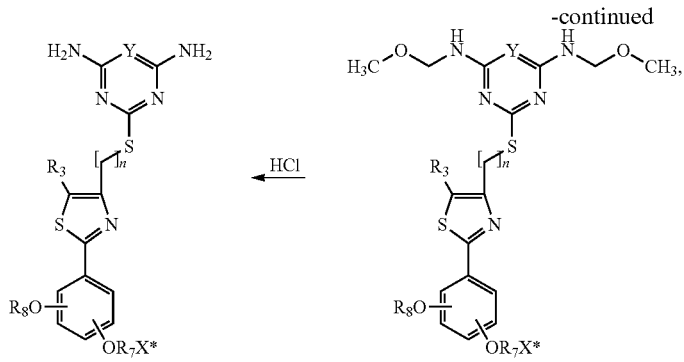
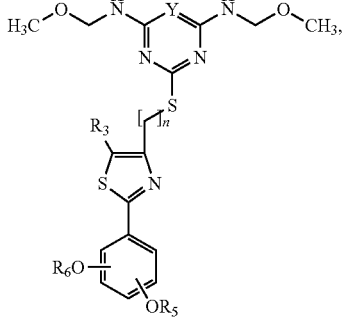

wherein the $OR_1$ and $OR_2$ groups may be attached to the 2,3-, 2,4-, 2,5-, 2,6-, 3,4- or 3,5-positions of the phenyl ring; X* may be $^{18}F$, $^{75}Br$, $^{76}Br$ or $^{124}I$; $R_{1-8}$ may be independently alkyl, fluoro-alkyl, tetrahydro-2H-pyran-protected alkyl, alkoxy or tosyl-protected alkyl groups; n=1-6; and Y is N or CH.

Additional Embodiments

Certain embodiments of the invention are further described below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

As noted above, dCK is a clinically important polypeptide target because of, for example, its role in cellular divisional (e.g. as a rate-limiting enzyme in the deoxyribonucleoside salvage metabolism), as well as its association with drug resistance and/or drug sensitivity. Studies using a dCK knock out mouse model developed by our group indicate that dCK activity is required for the formation of deoxycytidine triphosphate (dCTP), an essential nucleotide used for DNA repair in lymphocytes and in certain types of cancer. Studies also show that dCK may function as a back-up mechanism to produce deoxyribonucleotides (dNTPs) for DNA replication when the output of the main metabolic pathway used by cells to make dNTPs becomes insufficient to support the rapid growth of cancer cells. The instant disclosure illustrates the development of compounds that bind this polypeptide (including small molecule inhibitors).

The compounds that bind dCK including the small molecule inhibitors that are described herein are useful in variety of contexts, for example as probes in positron emission tomography techniques. In addition, these compounds are useful in the development of new therapeutic agents for certain pathological conditions such as cancer and cell-mediated autoimmune disorders. The small molecule inhibitors of dCK disclosed herein are also useful in processes designed to study nucleic acid metabolism in normal and malignant tissues. Such processes can be used for example to assist the development of new therapies for cancer and autoimmune disorders that work by selectively interfering with the ability of rapidly proliferating pathogenic cells to repair and replicate their DNA.

One illustrative strategy used to develop the dCK inhibitors described herein takes advantage of the Positron Emission Tomography (PET) technologies. In this context, illustrative therapeutic candidate compounds have been designed to readily incorporate a fluorine 19 atom. The fluorine 19 atom included in the scaffold of the compounds disclosed herein (see, e.g. FIG. 1) can then easily be replaced by a fluorine 18 radioisotope in order to generate a radiolabeled version of the compound, one that can be detected and quantified non-invasively throughout the body of living organisms using PET imaging techniques. By using compounds designed in this way (e.g. to take advantage of PET imaging techniques), artisans can then use of a variety of non-invasive pharmacokinetic (PK) techniques to study the therapeutic potential of these compounds (e.g. in animal models). This strategy is generally applicable in drug research and development and can accelerate this process while reducing its costs (e.g. by enabling rapid identification of therapeutic candidates with optimal PK properties).

As noted above, the small molecule dCK inhibitors disclosed herein have been designed to be readily amenable to one-step fluorine 18 radiolabeling for PET imaging studies of drug PK in animal models and in humans. This design provides these compounds with a significant advantage over chemically distinct small molecule dCK inhibitors that require multiple steps for radiolabeling. An important additional element is provided by the FAC series of PET imaging probes which are described in U.S. patent application Ser. No. 12/234,478, the contents of which are incorporated by reference. These FAC probes enable artisans to non-invasively characterize the pharmacodynamic (PD) properties of the candidate therapeutic compounds in a variety of animal species (e.g. mice and humans).

As noted above, the present invention provides small molecule inhibitors of deoxycytidine kinase (dCK), a rate-limiting enzyme in the deoxyribonucleoside salvage metabolism. We have previously developed and validated PET probes to measure dCK activity in vivo (see, e.g. Nat. Med. 2008 July; 14(7):783-8; JNM. 2010 July; 51(7):1092-8). Consequently, these validated PET probes can be used as pharmacodynamic biomarkers to validate the efficacy of the new dCK binding compounds disclosed herein.

Specific illustrative compounds and their properties are discussed below and in Appendices A and B as filed with U.S. Provisional Patent Application No. 61/450,319 filed Mar. 8, 2011, incorporated herein by reference in their entireties.

Embodiments of the present invention provide compositions of matter that include a compound having the formula:

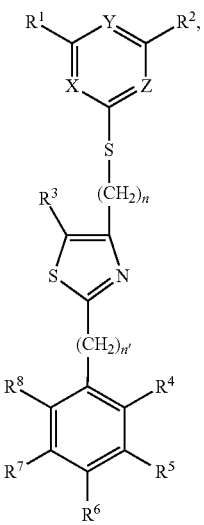

(n = 1-6)
(n' = 0-6)

wherein,

X, Y, and Z are independently selected from: CH or N;

n is a number selected from: 1, 2, 3, 4, 5 or 6;

n' is a number selected from: 0, 1, 2, 3, 4, 5 or 6;

$R_1$ and $R_2$ are independently selected from: $NH_2$, $NH_3W$, $NH_3Me$, $NH_3Et$, OH, $OCH_3$ or $OC_2H_5$, and wherein W is selected from: F, Cl, Br, I, $NO_3$, $SO_4$, $HSO_4$, $H_2PO_4$, $HPO_4$ or $PO_4$;

$R_3$ is independently selected from: H, $CH_3$, $C_2H_5$, $C_3H_7$ or $OCH_3$; and $R_4$, $R_5$, $R_6$, $R_7$, and $R_8$ are independently selected from: H, F, Cl, Br, I, $OR_9$, $OR_{10}$, $OR_{11}$, $OR_{12}$, or $OR_{13}$;

wherein, $R_9$ is selected from: $CH_3$, $C_2H_5$, $C_3H_7$, $C_4H_9$, $C_5H_{11}$, $C_6H_{13}$, $CH_2F$, $C_2H_4F$, $C_3H_6F$, $C_4H_8F$, $C_5H_{10}F$, $C_6H_{12}F$, $C_2H_4Br$, $C_2H_4I$, $CF_3$, $C_2F_5$, $C_3F_7$, $C_4F_9$, $C_5F_{11}$ or $C_6F_{13}$;

$R_{10}$ is selected from: $CH_2OTs$, $C_2H_4OTs$, $C_3H_6OTs$, $C_4H_8OTs$, $C_5H_{10}OTs$, or $C_6H_{12}OTs$, and wherein Ts is tosyl;

$R_{11}$ is selected from: $CH_2OH$, $C_2H_4OH$, $C_3H_6OH$, $C_4H_8OH$, $C_5H_{10}OH$ or $C_6H_{12}OH$;

$R_{12}$ is selected from: $CH_2OTHP$, $C_2H_4OTHP$, $C_3H_6OTHP$, $C_4H_8OTHP$, $C_5H_{10}OTHP$ or $C_6H_{12}OTHP$, and wherein THP is 2-tetrahydropyranyl group; and $R_{13}$ is selected from: $CH_2X^*$, $C_2H_4X^*$, $C_3H_6X^*$, $C_4H_8X^*$, $C_5H_{10}X^*$, $C_6H_{12}X^*$, and wherein $X^*$ is selected from: F-18, Br-75, Br-76 or I-124.

In one embodiment, the compositions of matter comprises a compound (termed herein "DI-F2.2.1") having the formula:

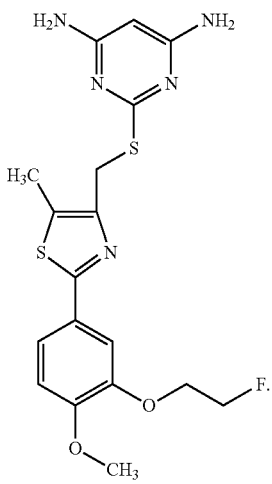 [SMILES: COc1ccc(-c2nc(CSc3nc(N)cc(N)n3)c(C)s2)cc1OCCF]

In another closely related embodiment, the invention provides a composition of matter selected for its ability to bind to and inhibit deoxycytidine kinase activity, the composition of matter comprising a compound having the formula:

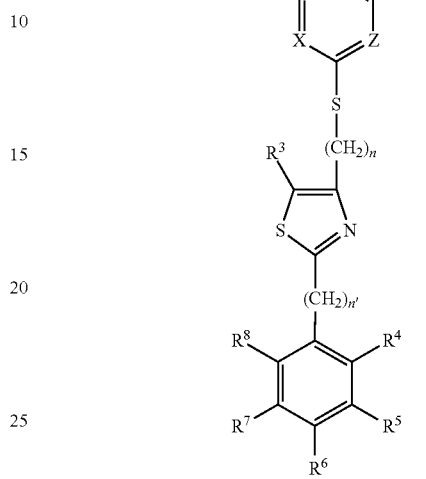

(n = 1-6)
(n' = 0-6)

wherein,

X, Y, and Z are independently selected from: CH or N;

n is a number selected from: 1, 2, 3, 4, 5 or 6;

n' is a number selected from: 0, 1, 2, 3, 4, 5 or 6;

$R_1$ and $R_2$ are independently selected from: $NH_2$, $NH_3W$, $NH_3Me$, $NH_3Et$, OH, $OCH_3$ or $OC_2H_5$, and wherein W is selected from: F, Cl, Br, I, $NO_3$, $SO_4$, $HSO_4$, $H_2PO_4$, $HPO_4$ or $PO_4$;

$R_3$ is independently selected from: H, $CH_3$, $C_2H_5$, $C_3H_7$ or $OCH_3$; and $R_4$, $R_5$, $R_6$, $R_7$, and $R_8$ are independently selected from: H, F, Cl, Br, I, $OR_9$, $OR_{10}$, $OR_{11}$, $OR_{12}$, or $OR_{13}$;

wherein, $R_9$ is selected from: $CH_3$, $C_2H_5$, $C_3H_7$, $C_4H_9$, $C_5H_{11}$, $C_6H_{13}$, $CH_2F$, $C_2H_4F$, $C_3H_6F$, $C_4H_8F$, $C_5H_{10}F$, $C_6H_{12}F$, $C_2H_4Br$, $C_2H_4I$, $CF_3$, $C_2F_5$, $C_3F_7$, $C_4F_9$, $C_5F_{11}$ or $C_6F_{13}$;

$R_{10}$ is selected from: $CH_2OTs$, $C_2H_4OTs$, $C_3H_6OTs$, $C_4H_8OTs$, $C_5H_{10}OTs$, or $C_6H_{12}OTs$, and wherein Ts is tosyl;

$R_{11}$ is selected from: $CH_2OH$, $C_2H_4OH$, $C_3H_6OH$, $C_4H_8OH$, $C_5H_{10}OH$ or $C_6H_{12}OH$;

$R_{12}$ is selected from: $CH_2OTHP$, $C_2H_4OTHP$, $C_3H_6OTHP$, $C_4H_8OTHP$, $C_5H_{10}OTHP$ or $C_6H_{12}OTHP$, and wherein THP is 2-tetrahydropyranyl group; and $R_{13}$ is selected from: $CH_2X^*$, $C_2H_4X^*$, $C_3H_6X^*$, $C_4H_8X^*$, $C_5H_{10}X^*$, $C_6H_{12}X^*$, and wherein $X^*$ is selected from: F-18, Br-75, Br-76 or I-124.

In one illustrative embodiment of a composition of matter for inhibiting dCK activity, the composition comprises a compound having the formula:

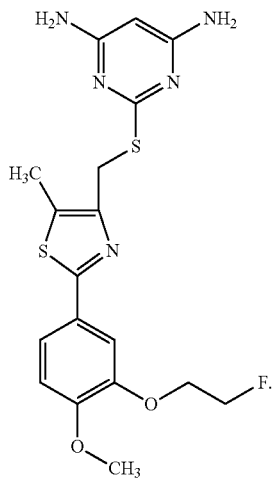

As noted above, in certain embodiments of the invention are used as probes in imaging techniques designed to monitor one or more aspects cellular physiology. In this context, embodiments of the invention can be used, for example, to monitor immune function throughout the body, a monitoring technique that may significantly impact the diagnosis and treatment evaluation of immunological disorders. In certain embodiments of the invention, a compound disclosed herein is used as a PET probe in a process for imaging one or more features of a biological material as part of a diagnostic or therapeutic technique. For example, the PET probe can be used in the diagnosis and treatment of a condition selected from the group consisting of rheumatoid arthritis, inflammatory bowel disease, type 1 diabetes, EAE (Experimental Autoimmune Encephalomyelitis), multiple sclerosis, atherosclerosis, an autoimmune disorder, and cancer. In addition, the PET probe can be used to evaluate the efficacy in the treatment of cancer of anticancer agents that are taken up into cells via nucleoside transporters and deoxycytidine kinase (dCK)-mediated phosphorylation. As evident to one of ordinary skill in the art, in addition to the compound, the compositions of the invention can include one or more pharmaceutically acceptable carriers and/or excipients. One of ordinary skill in the art will be able to selection appropriate pharmaceutically acceptable carriers and/or excipients based on the envisioned application.

Illustrative methods of imaging according to the invention typically include one or more of the following steps. A PET probe can be contacted with biological material. PET imaging can then be used to determine a local concentration of the PET probe in the biological material. And the local concentration of the PET probe can then be correlated with localized nucleotide metabolism, for example, the accumulation of activated T lymphocytes (e.g. as activated T lymphocytes take up more PET probe per cell than non-activated T lymphocytes). In this manner, PET imaging can be used to determine a local concentration of the PET probe administered to an animal or a human, and the local concentration of the PET probe can then be correlated with aspects of nucleotide metabolism, for example, with a local immune response or abnormal cell growth. For example, the local concentration of the PET probe can be correlated with abnormal cellular activity in an organ or portion of the lymphatic system, for example, in a lymph node or in the spleen. Similarly, the local concentration of the PET probe can be correlated with a lymphoma lesion or with a malignant lymphoid disease.

The animal or human in which a compound disclosed herein is used can, for example, have a condition such as cancer, lymphadenopathy, melanoma, leukemia, glioma, an autoimmune disorder, a development disorder, viral infection, bacterial infection, parasitical infection, infection, a metabolic disease, inflammation, rheumatoid arthritis, inflammatory bowel disease, type 1 diabetes, Experimental Autoimmune Encephalomyelitis (EAE), multiple sclerosis, and/or atherosclerosis. In such contexts, the PET probe can be used in procedure for the diagnosis and/or treatment of such a condition. For example, the animal or human can be undergoing a therapy such as cancer immunotherapy, immunotherapy, interferon therapy, vaccination, radiation therapy, chemotherapy, and/or antibiotic therapy. In an illustrative embodiment, the local concentration of the PET probe can be used to diagnose cancer and/or monitor cancer treatment.

In a specific illustrative embodiment of the invention, lymphocyte activation can be non-invasively monitored by injecting a subject animal or human with a trace amount of an PET probe disclosed herein, allowing the probe to accumulate at sites of local immune activation and then monitoring the subject at a whole body level using a PET scanner. Such a PET probe can be administered to an animal or a human for diagnostic purposes such as to determine the presence or extent of a disease or disorder (e.g., cancer, autoimmune disease, developmental disorder, viral infection, bacterial infection, parasitical infection, other infections, metabolic disease, or inflammation). In embodiments of the invention, the PET probe can be administered to monitor the progress of cancer or other disease-based types of immunotherapy, interferon therapy, vaccination, radiation therapy, and antibiotic therapy.

Embodiments of the invention further provide methods of evaluating the usage efficacy of particular classes of anti-cancer agents in the treatment of cancer such as those that are taken up into cells via nucleoside transporters and deoxycytidine kinase (dCK)-mediated phosphorylation. For example, the PET probe can be used to evaluate the efficacy in the treatment of cancer of an anticancer agent, e.g., cytarabine or 2'-difluorodeoxycytidine, that is taken up into cells via nucleoside transporters and deoxycytidine kinase (dCK)-mediated phosphorylation. In an additional aspect, the present invention relates to methods of diagnosis and treatment of conditions that implicate cells with high deoxyribonucleoside salvage pathway activity, e.g., lymphocytes, bone marrow cells, and intestinal enterocytes. In another aspect, the present invention relates to compositions incorporating the compounds disclosed herein. In still another aspect, the present invention relates to kits comprising any embodiment of the present invention.

Other embodiments of the invention include articles of manufacture and/or kits, for example those containing materials useful in diagnostic imaging techniques. Alternatively, the articles of manufacture and/or kits can contain materials useful in treating a pathological condition such as an immune disorder or a cancer. In typical embodiments of the invention, the kit comprises at least one container, typically with a label. Suitable containers include, for example, blister packs, bottles, vials, and test tubes. The containers may be formed from a variety of materials such as metal (e.g., a metal foil), glass or plastic. In some embodiments of the invention, the one or more containers holds one or more compositions having an active agent which is effective in diagnostic imaging techniques. In other embodiments of the invention, the one or more containers holds one or more compositions having an active agent which is effective in treating a pathological condition such as an immune disorder or a cancer. In certain embodiments of the invention, an active agent in the composition is a dCK binding compound as disclosed herein (see, e.g. FIG. 1). In some embodiments of the invention, the kit comprises a composition including a dCK binding compound as disclosed herein and thymidine (e.g. in a combined formulation or "cocktail"). In some embodiments the kit comprises a first composition including a dCK binding compound in a first container, and a second composition including thymidine in a second container. Typically, the label on the one or more containers indicates that the one or more compositions is used for diagnostic imaging techniques or in treating a pathological condition such as an immune disorder and/or a cancer. Such labels may also indicate directions for either in vivo or in vitro use, such as those described herein. The kits of the invention can also comprise the one or more containers described above and a further container comprising a buffer. Kits may further include other materials desirable from a commercial and user standpoint, including other buffers, diluents, filters, needles, syringes, and package inserts with instructions for use.

The present invention also provides a research tool comprising a compound of the invention for studying nucleic acid metabolism in normal and malignant tissues. In certain embodiments, a FAC series of PET imaging probes, as described in U.S. patent application Ser. No. 12/234,478, which is incorporated herein by reference, are used to non-invasively determine the pharmacodynamic (PD) properties of the therapeutic candidates in mice, other animal species and in humans.

In certain embodiments of the invention, a composition of matter comprising a compound disclosed herein may be used as a therapeutic agent for cancer. In other embodiments, the composition of matter is used as a therapeutic agent for autoimmune disorders. In some instances, the composition of matter may be used as a therapeutic agent for cancer and/or autoimmune disorders by binding dCK in a manner that selectively interferes with the ability of rapidly proliferating pathogenic cells to repair and replicate their DNA. Typically the therapeutic agents used in the methods of the invention combined with at pharmaceutically acceptable carrier. The term "pharmaceutically acceptable carrier" is used according to its art accepted meaning and is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration.

The invention can be further understood by reference to the following examples, which are provided by way of illustration and are not meant to be limiting.

EXAMPLES

Example 1

Synthesis of Compound DI-F2.2.1

Compound DI-F2.2.1 was synthesized according to the following scheme:

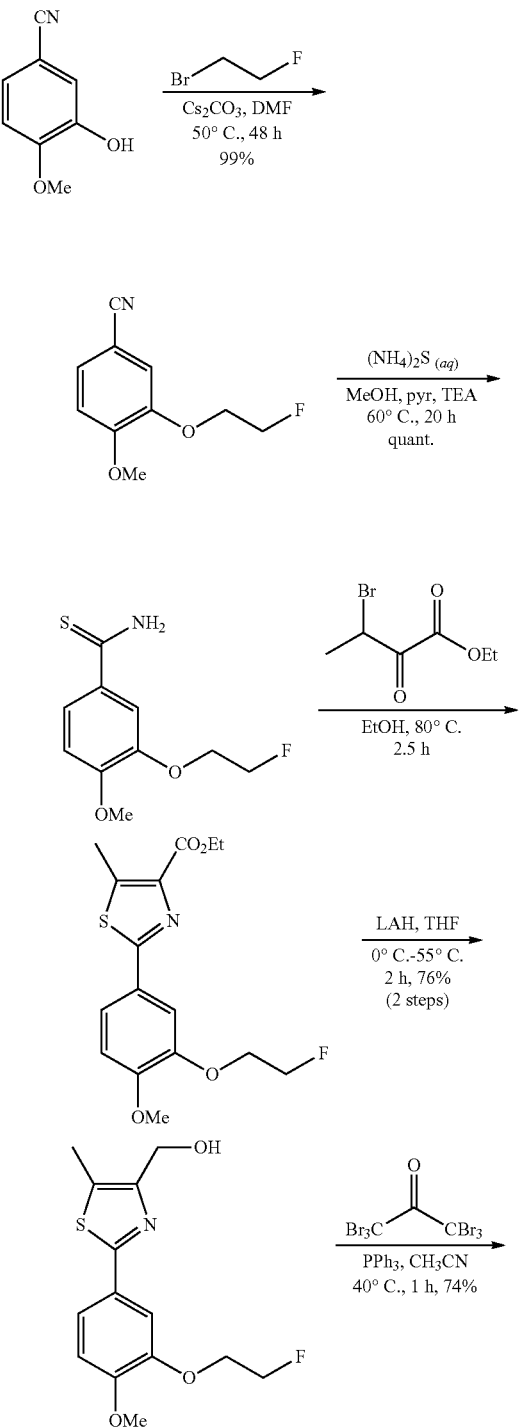

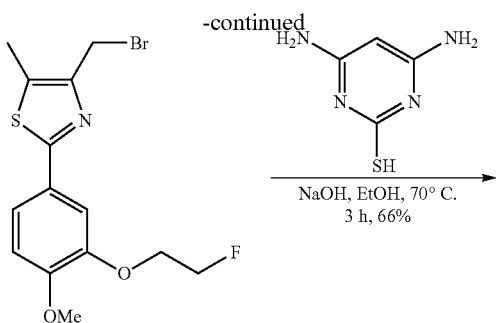

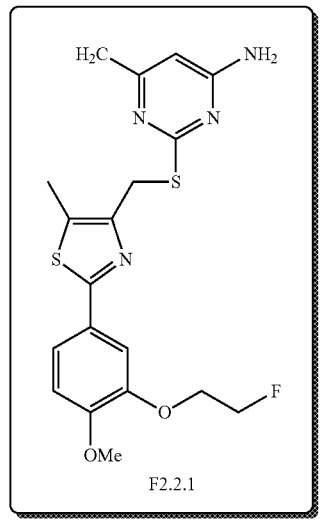

F2.2.1

To a solution of functionalized benzonitrile substrate (2.0 g, 13.4 mmol) in anhydrous DMF (30 mL) at room temperature under N₂, Cs₂CO₃ (8.74 g, 26.8 mol) and 1-bromo-2-fluoroethane (5.07 g, 40.2 mmol) were added once. The mixture was stirred at 50° C. for 2 days. The solvent was removed in vacuo and the crude material was taken on to the next step without further purification (2.14 g, 82%). Exemplary NMR data given for the synthetic intermediate towards F2.2.1: $^1$H NMR (CDCl₃) δ: 7.31-7.34 (dd, J=1.9, 8.4 Hz, 1H), 7.13-7.13 (d, J=1.9 Hz, 1H), 6.91-6.93 (d, J=8.4 Hz, 1H), 4.85-4.87 (m, 1H), 4.73-4.75 (m, 1H), 4.30-4.32 (m, 1H), 4.23-4.25 (m, 1H), 3.93 (s, 1H).

The crude fluoroethoxy substrate (1.00 g, 5.1 mmol) was dissolved in pyridine (3.5 mL), then triethylamine (0.8 mL), and ammonium sulfide 20% wt solution in water (2.0 mL) were added into the mixture at 60° C. for 20 h. The solution turned from yellow to green upon the addition of ammonium sulfide. The pyridine was removed in vacuo. The reaction mixture was extracted with ethyl acetate and washed with saturated aqueous ammonium chloride solution. The organic layer was dried over MgSO₄ and concentrated in vacuo to a yellow solid (0.99 g, 84%). The solid was used without further purification. Exemplary NMR data given for the synthetic intermediate towards F2.2.1: $^1$H NMR (acetone-d₆) δ: 8.75 (s, 2H) 7.71-7.73 (m, 2H), 7.00-7.02 (d, J=8.4 Hz, 1H), 4.84-4.86 (m, 1H), 4.72-4.74 (m, 1H), 4.35-4.37 (m, 1H), 4.27-4.29 (m, 1H), 3.89 (s, 3H); $^{13}$C NMR (CDCl₃) δ: 201.2, 153.3, 147.4, 131.5, 119.8, 114.5, 110.6, 82.4, 81.1, 68.6, 68.4, 56.2.

To a stirred solution of the thio amide substrate (3.80 g, 11.1 mmol) in absolute ethanol (56 ml), ethyl 3-bromo-2-oxobutanoate (3.49 g, 16.7 mmol) was added. The reaction mixture was refluxed for 2.5 h under nitrogen. After the completion of reaction by TLC examination, the mixture was cooled to −10° C. in freezer and the product precipitated out was filtered and washed with EtOH. The brown product (3.19 g, 85%) was used without further purification.

To a stirred solution of the thiazole cyclization product (2.0 g, 3.5 mmol) in anhydrous THF (38 ml) at 0° C. under nitrogen, lithium aluminum hydride (0.18 g, 4.8 mmol) was added in portion. The solution was allowed to warm to ambient temperature and then heated to 55° C. and stirred for 2 h. The reaction mixture was cooled to 0° C. and quenched slowly by the addition of saturated aqueous Na₂SO₄ then 15% aqueous NaOH solution. Solid Na₂SO₄ and celite was added and the reaction stirred for approximately 10 mins. Filtered over a short pad of celite and concentrated in vacuo to a crude oil. The oil was purified by flash column chromatography to yield the product as white solid (1.62 g, 87%).

To a stirred solution of the free alcohol (0.75 g, 2.9 mmol) in dry acetonitrile (9.6 mL) at 0° C. under N₂, hexabromoacetone (0.51 g, 1.0 mmol) and PPh₃ were added. The solution was warmed to 40° C. and stirred for 1 h. After the completion, the reaction mixture was extracted with CH₂Cl₂. The organic layer was washed with brine then dried over MgSO₄. The organic layers were combined, concentrated and purified by column chromatography to yield pale yellow solid (0.98 g, 86%).

To a suspension of 4,6-diaminopyrimidine-2(1H)-thione (0.39 g, 2.8 mmol) in EtOH (37 mL) was added NaOH (0.11 g, 2.8 mmol) and the mixture was stirred at room temp for 10 minutes. The alkyl bromide substrate (1.37 g, 2.3 mmol) was added as a solution in ethanol and the reaction mixture was heated to 70° C. for 3 h. The reaction mixture was cooled, concentrated in vacuo and purified by flash column chromatography to yield a pale yellow solid (1.19 g, 79%). $^1$H NMR (DMSO-d₆) δ: 7.36 (1H, s), 7.34 (1H, d, J=8.0 Hz), 7.02 (1H, d, J=8.5 Hz), 6.09 (4H, bs), 5.12 (1H, s), 4.76 (1H, m), 4.66 (1H, m), 4.32 (2H, s), 4.27 (1H, m), 4.21 (1H, m), 3.78 (3H, s), 2.43 (3H, s).

Example 2

Synthesis of Compound DI-26

Figure 3:
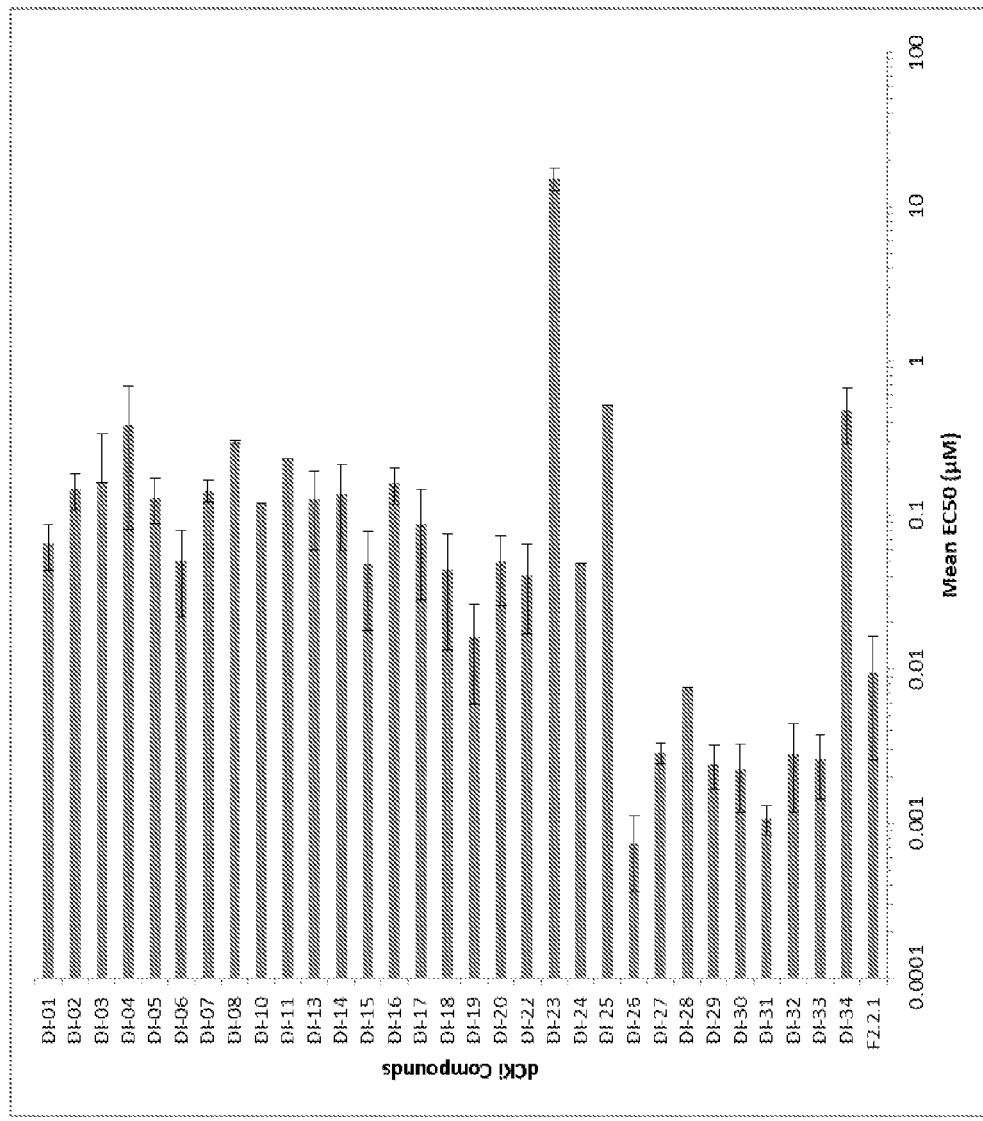
FIG. 3 illustrates the activity of dCK inhibitors ($EC_{50}$) in an assay for inhibition of [$^3$H]-deoxycytidine (dCyd) uptake by CEM cells.

Compound DI-26 was synthesized according to the following scheme. A $^1$H NMR spectrum of Compound DI-16 in DMSO-d₆ is shown in FIG. 3.

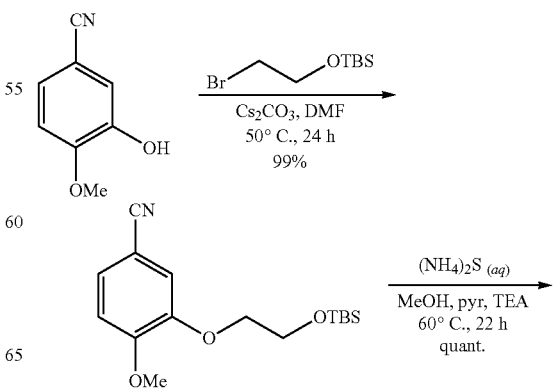

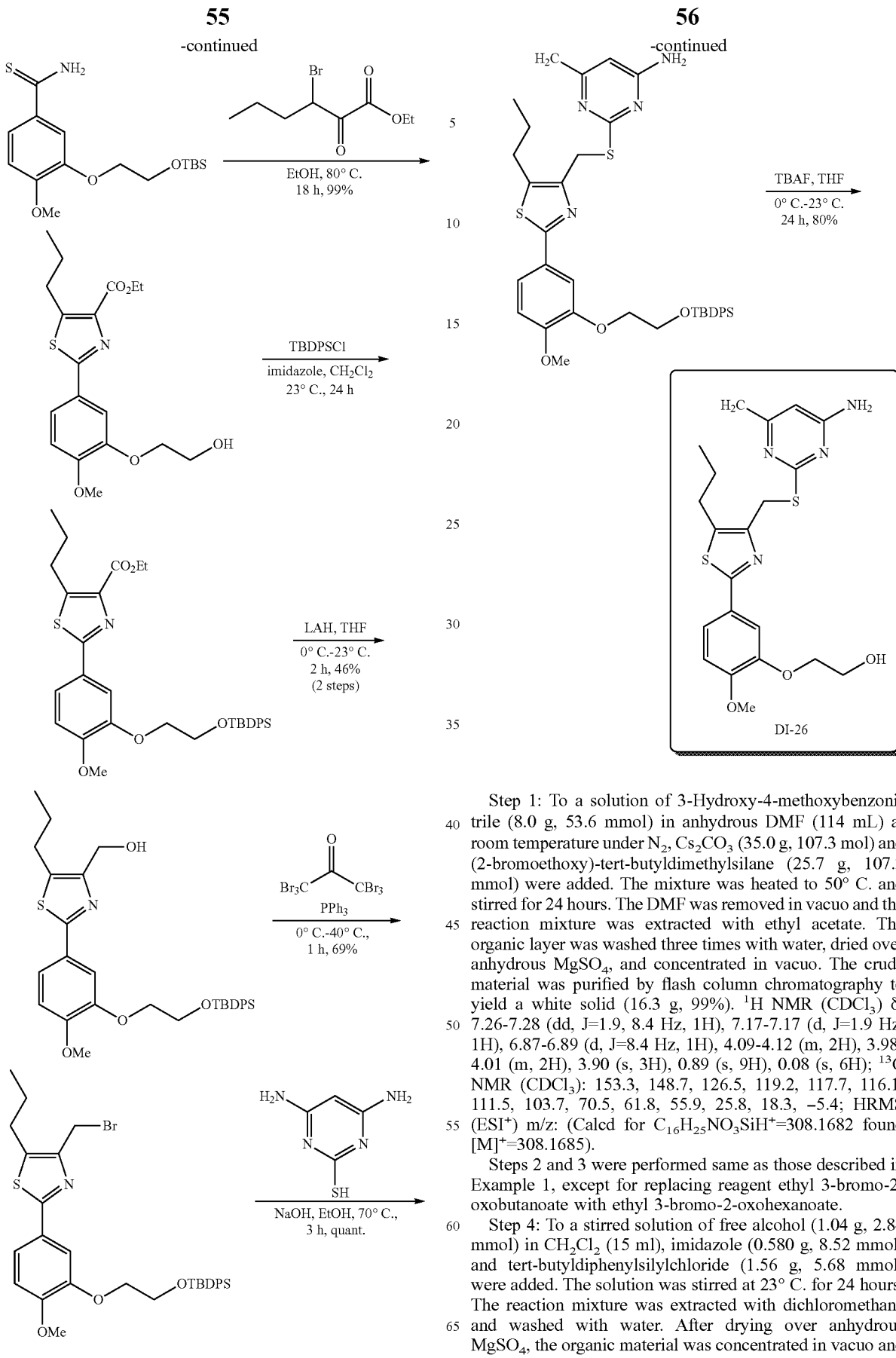

Step 1: To a solution of 3-Hydroxy-4-methoxybenzonitrile (8.0 g, 53.6 mmol) in anhydrous DMF (114 mL) at room temperature under $N_2$, $Cs_2CO_3$ (35.0 g, 107.3 mol) and (2-bromoethoxy)-tert-butyldimethylsilane (25.7 g, 107.3 mmol) were added. The mixture was heated to 50° C. and stirred for 24 hours. The DMF was removed in vacuo and the reaction mixture was extracted with ethyl acetate. The organic layer was washed three times with water, dried over anhydrous $MgSO_4$, and concentrated in vacuo. The crude material was purified by flash column chromatography to yield a white solid (16.3 g, 99%). $^1$H NMR (CDCl$_3$) δ: 7.26-7.28 (dd, J=1.9, 8.4 Hz, 1H), 7.17-7.17 (d, J=1.9 Hz, 1H), 6.87-6.89 (d, J=8.4 Hz, 1H), 4.09-4.12 (m, 2H), 3.98-4.01 (m, 2H), 3.90 (s, 3H), 0.89 (s, 9H), 0.08 (s, 6H); $^{13}$C NMR (CDCl$_3$): 153.3, 148.7, 126.5, 119.2, 117.7, 116.1, 111.5, 103.7, 70.5, 61.8, 55.9, 25.8, 18.3, −5.4; HRMS (ESI$^+$) m/z: (Calcd for $C_{16}H_{25}NO_3SiH^+$=308.1682 found [M]$^+$=308.1685).

Steps 2 and 3 were performed same as those described in Example 1, except for replacing reagent ethyl 3-bromo-2-oxobutanoate with ethyl 3-bromo-2-oxohexanoate.

Step 4: To a stirred solution of free alcohol (1.04 g, 2.84 mmol) in $CH_2Cl_2$ (15 ml), imidazole (0.580 g, 8.52 mmol) and tert-butyldiphenylsilylchloride (1.56 g, 5.68 mmol) were added. The solution was stirred at 23° C. for 24 hours. The reaction mixture was extracted with dichloromethane and washed with water. After drying over anhydrous $MgSO_4$, the organic material was concentrated in vacuo and used without further purification.

Steps 5, 6 and 7 were performed same as those described in Example 1.

Step 8: To a stirred solution of the pyrimidine moiety (0.310 g, 0.45 mmol) in THF (5 ml) at 0° C. under $N_2$, t-butylammonium fluoride (0.90 ml, 1.0 M solution in THF, 0.90 mmol) solution was added dropwise. The solution was warmed to ambient temperature and stirred for 24 hours. After completion, the reaction solution was concentrated and purified by flash column chromatography to yield the final compound, DI-26, a white solid (0.160 g, 0.36 mmol, 80%). $^1$H NMR (DMSO-$d_6$) δ: 7.35 (1H, s), 7.34 (1H, d, J=9.5 Hz), 7.00 (1H, d, J=9.0 Hz), 6.11 (4H, bs), 5.12 (1H, s), 4.84 (1H, dd, J=5.5, 5.5 Hz), 4.35 (2H, s), 3.99 (2H, m), 3.77 (3H, s), 3.69 (2H, m), 2.80 (2H, dd, J=7.5, 7.5 Hz), 1.54 (2H, m), 0.88 (3H, dd, J=7.5, 7.5 Hz). ESI TOF MS m/z 448.1471, calculated for $C_{20}H_{26}N_5O_3S_2$ ([M+H]$^+$) 448.1477.

Example 3

Synthesis of Compound DI-30

Figure 24:
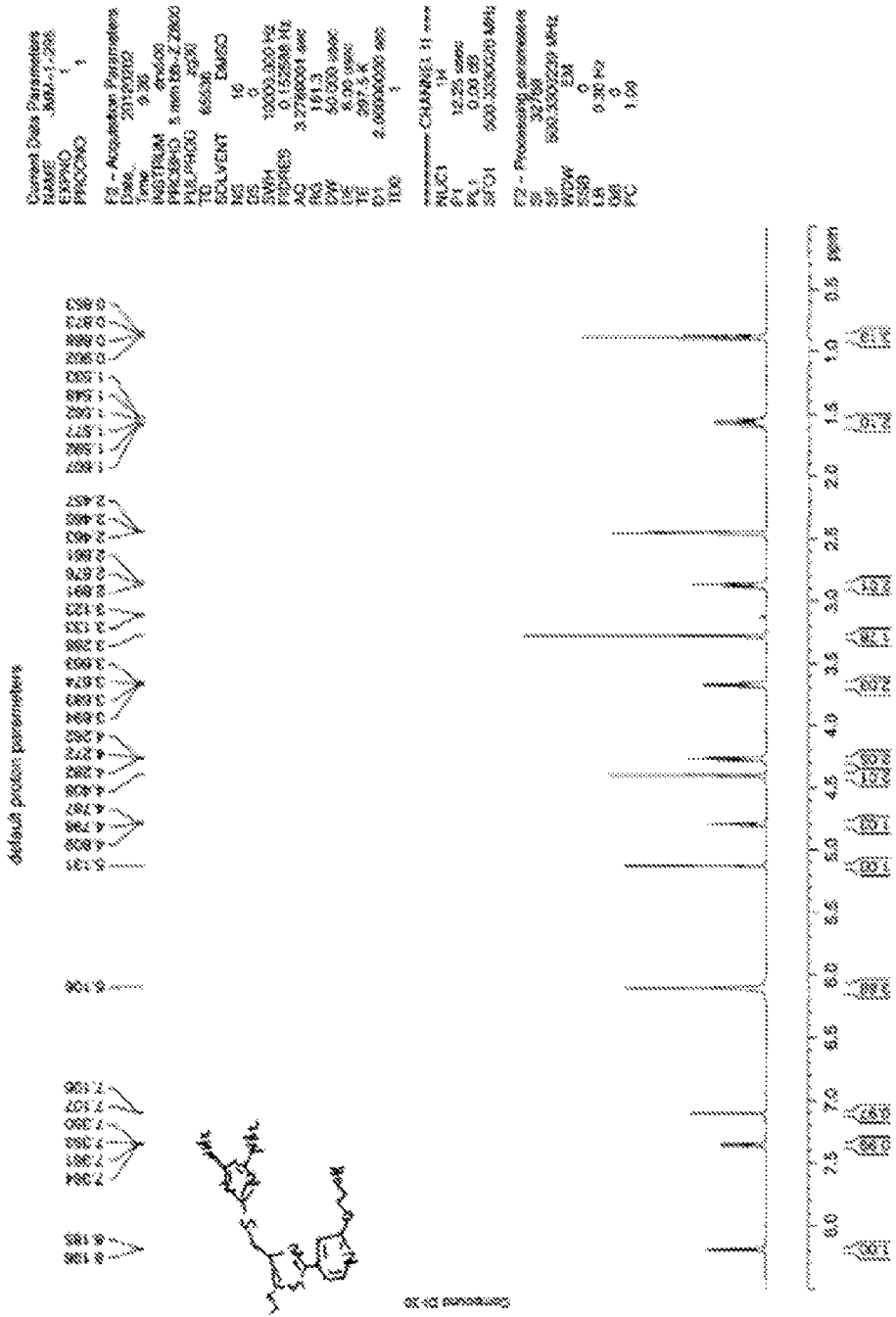
FIG. 24 shows a $^1$H NMR spectrum of Compound DI-30 in DMSO-$d_6$.

Compound DI-30 was synthesized according to the following scheme, following the procedures similar to those described in Example 2. $^1$H NMR spectrum of Compound DI-30 in DMSO-$d_6$ is shown in FIG. 24. ESI TOF MS m/z 419.1325, calculated for $C_{18}H_{23}N_6O_2S_2$ ([M+H]$^+$) 419.1324.

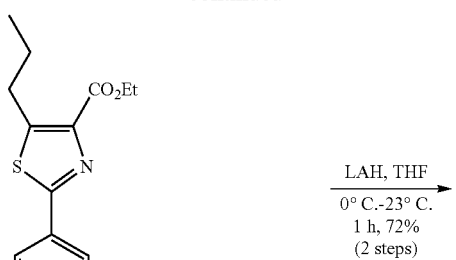
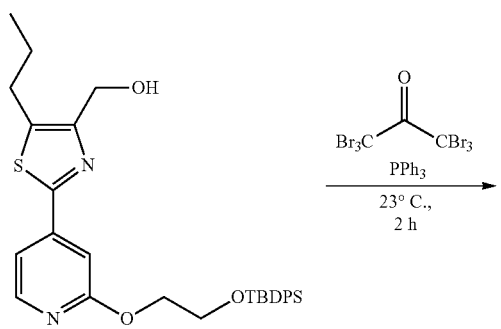
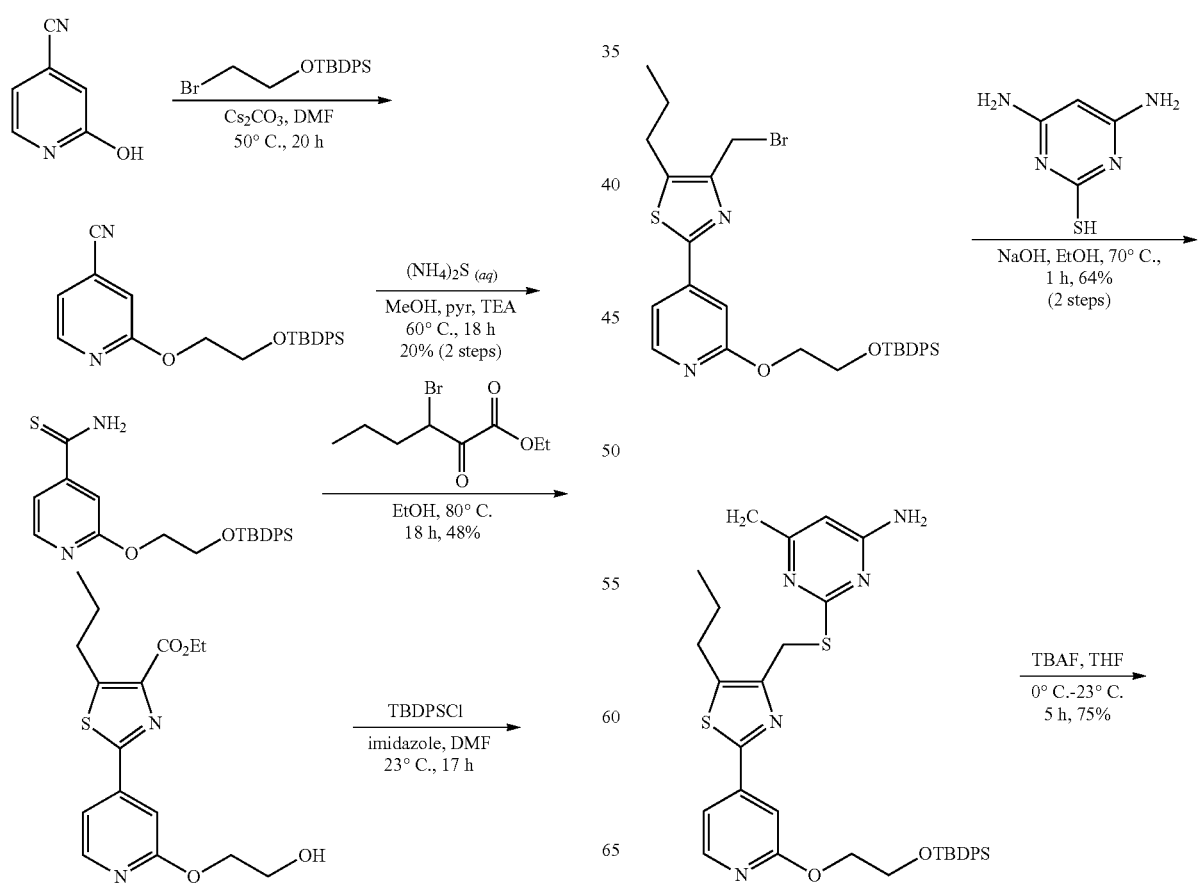

-continued

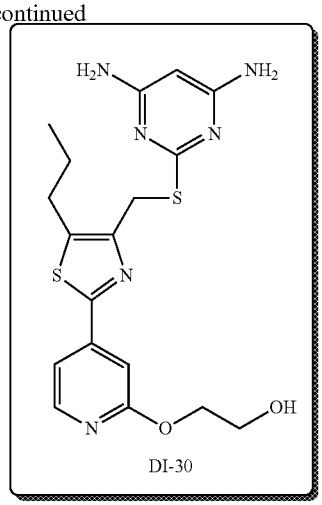

DI-30

Example 4

Determination of Activity of dCK Inhibitors in Inhibition of [$^3$H]-dCyd Uptake by CEM Cells Materials and Methods:

50,000 CEM cells/well were added to Millipore Multi-Screen GV 96 well plates. Cells were resuspended at 1×10^6 cells/mL and incubated for 30 minutes at 37° C. The drug dilution plate was prepared by starting with an initial drug concentration of 10 mM in DMSO, and proceeding to make 1:5 dilutions for drug. 10 mL of drug was added to 40 mL DMSO and mixed by pipetting 10 times before removing 10 uL for next well (1:5 serial dilutions). The media and tritiated deoxycytidine was mixed together. 245 mL of media/probe mixture was added to each well of an Optiplate. 5 mL from drug plate was added to each well in the Optiplate to obtain drug/media/probe mixture and mixed. 50 mL of drug/media/probe mixture from Optiplate was added to the cell plate and incubate at 37° C. for 1 hour. The cell plate was placed on vacuum to aspirate, and then washed with ice cold PBS: 200 mL 1×PBS 4 times. The backing of the plate was peeled off, and the plate was placed in dryer for at least 30 minutes or until dry at 37° C. 100 mL Scintillation fluid per well was added, and the plate was sealed with clear plate seal. The plate was read on the Microbeta instrument.

Figure 4:
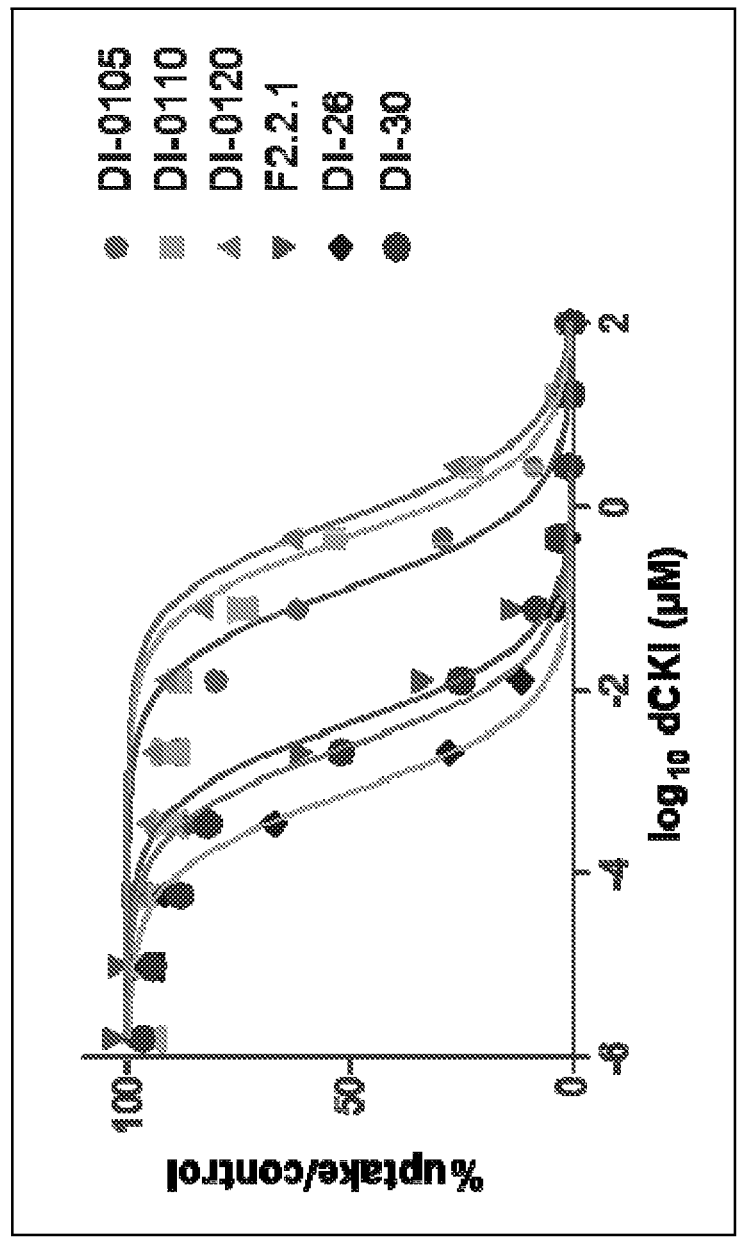
FIG. 4 shows data for inhibition of dCyd uptake by compounds DI-26, DI-30, F.2.2.1 in comparison with that by compounds DI-0105, DI-0110 and DI-0120.

Inhibition of [$^3$H]-deoxycytidine (dCyd) uptake by CEM cells was measured for Compounds DI-01, DI-02, DI-03, DI-04, DI-05, DI-06, DI-07, DI-08, DI-10, DI-11, DI-13, DI-14, DI-15, DI-16, DI-17, DI-18, DI-19, DI-20, DI-22, DI-23, DI-24, DI-25, DI-26, DI-27, DI-28, DI-29, DI-30, DI-31, DI-32, DI-33, DI-34 and F2.2.1. The $EC_{50}$ values obtained are shown in FIG. 3. Compounds DI-26, DI-27, DI-29 and DI-30 are among the most potent compounds in this panel. Compounds DI-26, DI-30, F.2.2.1 also showed superior activities compared with that of compounds DI-0105, DI-0110 and DI-0120 (see FIG. 4 and Table 1).

TABLE 1

| Compound | DI-0105 | DI-0110 | DI-0120 | F2.2.1 | DI-26 | DI-30 |
|---|---|---|---|---|---|---|
| dCKi-$EC_{50}$ (μM) | 0.1331 | 0.4775 | 0.7791 | 0.0044 | 0.0008 | 0.0025 |

Figure 5:
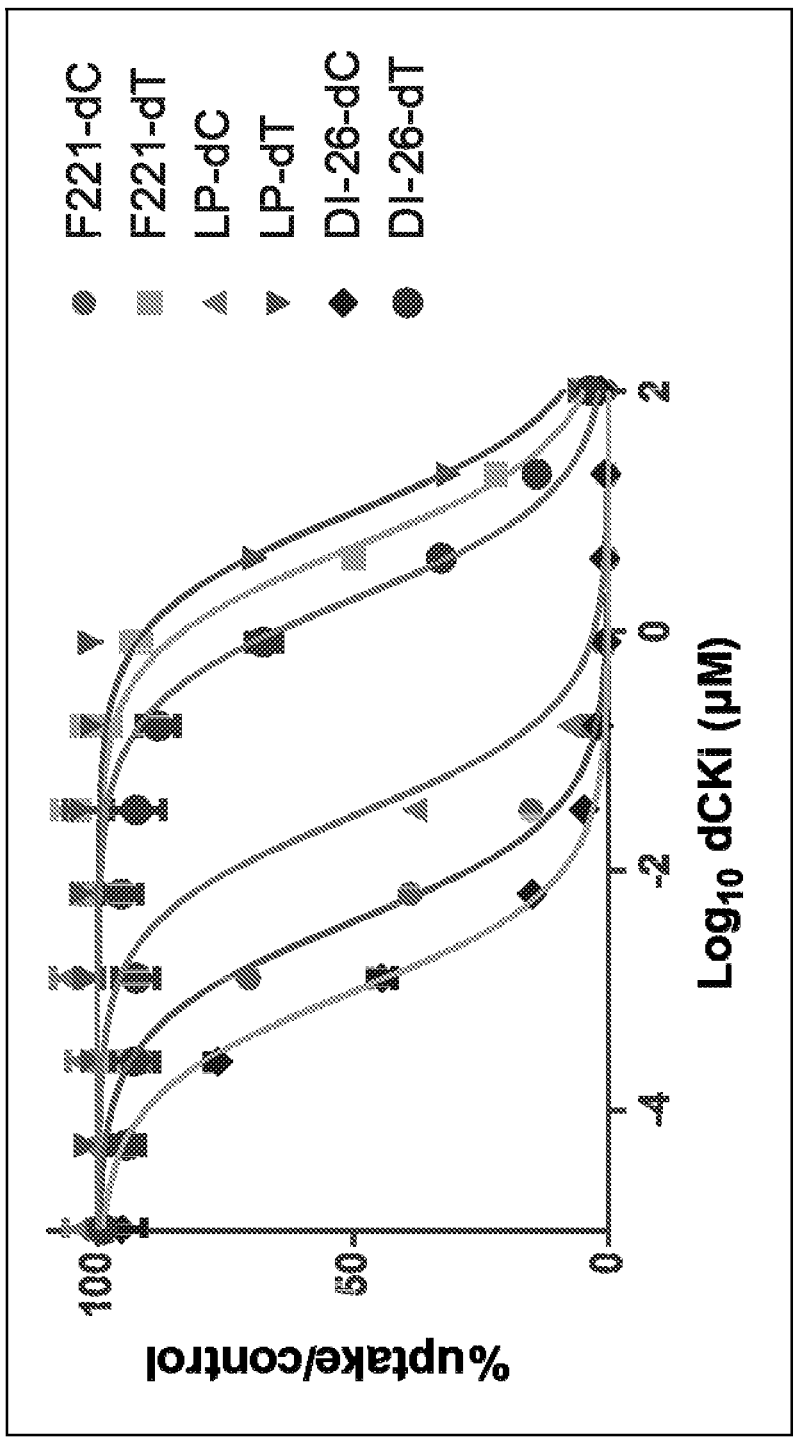
FIG. 5 shows data for inhibition of deoxycytidine (dC) vs. thymidine (dT) uptake by Compounds DI-26, F2.2.1 and LP (LP-661438, a known dCK inhibitor).

Data for compounds DI-26 and F2.2.1 in inhibiting deoxycytidine (dC) vs. thymidine (dT) uptake, in comparison with LP-661438 (a known dCK inhibitor by Lexicon Pharmaceuticals Inc.) are presented in FIG. 5 and Table 2. Compounds DI-26 and F2.2.1 are more selective than that of LP-661438.

TABLE 2

| Compounds | dCKi $IC_{50}$ (μM) dC | dCKi $IC_{50}$ (μM) dT | Selectivity (dT/dC) |
|---|---|---|---|
| F2.2.1 | 0.0038 | 4.931 | 1298 |
| DI-26 | 0.0009 | 1.824 | 2027 |
| LP-661438 | 0.0285 | 9.571 | 336 |

Example 5

Test for Inhibition of dCK Activity In Vivo Using PET Imaging

Figure 6:
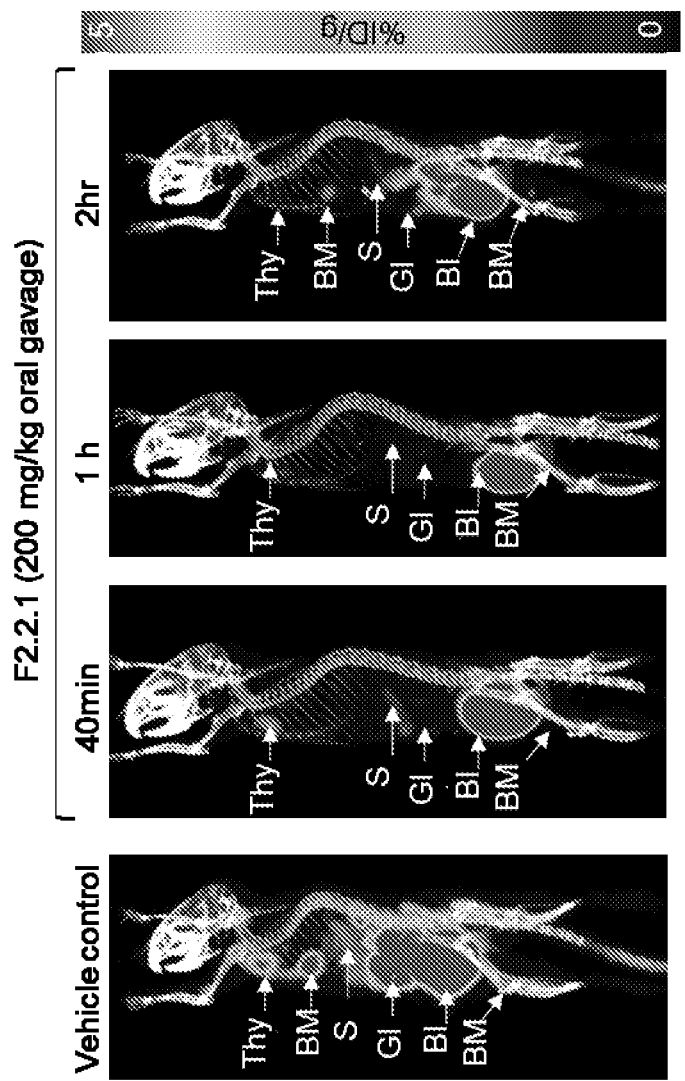
FIG. 6 shows effects of Compound F2.2.1 in inhibiting dCK activity in mice as demonstrated by PET imaging using the $^{18}$F-FAC probe.

Mice were treated with the dCK inhibitor and scanned at indicated time points by $^{18}$F-FAC PET/CT to non-invasively determine dCK activity in vivo, throughout the body. $^{18}$F-FAC PET/CT scans were performed as described in Shu, C. J. et al., "Novel PET probes specific for deoxycytidine kinase" *J. Nucl. Med.* 51(7):1092-8 (2010). Significant decrease in $^{18}$F-FAC signals was induced by F.2.2.1 in dCK expressing tissues such as Thymus (Thy), Bone marrow (BM), spleen (S) and the GI tract. $^{18}$F-FAC signals in the bladder, which is a probe clearance organ, are not affected by F.2.2.1 treatment (see FIG. 6). The data indicates that Compound F2.2.1 (200 mg/kg oral gavage) inhibits dCK activity in vivo in multiple tissues for at least 2 hours following oral administration.

Example 6

Synergistic Effect of Compound F2.2.1 in Combination with Thymidine (dT) on Cell Cycle Arrest in Human Cancer Cell Lines

Example 6.1

Cell lines (CCRF-CEM (CEM): human acute T lymphoblastic leukemia; NALM-6: human acute B lymphoblastic leukemia; IGROV1: human ovarian adenocarcinoma) were treated with thymidine (dT) (50 mM for CEM cells; 1.6 mM for NALM-6 cells and 1 mM for IGROV1 cells) for 24 hours, in the presence or absence of 1 mM deoxycytidine kinase (dCK) inhibitor F2.2.1. At the end of the incubation period cells were analyzed by flow cytometry to determine the effects of the treatment on cell cycle progression.

The data shows that dCK inhibition by F2.2.1 synergizes with thymidine to induce cell cycle arrest in several human cancer cell lines. Table 3 shows the % S-phase arrest of cells in cycle treated with thymidine (dT) in the absence and presence of dCK inhibitor Compound F2.2.1.

TABLE 3

| Cell type | dT without dCKi % S-phase arrest (of cells in cycle) | dT + dCKi % S-phase arrest (of cells in cycle) |
|---|---|---|
| CEM | 36 | 84.5 |
| NALM-6 | 52 | 79.8 |
| IGROV1 | 35.9 | 60.3 |

Example 6.2

CCRF-CEM (CEM) human acute T lymphoblastic leukemia were treated with 50 mM thymidine (dT) for 72 hours, in the presence or absence of 2.5 mM deoxycytidine and 1 mM deoxycytidine kinase (dCK) inhibitor F2.2.1. At the end of the incubation period cells were analyzed by flow cytometry to determine the effects of the treatment on leukemic cell proliferation and viability.

Figure 7:
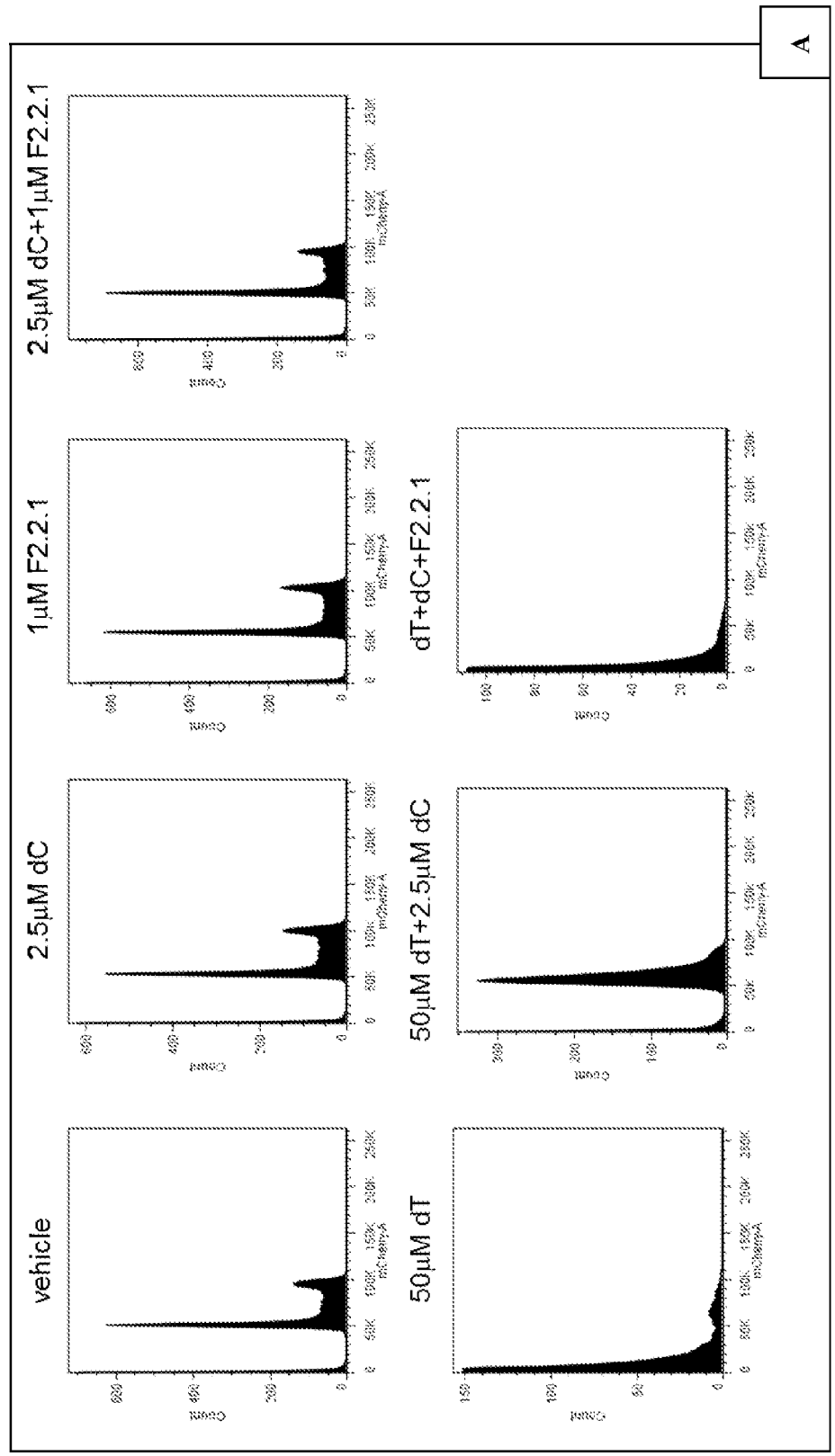
FIG. 7 shows data for DNA damage response (DDR) activation and viability of CEM cells treated for 72 hrs with 50 mM thymidine (dT)+/−1 mM F2.2.1 in the presence of 2.5 mM deoxycytidine (dC). Panel A shows the effects of treatment on cell cycle. Panel B shows the effects of treatment on apoptosis induction (cleaved PARP) and the activation of the DNA damage response biomarker phospho-Chk2 (pChk2). At the end of the incubation period cells were analyzed by flow cytometry to determine the effects of the treatment on leukemic cell proliferation and viability (Panel C).

FIG. 7-A shows the effects of treatment on cell cycle. FIG. 7-B shows the effects of treatment on apoptosis induction (cleaved PARP) and the activation of the DNA damage response biomarker phosho-Chk2 (pChk2). At the end of the incubation period cells were analyzed by flow cytometry to determine the effects of the treatment on leukemic cell proliferation and viability (FIG. 7-C). Compound F2.2.1 alone at 1 µM showed little effect on cell viability over a period of 72 hours; the presence of 2.5 µM of deoxycytidine (dC) appeared to have decreased the number of viable cells relative to vehicle control. Thymidine (dT) at 50 µM suppressed cell growth but failed to shut down the cell cycle. Addition of 2.5 µM dC rescued the cell cycle from the thymidine block by the salvage pathway. However, combination of 1 µM of Compound F2.2.1 and 50 µM of dT almost completely shut down the growth of CEM cells, which could not be rescued by 2.5 µM of dC.

This experiment demonstrated that dCK inhibition by F2.2.1 synergizes with thymidine to significantly reduce the proliferation of human leukemia cells. The effect involves S-phase arrest, activation of the DNA damage response, followed by apoptosis.

Example 6.3

Figure 8:
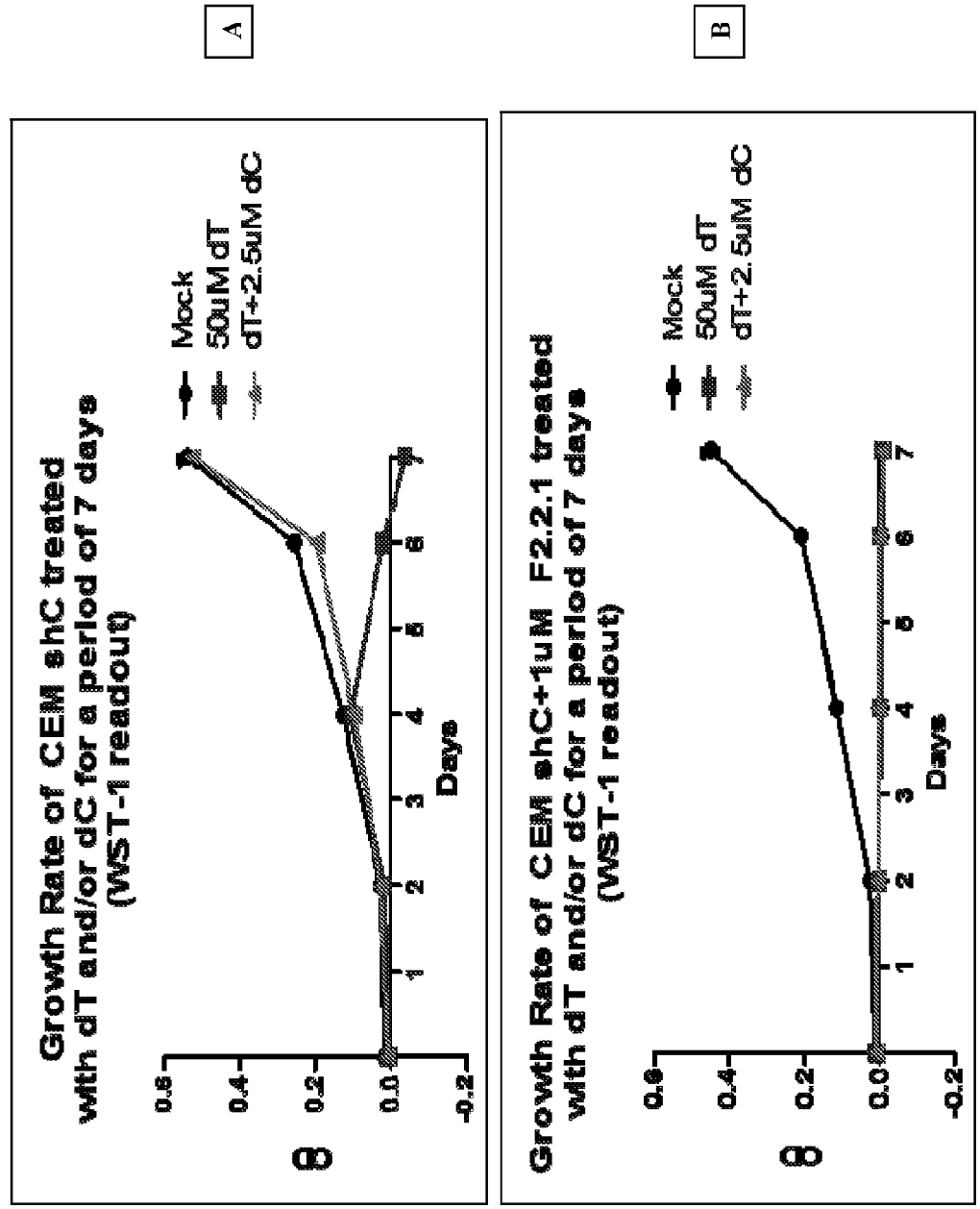
FIG. 8 shows the effect of Compound F2.2.1 on the growth of CEM shC cells treated with dT and/or dC over a period of 7 days. Panel A shows the growth of CEM shC cells treated with dT and/or dC; Panel B shows the growth of CEM shC cells treated with dT and/or dT in addition to Compound F2.2.1. Compound F2.2.1 was not used in "Mock" experiments in either panel A or B.

CCRF-CEM (CEM) human acute T lymphoblastic leukemia were treated with 50 mM thymidine (dT) for 72 hours, in the presence or absence of 2.5 mM deoxycytidine and 1 mM deoxycytidine kinase (dCK) inhibitor F2.2.1. At the end of the incubation period cells the effects of the treatment on leukemic cell proliferation and viability were determined (FIG. 8).

Compound F2.2.1 completely suppressed the growth of thymidine (dT) treated CEM cells for a period of 7 days, which demonstrates that dCK inhibition by F2.2.1 synergizes with thymidine to significantly reduce the proliferation of human leukemia cells.

Example 6.4

Figure 9:
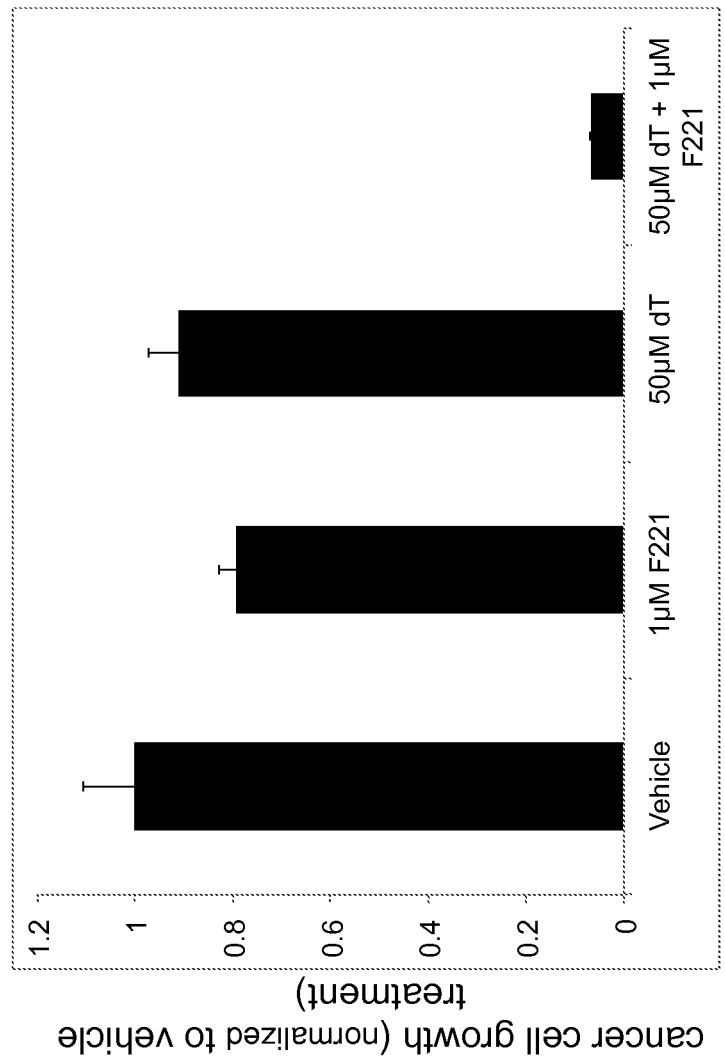
FIG. 9 shows the synergistic effect of Compound F2.2.1 in combination with thymidine on the growth of CEM human leukemia cells.

CCRF-CEM (CEM) human acute T lymphoblastic leukemia were treated with 50 µM thymidine (dT) for 72 hours, in the presence or absence of 1 µM deoxycytidine kinase (dCK) inhibitor F2.2.1. At the end of the incubation period cells were analyzed by flow cytometry to determine the effects of the treatment on leukemic cell proliferation and viability. The result demonstrated that dCK inhibition by Compound F2.2.1 synergizes with thymidine to significantly reduce the proliferation of human leukemia cells (FIG. 9).

Example 6.5

Figure 10:
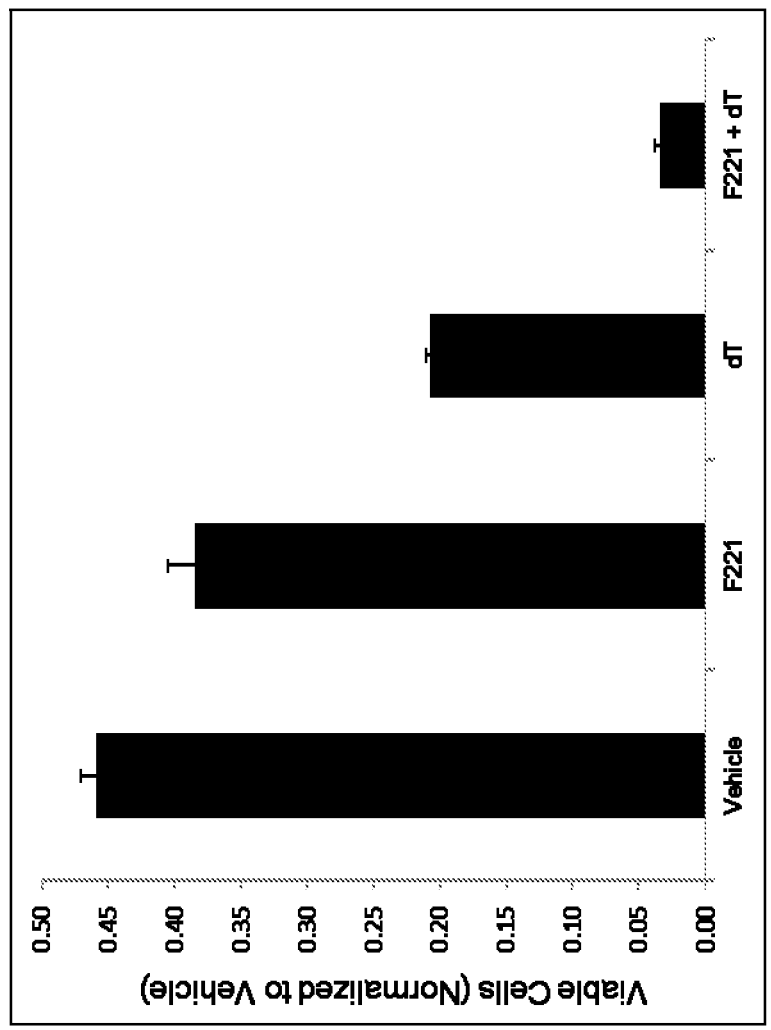
FIG. 10 shows the synergistic effect of Compound F2.2.1 in combination with thymidine on the growth of NALM-6 human leukemia cells.

NALM-6 human acute B lymphoblastic leukemia were treated with 1.6 mM thymidine (dT) for 72 hours, in the presence or absence of 1 µM deoxycytidine kinase (dCK) inhibitor F2.2.1. At the end of the incubation period cells were analyzed by flow cytometry to determine the effects of the treatment on leukemic cell proliferation and viability. Cell culture media contained 1.25 µM deoxycytidine. The result again showed that dCK inhibition by F2.2.1 synergizes with thymidine to significantly reduce the proliferation of human leukemia cells (FIG. 10).

Example 6.6

Figure 11:
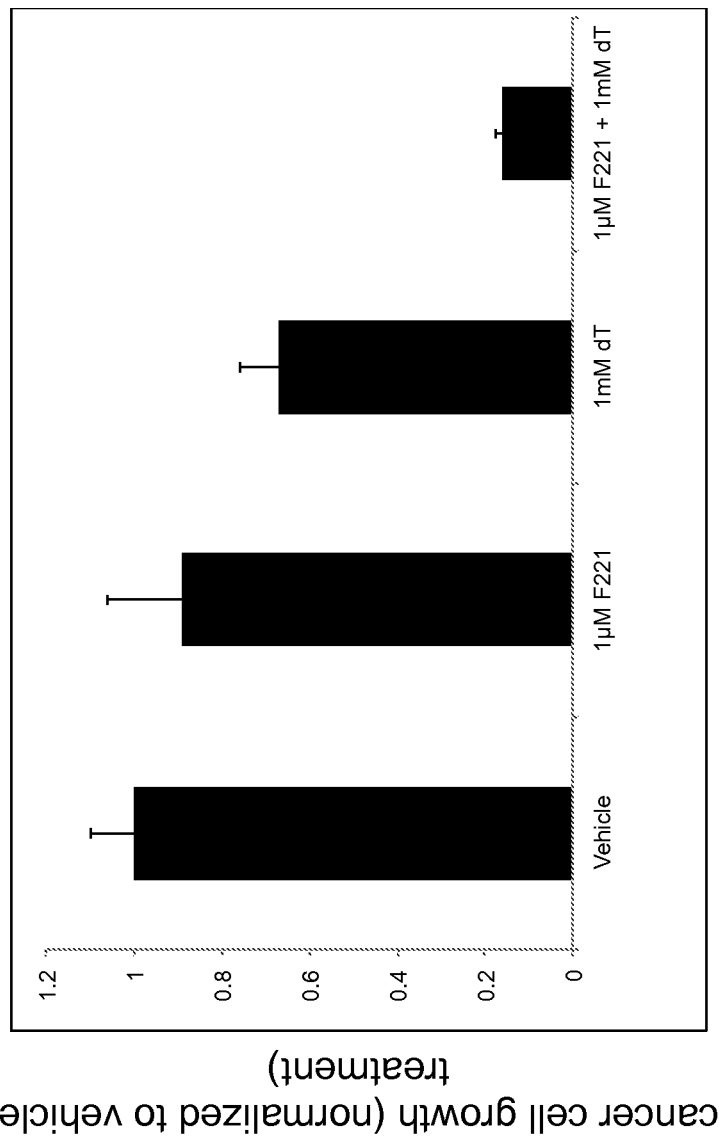
FIG. 11 shows the synergistic effect of Compound F2.2.1 in combination with thymidine on the growth of A549 human lung cancer cells.

A549 human lung adenocarcinoma cells were treated with 1 mM thymidine (dT) for 72 hours, in the presence or absence of 1 µM deoxycytidine kinase (dCK) inhibitor F2.2.1. At the end of the incubation period cells were analyzed by flow cytometry to determine the effects of the treatment on cell proliferation and viability. The result demonstrated that dCK inhibition by F2.2.1 synergizes with thymidine to significantly reduce the proliferation of human lung adenocarcinoma cells (FIG. 11).

Example 7

Test for Sensitization of Tumor Cells to Thymidine Treatment In Vivo by Inhibition of dCK Activity Materials and Methods:

NOD scid IL2 receptor gamma chain knockout mice (NSG) were injected intravenously with 10 million CEM human acute leukemia cells that were either transduced with a control shRNA construct (shC cell) or with a shRNA specific for deoxycytidine kinase (shdCK cells). shdCK cells express less than 10% active dCK compared to shC cells. Thymidine (dT) treatment (at 1 g/kg, administered every 12 hrs by intraperitoneal injection) was initiated 15 days after injection of leukemic cells. Experimental groups were as follows: 1) shC vehicle (N=6): mice implanted with shC cells and treated with vehicle; 2) shdCK vehicle (N=6): mice implanted with shdCK cells and treated with vehicle; 3) shC thymidine (N=6): mice implanted with shC cells and treated with thymidine; 4) shdCK thymidine (N=6): mice implanted with shdCK cells and treated with thymidine.

Figure 12:
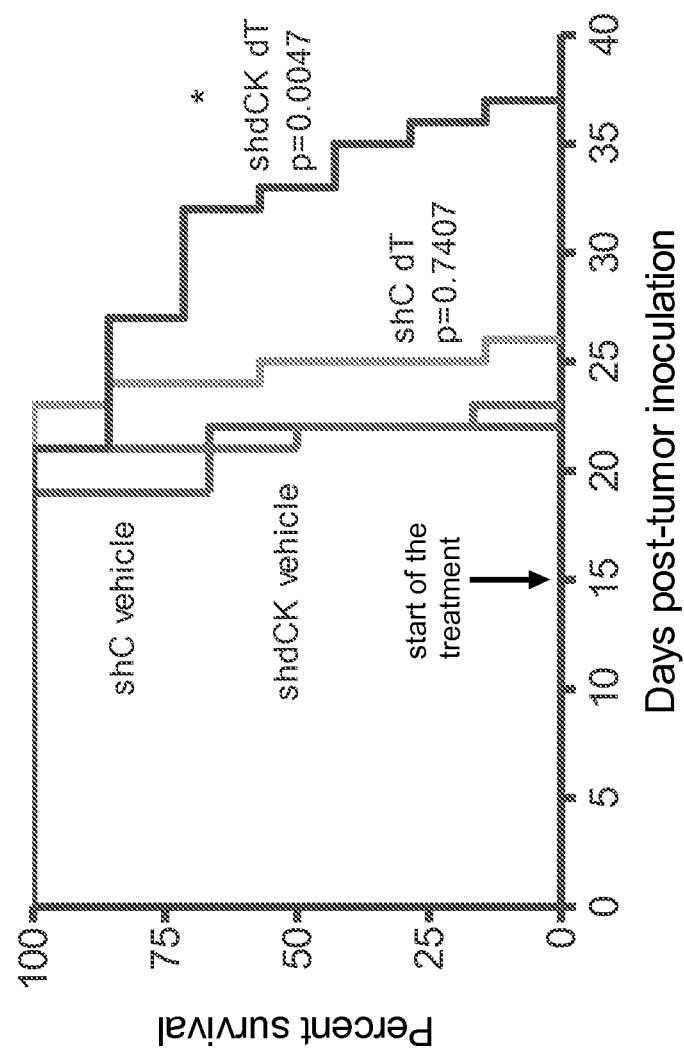
FIG. 12 shows the effect of inhibition of dCK activity using RNA interference on susceptibility of CEM leukemias to thymidine treatment in vivo.

The results demonstrated that inhibition of dCK activity using RNA interference renders CEM leukemias susceptible to thymidine treatment (FIG. 12). These data suggest that a small molecule inhibitor of dCK can combined with thymidine for treatment of acute T lymphoblastic leukemias.

Example 8

In Vitro Test for dCK Inhibition to Block T Lymphocyte Proliferation

Materials and Methods:

Primary murine T cells were obtained from C57/BL6 mice. T cells were cultured in X-VIVO15 media and were stimulated with an antibody (clone 145-2C11) against the epsilon chain of the T cell receptor. Prior to antibody-mediated activation, T cells were labeled with the fluorescent dye CFSE to allow measurements of cell division.

Activated T cells were treated with vehicle (DMSO—mock treatment), and two dCK inhibitors: F.2.2.1 and DI-26. The dCK inhibitors were used at 1 µM final concentration. 72 hours after activation, T cells were analyzed by flow cytometry to determine their viability, numbers and history of cell division.

The results showed that inhibition of dCK activity using Compounds F2.2.1 or DI-26 significantly blocks T cell proliferation (FIG. 13). These findings indicate that mature T cells require dCK activity for optimal activation and suggest that dCK inhibitors are useful in disorders characterized by overt immune activation such as autoimmunity and transplant rejection.

Example 9

In Vivo Test for Loss of dCK Activity in Preventing Experimental Autoimmune Encephalomyelitis (EAE)

Materials and Methods:

dCK wild type (dCK+/+), heterozygous (dCK+/−) and knockout (dCK−/−) female mice (7-10 weeks old) were immunized s.c. with 100 µg of MOG35-55 (MEVGWYR-SPFSRVVHLYRNGK) (SEQ. ID No.: 1) peptide in an emulsion of incomplete Freund's adjuvant (F5506; Sigma, St. Louis, Mo.) and lyophilized heat-inactivated *Mycobacterium tuberculosis* (100 µg per mouse, lot no. 3114-33, strain H37Ra; Difco, Detroit, Mich.) distributed on four sites on the back. Mice were injected i.p. with 200 ng of PTX (516561, Calbiochem, Darmstadt, Germany) in PBS on days 0 and 2. Mice were scored for the severity of the disease by using the following scale: 0, no abnormality; 1, limp tail; 2, mild hind limb weakness; 3, severe hind limb weakness; 4, complete hind limb paralysis; 5, quadriplegia or premoribound state.

Figure 14:
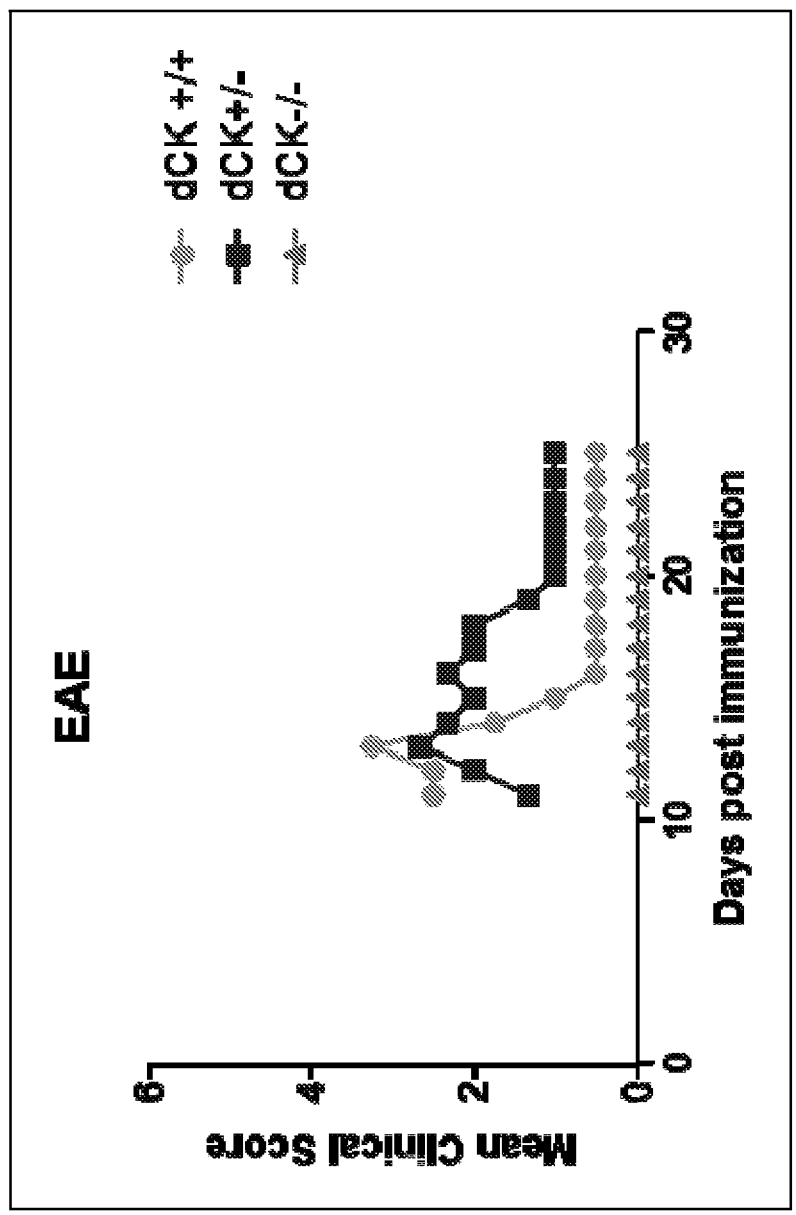
FIG. 14 shows the in vivo effect of loss of dCK activity (dCK Knockout mice) on experimental autoimmune encephalomyelitis (EAE).
Figure 15A:
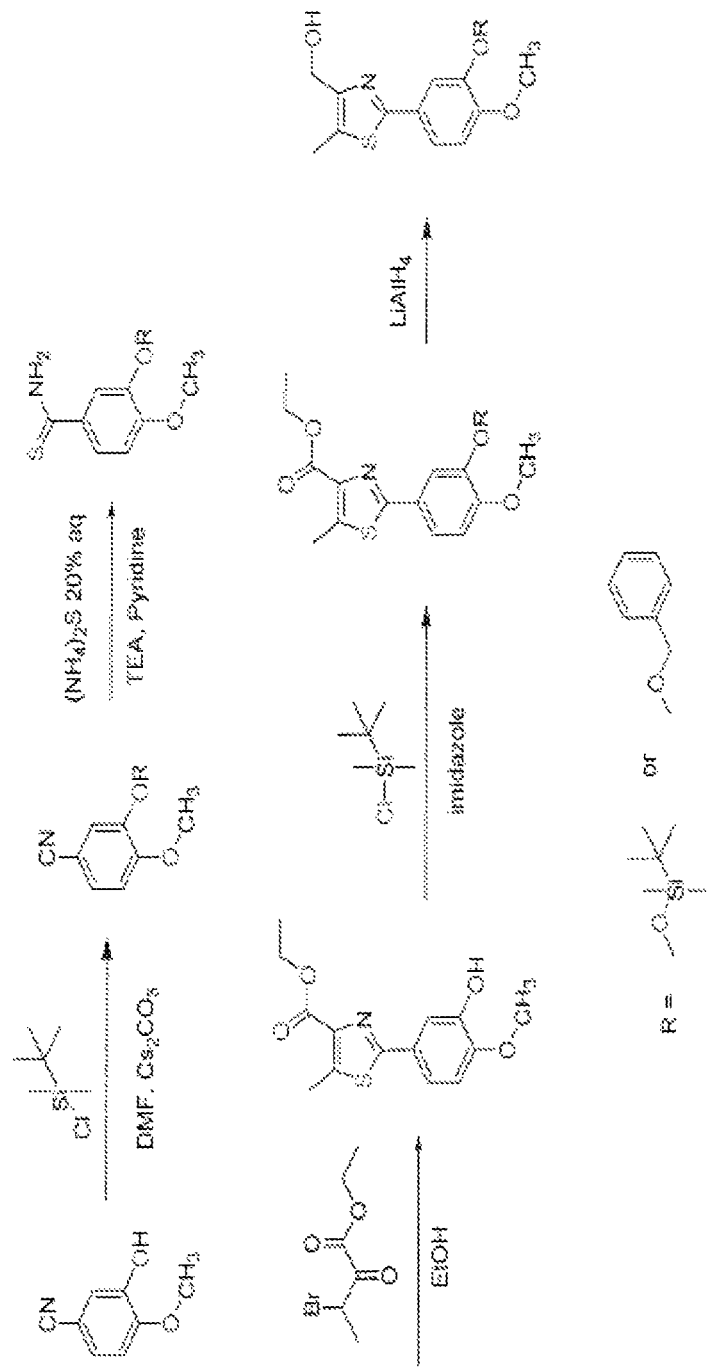
FIGS. 15A and 15B show a reaction scheme for radiolabelling of Compound DI-F2.2.1 for PET imaging studies.
Figure 15B:
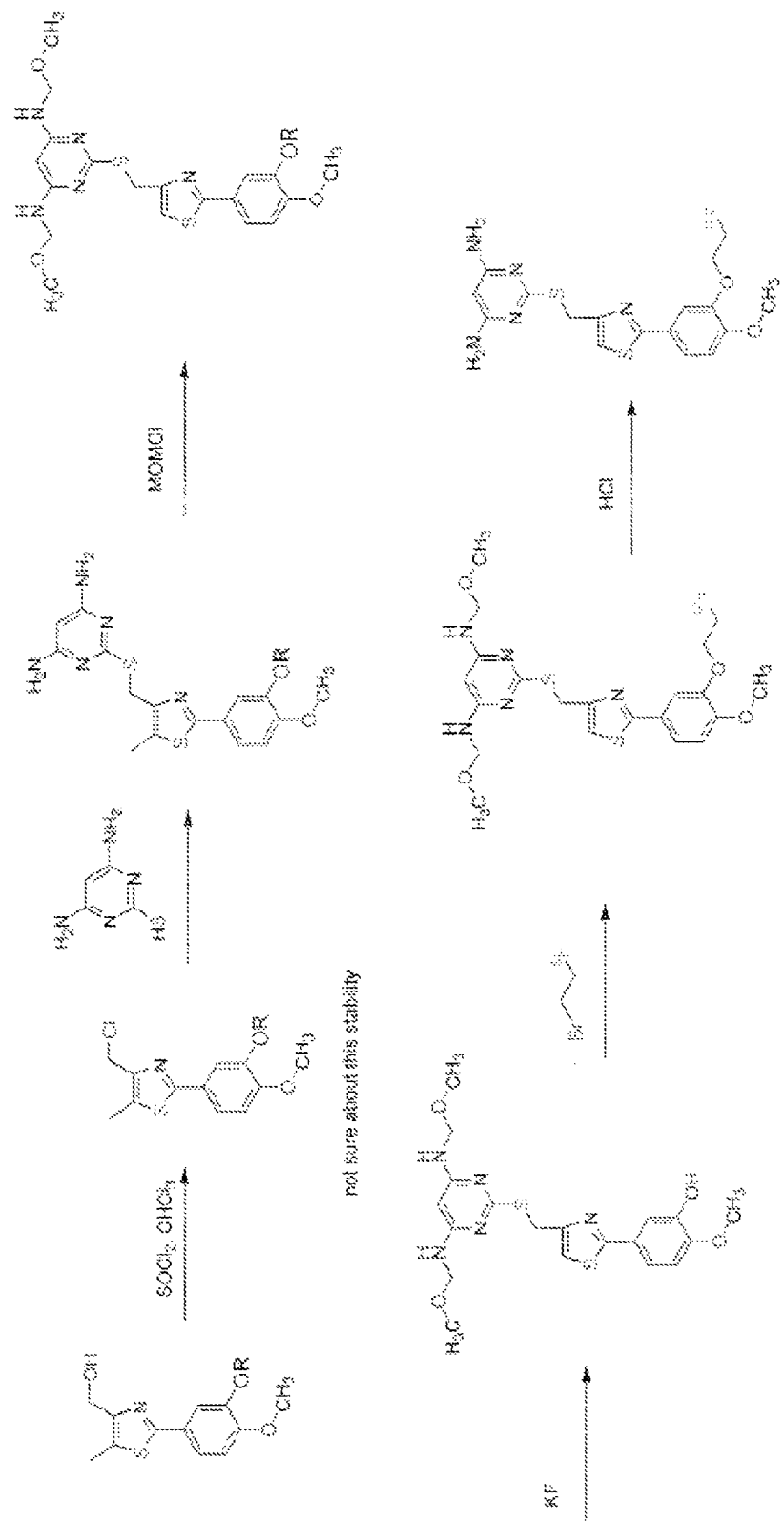
Figure 17:
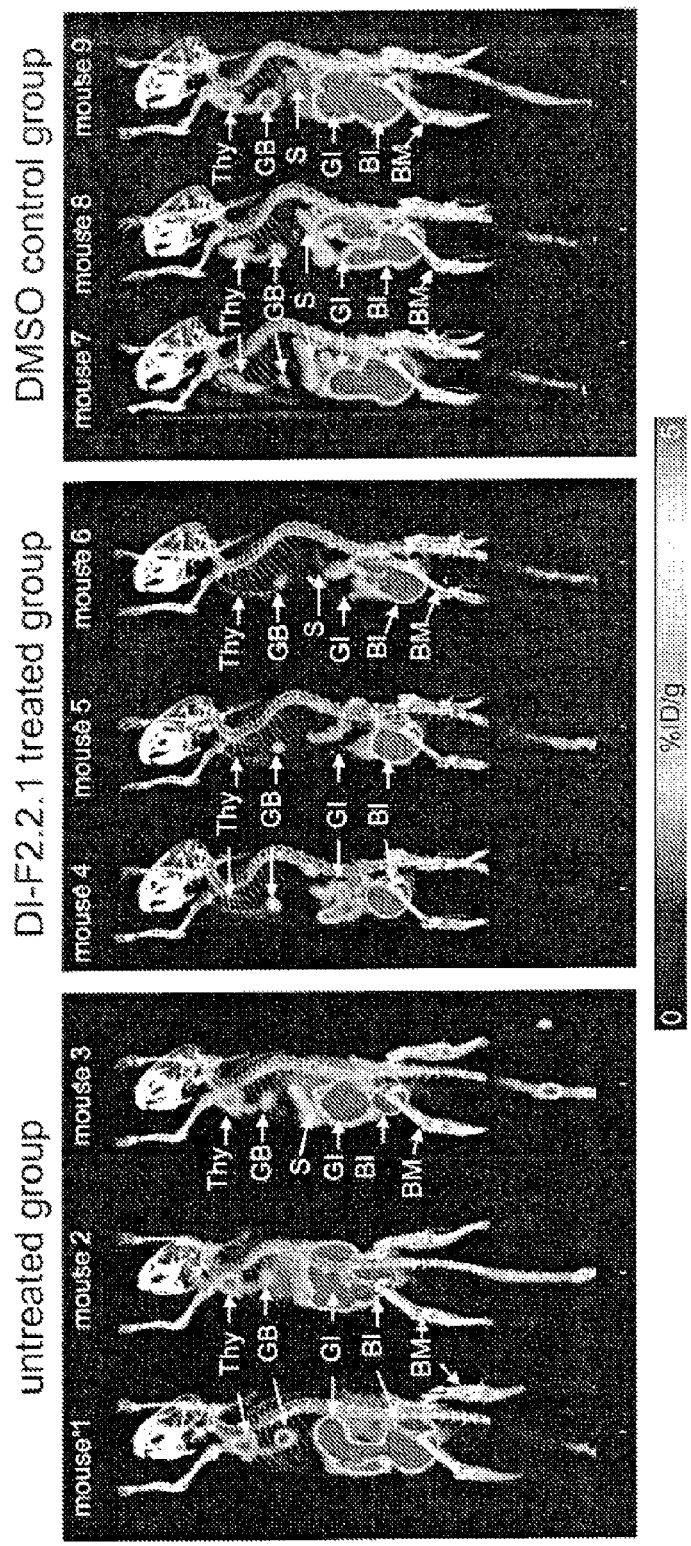
FIG. 17 provides additional PET imaging data showing inhibition of L-FMAC by Compound DI-F2.2.1.
Figure 18:
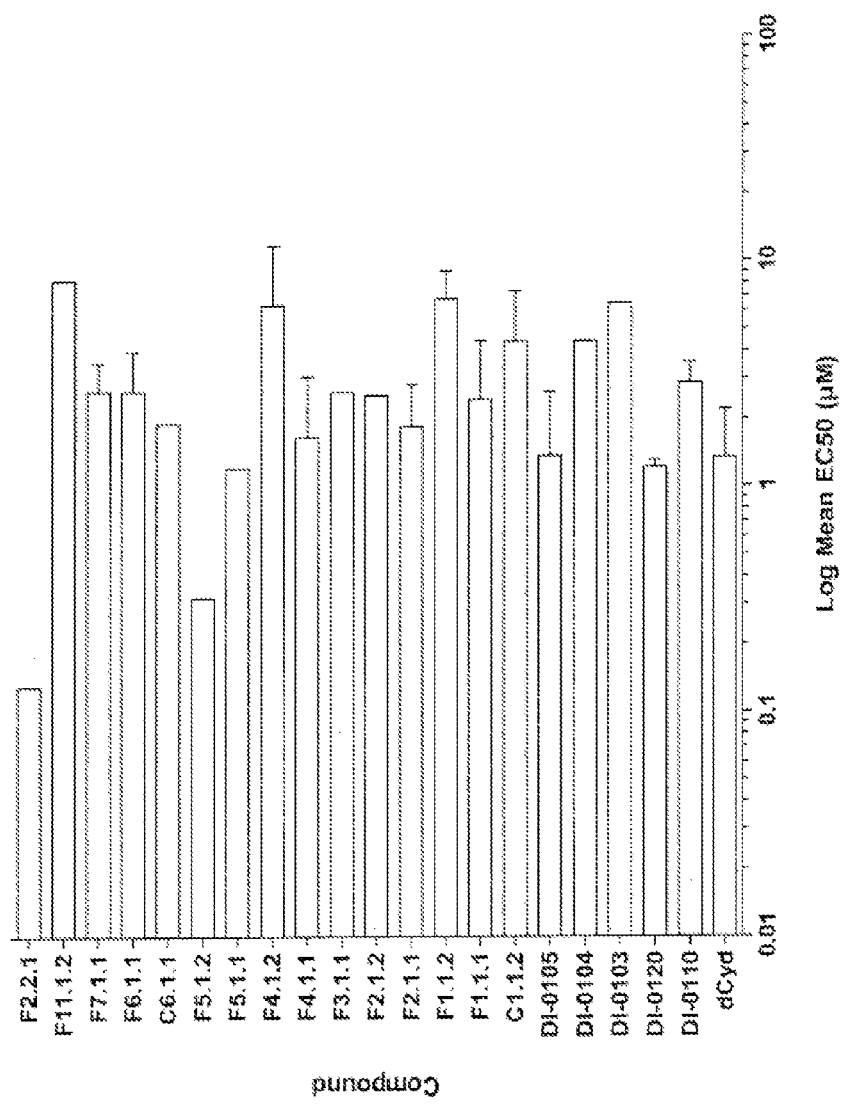
FIG. 18 shows inhibition of [$^3$H]-deoxycytidine (dCyd) phosphorylation by recombinant human dCK.
Figure 19:
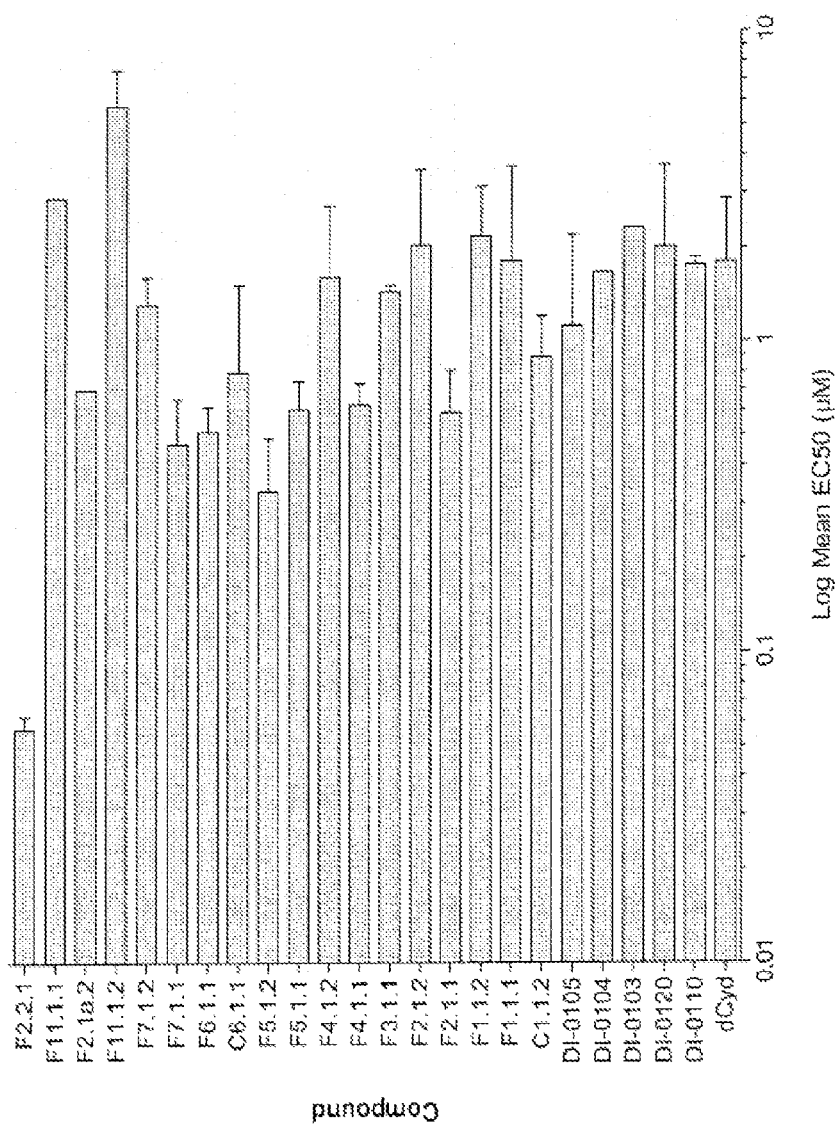
FIGS. 19 and 20 show additional data for the inhibition of [$^3$H]-dCyd uptake by L1210 cells.
Figure 20:
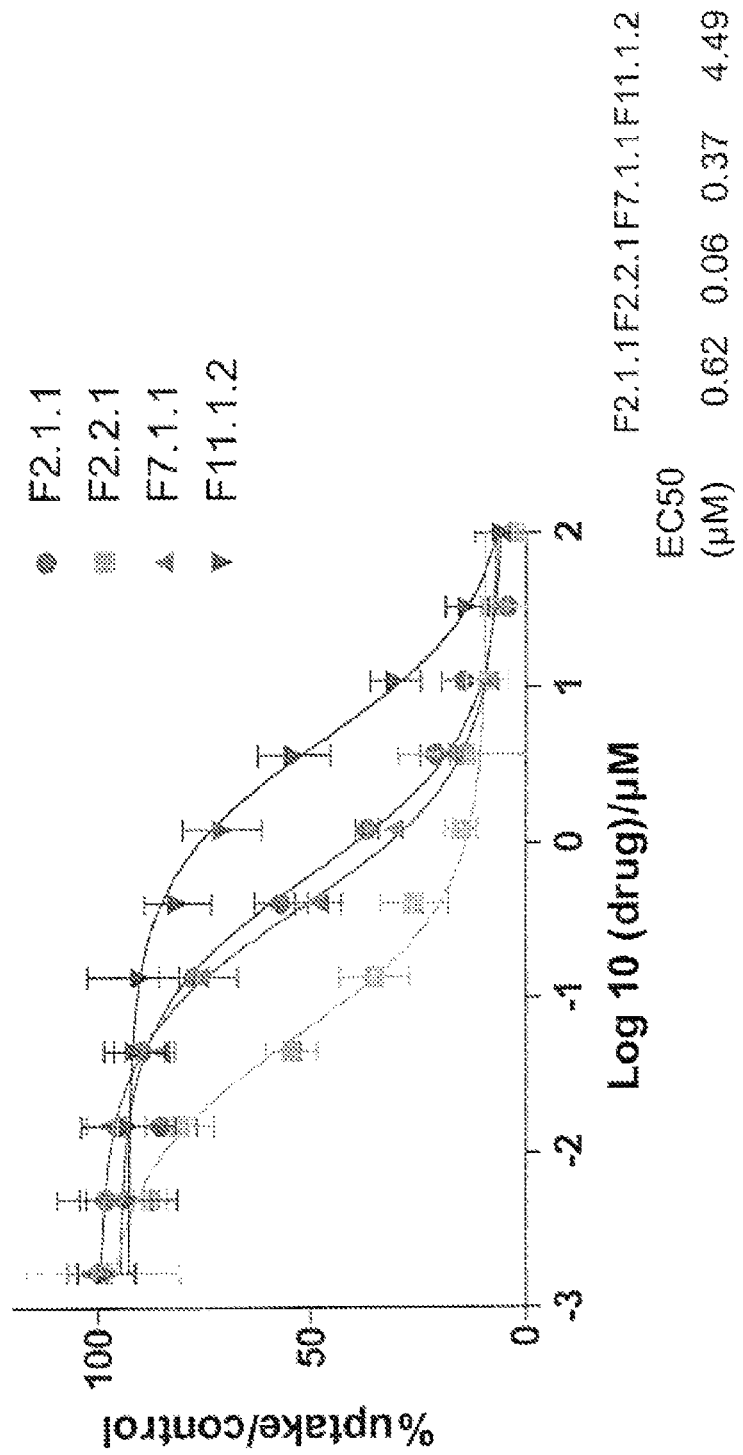
Figure 21:
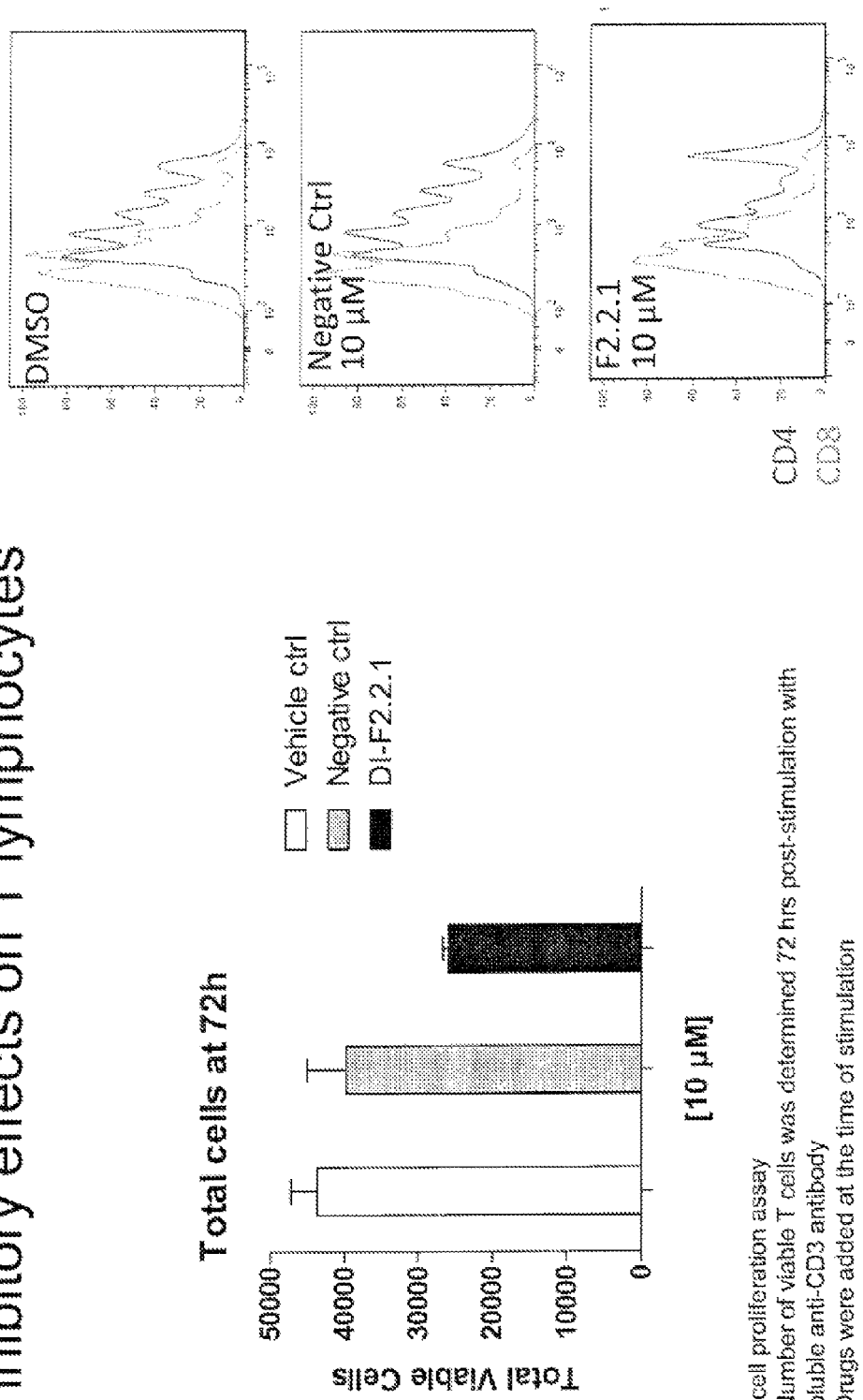
FIG. 21 illustrates data showing the inhibitory effect of Compound F2.2.1 on T lymphocytes.
Figure 22:
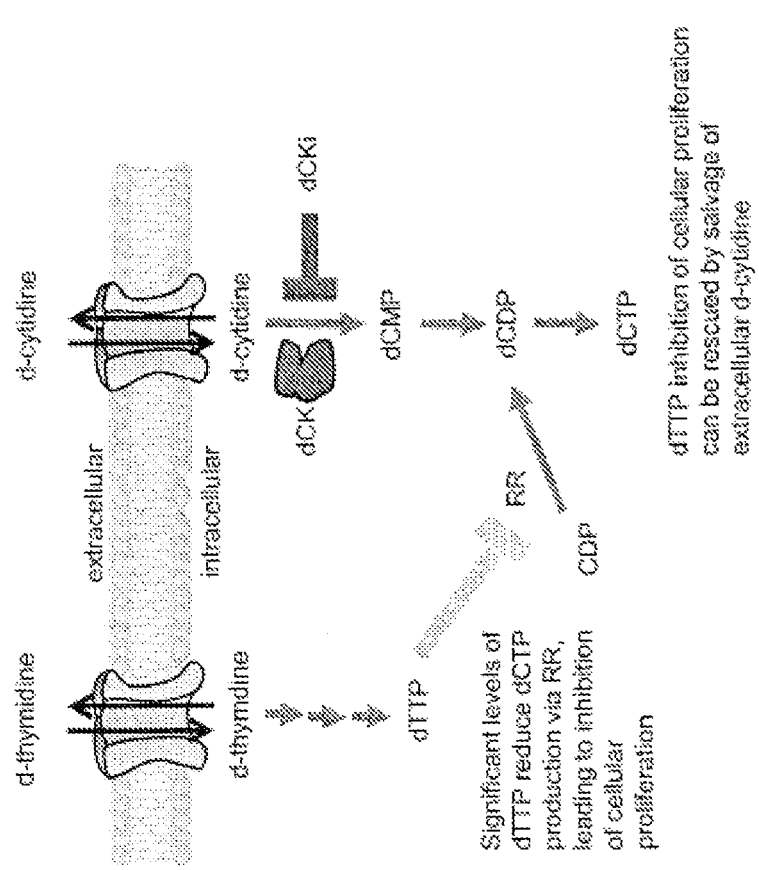
FIG. 22 is a schematic showing the de novo pathway for DNA synthesis and the salvage pathway.
Figure 23:
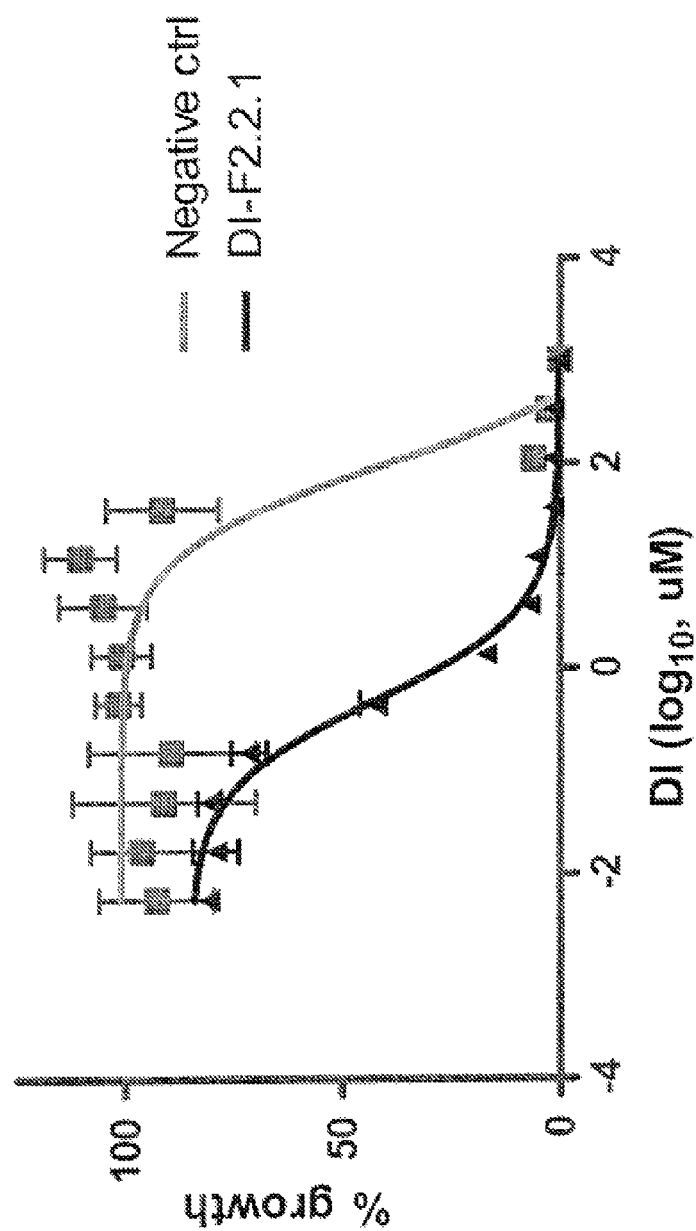
FIG. 23 provides additional data showing inhibition of dCyd rescue of the thymidine block by Compound DI-F2.2.1. Simultaneous inhibition of the de novo pathway for DNA synthesis by thymidine and the salvage pathway by Compound DI-F2.2.1 has anti-tumor effects.

The results shown in FIG. 14 demonstrate that loss of dCK activity prevents the induction of EAE in mice. EAE is "the" prototypic organ-specific autoimmune disorder and shares many similarities to the human disease multiple sclerosis (MS). These findings suggest that small molecule inhibitors of dCK can be useful in MS and potentially other T cell mediated autoimmune disorders.

Further embodiments and descriptions are provided in FIGS. 16 through 23.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

All references cited herein, including patent applications and publications, are hereby incorporated by reference in their entirety.

What is claimed is:
1. A compound of the formula (I):

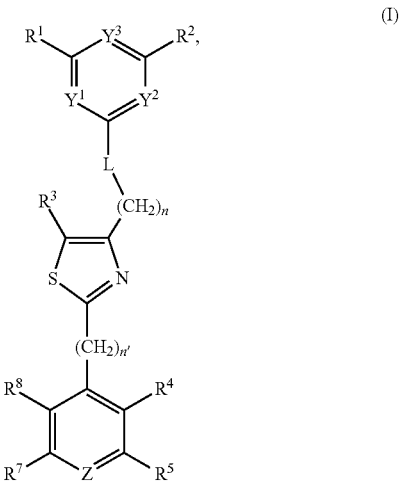

or a salt thereof, wherein:
$R^1$ and $R^2$ are independently H, OH, $OR^{14}$, $NH_2$, $NHC(O)R^{15}$ or $NHC(O)OR^{17}$;
each $Y^1$, $Y^2$ and $Y^3$ is independently N or CH, wherein at least one of $Y^1$, $Y^2$, and $Y^3$ is N;
L is O, S, SO, $SO_2$, Se, NH or $NR^{16}$;
each m, n, p, q and r is independently 1, 2, 3, 4, 5 or 6;
n' is 0, 1, 2, 3, 4, 5 or 6;
$R^3$ is $C_1$-$C_6$ alkyl, $C_3$-$C_8$ cycloalkyl, aryl, heteroaryl or $OCH_3$;
$R^4$ and $R^8$ are independently H, F, Cl, Br, I, $CF_3$ or $OR^9$;
$R^5$ and $R^7$ are independently H, F, Cl, Br, I, $CF_3$, fluoropyridyl or $OR^{10}$;
Z is N or $CR^6$;
$R^6$ is H, F, Cl, Br, I, $CF_3$ or $OR^{11}$;
$R^9$ and $R^{11}$ are independently $C_1$-$C_6$ alkyl, $C_1$-$C_6$ perfluoroalkyl, $(CH_2)_mX$, $(CH_2)_pOR^{12}$, or $(CH_2)_rX^*$,
$R^{10}$ is $C_1$-$C_6$ alkyl, $C_1$-$C_6$ perfluoroalkyl, $(CH_2)_mX$, $(CH_2)_pOR^{12}$, $(CH_2)_qR^{13}$ or $(CH_2)_rX^*$;
$R^{12}$ is H, tosyl or 2-tetrahydropyranyl;
$R^{13}$ is $OCH_3$, $NH_2$, $NHCOCH_3$, $CO_2H$, $CO_2CH_3$, SH or $COCH_3$;
$R^{14}$ is $C_1$-$C_4$ alkyl;
$R^{15}$ is $C_1$-$C_6$ alkyl or $CF_3$;
$R^{16}$ is C1-C4 alkyl or phenyl;
$R^{17}$ is $C_1$-$C_6$ alkyl;
X is F, Cl, Br or I; and
$X^*$ is $^{18}F$, $^{75}Br$, $^{76}Br$ or $^{124}I$.

2. The compound of claim 1, wherein $R^1$ and $R^2$ are independently H, $NH_2$, $NHC(O)R^{15}$ or $NHC(O)OR^{17}$; or a salt thereof.

3. The compound of claim 2, wherein each $R^1$ and $R^2$ is $NH_2$; or a salt thereof.

4. The compound of claim 2, wherein each $R^1$ and $R^2$ is $NHC(O)R^{15}$; or a salt thereof.

5. The compound of claim 4, wherein $R^{15}$ is $CH_3$; or a salt thereof.

6. The compound of claim 4, wherein $R^{15}$ is $CF_3$; or a salt thereof.

7. The compound of claim 1, wherein $R^5$ is F, Cl, Br, I, $CF_3$, fluoropyridyl or $OR^{10}$; or a salt thereof.

8. The compound of claim 7, wherein $R^5$ is $OR^{10}$; or a salt thereof.

9. The compound of claim 8, wherein $R^{10}$ is $C_1$-$C_6$ alkyl, $C_1$-$C_6$ perfluoroalkyl, $(CH_2)_mX$, $(CH_2)_pOR^{12}$ or $(CH_2)_rX^*$; or a salt thereof.

10. The compound of claim 9, wherein $R^{10}$ is $(CH_2)_rX^*$; or a salt thereof.

11. The compound of claim 10, wherein $X^*$ is $^{18}F$; or a salt thereof.

12. The compound of claim 1, wherein the compound is of the formula (A):

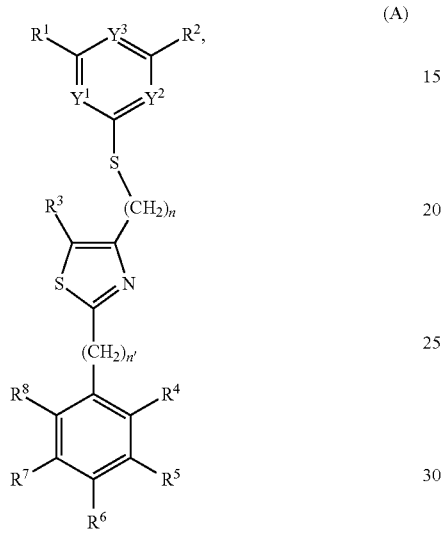

or a salt thereof, wherein:

$R^1$ and $R^2$ are independently $NH_2$, OH, $OCH_3$ or $OC_2H_5$;

each $Y^1$, $Y^2$ and $Y^3$ is independently N or CH, wherein at least one of $Y^1$, $Y^2$, and $Y^3$ is N;

n is 1, 2, 3, 4, 5 or 6;

n' is 0, 1, 2, 3, 4, 5 or 6;

$R^3$ is $CH_3$, $C_2H_5$, $C_3H_7$ or $OCH_3$;

each $R^4$, $R^5$, $R^6$, $R^7$ and $R^8$ is independently H, F, Cl, Br, I or $OR^9$;

each $R^9$ is independently $CH_3$, $C_2H_5$, $C_3H_7$, $C_4H_9$, $C_5H_{11}$, $C_6H_{13}$, $CH_2F$, $C_2H_4F$, $C_3H_6F$, $C_4H_8F$, $C_5H_{10}F$, $C_6H_{12}F$, $C_2H_4Br$, $C_2H_4I$, $CF_3$, $C_2F_5$, $C_3F_7$, $C_4F_9$, $C_5F_{11}$, $C_6F_{13}$, $CH_2OTs$, $C_2H_4OTs$, $C_3H_6OTs$, $C_4H_8OTs$, $C_5H_{10}OTs$, $C_6H_{12}OTs$, $CH_2OH$, $C_2H_4OH$, $C_3H_6OH$, $C_4H_8OH$, $C_5H_{10}OH$, $C_6H_{12}OH$, $CH_2OTHP$, $C_2H_4OTHP$, $C_3H_6OTHP$, $C_4H_8OTHP$, $C_5H_{10}OTHP$ or $C_6H_{12}OTHP$, $CH_2X^*$, $C_2H_4X^*$, $C_3H_6X^*$, $C_4H_8X^*$, $C_5H_{10}X^*$, $C_6H_{12}X^*$;

wherein Ts is tosyl;

wherein THP is 2-tetrahydropyranyl group; and wherein $X^*$ is selected from: $^{18}F$, $^{75}Br$, $^{76}Br$ or $^{124}I$.

13. The compound of claim 1, wherein the compound binds to a deoxycytidine kinase polypeptide.

14. The compound of claim 1, or a salt thereof, and a pharmaceutically acceptable carrier.

15. A method for inhibiting a deoxycytidine kinase (dCK) activity comprising contacting a compound of claim 1 with the deoxycytidine kinase.

16. A compound, or salt thereof, wherein the compound is selected from the group consisting of:

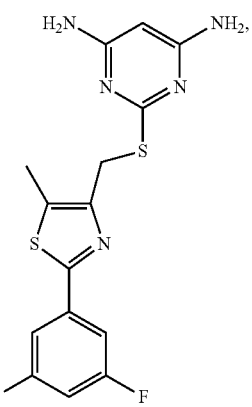

DI-01

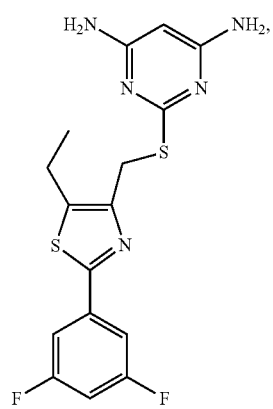

DI-02

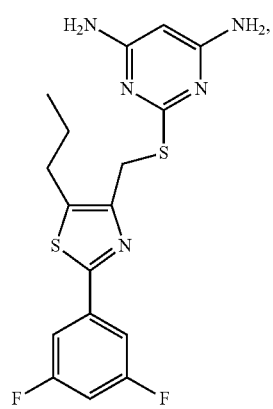

DI-03

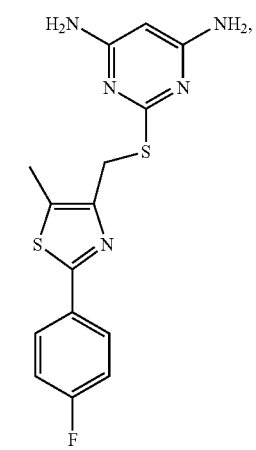

DI-04

DI-05
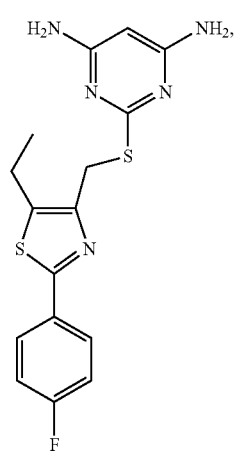
DI-06
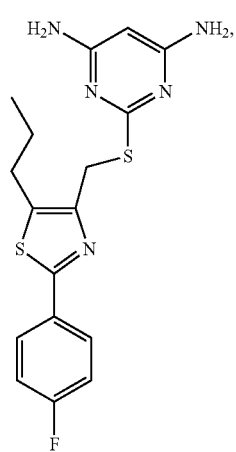
DI-07
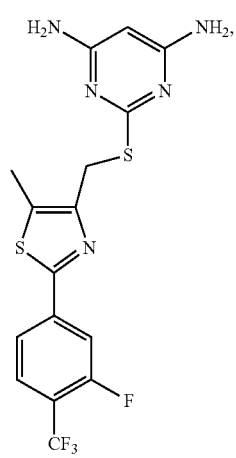
DI-08
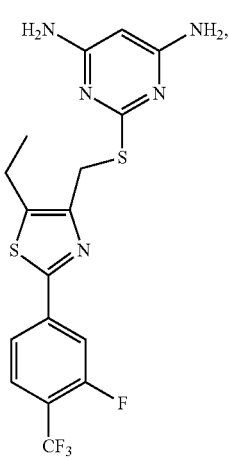
DI-09
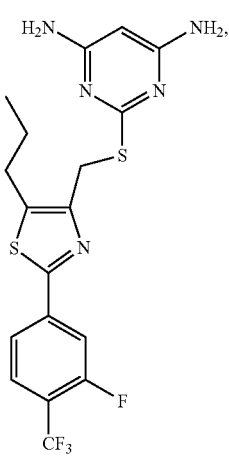
DI-10
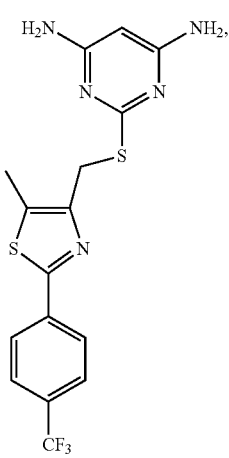

-continued
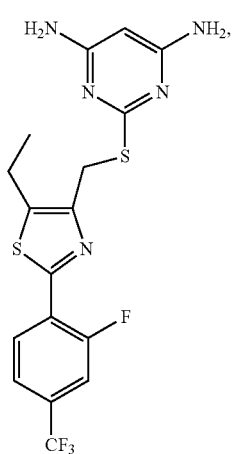
DI-11
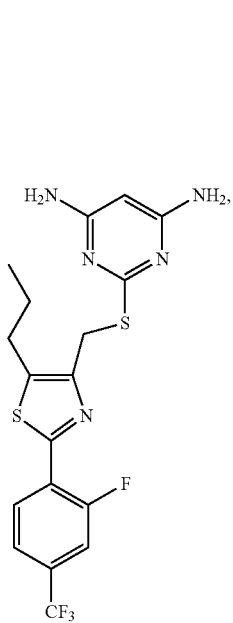
DI-12
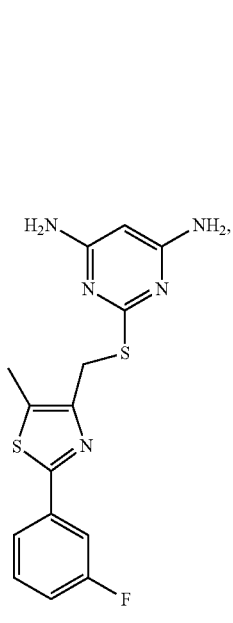
DI-13
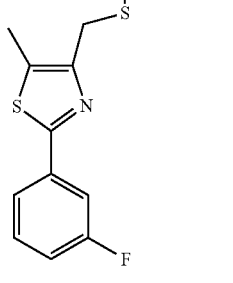
-continued
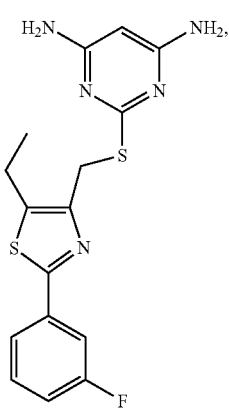
DI-14
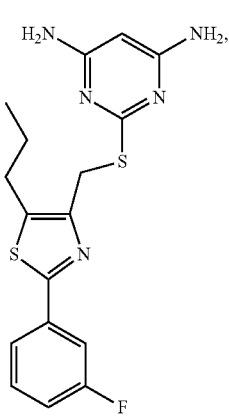
DI-15
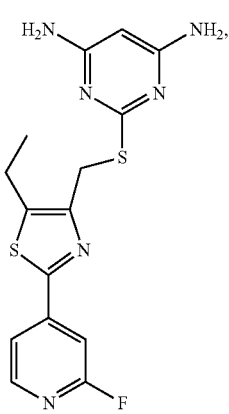
DI-16
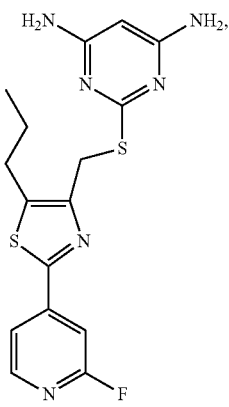
DI-17

DI-18
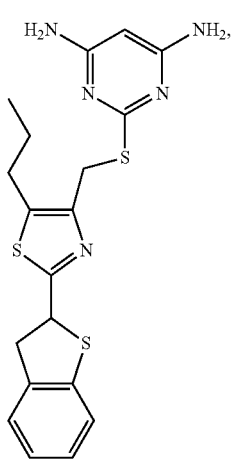
DI-19
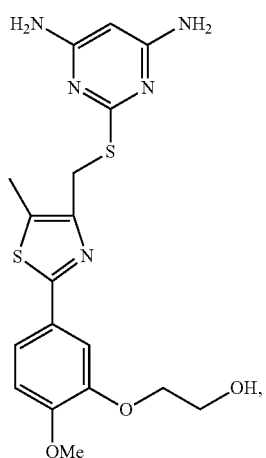
DI-20
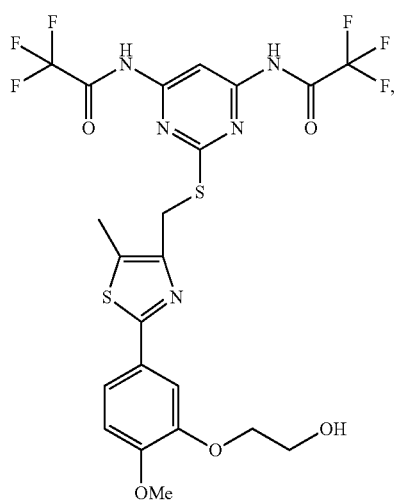
DI-23
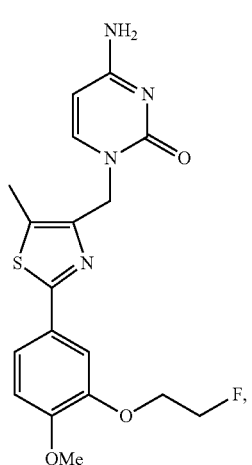
DI-22
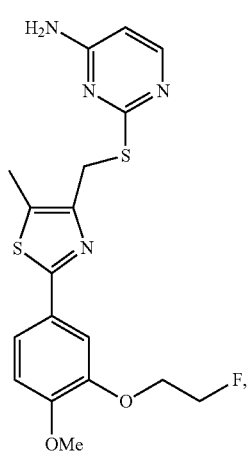
DI-24
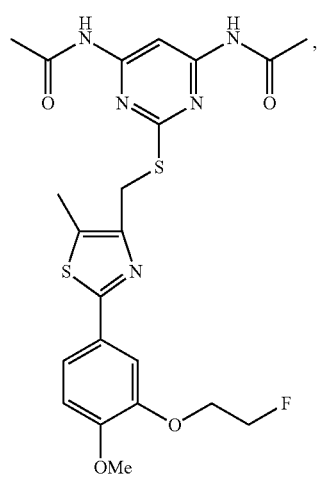

-continued
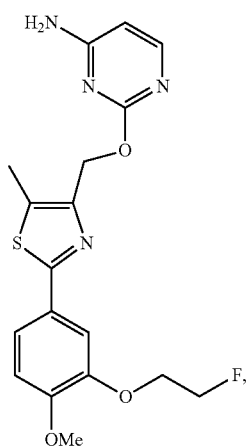
DI-25
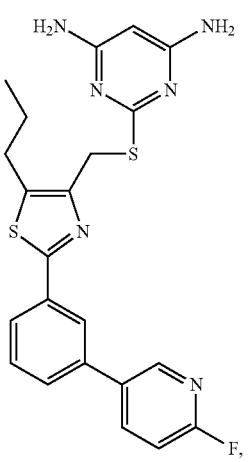
DI-28
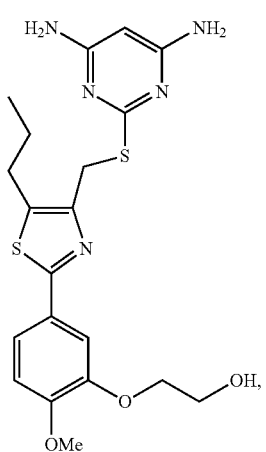
DI-26
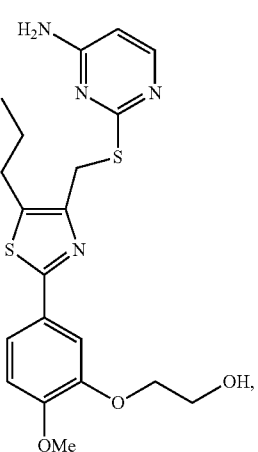
DI-27
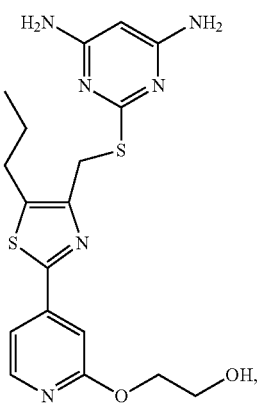
DI-30

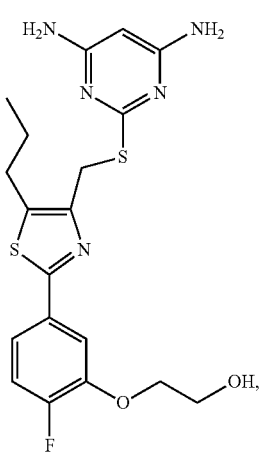
DI-31
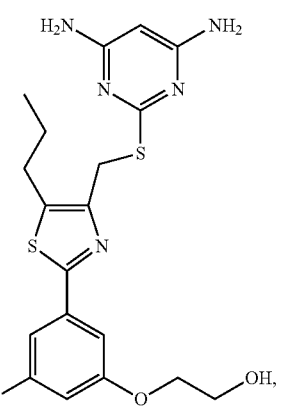
DI-32
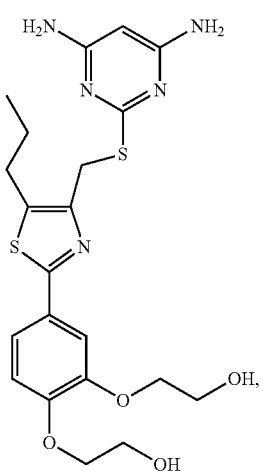
DI-33
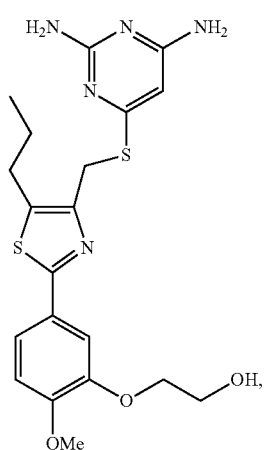
DI-34
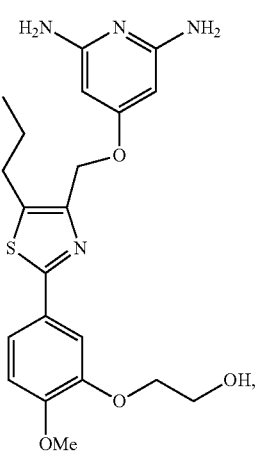
DI-35
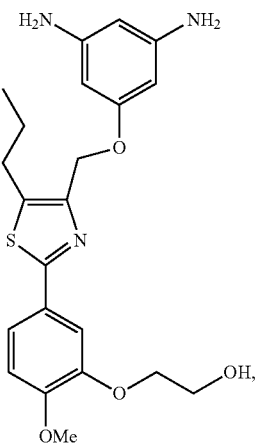
DI-36

-continued

DI-37
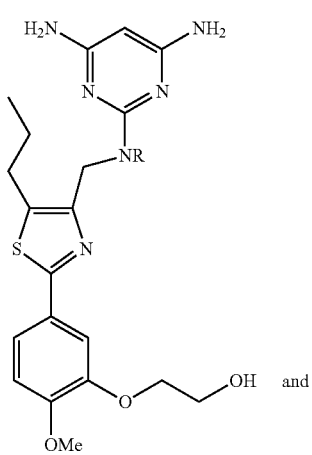
R = H, Me, Et, Pr, Bu, Ph

DI-38
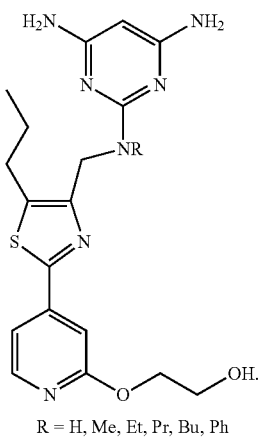
R = H, Me, Et, Pr, Bu, Ph

17. A method of imaging, comprising:

administering a radiolabeled compound of claim 1 to an animal or human;

performing PET imaging to determine a local concentration of the compound in the animal or human; and correlating the local concentration of the compound with a local immune response or the presence of neoplastic tissue.

18. The method of claim 17, further comprising using the local concentration of the compound to diagnose cancer and/or monitor cancer treatment.

19. The method of claim 17, wherein the animal or human has a condition selected from the group consisting of cancer, an autoimmune disorder, a development disorder, viral infection, bacterial infection, parasitical infection, infection, a metabolic disease, and inflammation.

20. The method of claim 17, wherein the animal or human is undergoing a therapy selected from the group consisting of cancer immunotherapy, immunotherapy, interferon therapy, vaccination, radiation therapy, chemotherapy, and antibiotic therapy.

* * * * *